(12) United States Patent
Harvie et al.

(10) Patent No.: US 7,144,414 B2
(45) Date of Patent: *Dec. 5, 2006

(54) SURGICAL PROCEDURES AND INSTRUMENTS

(75) Inventors: Fraser Harvie, Glasgow (GB); Graham Smith, Plaistow, NH (US); Philip B. Sample, Arlington, MA (US); Gary R. McCarthy, East Bridgewater, MA (US); Adam James, Talbot Green (GB); Peter Richardson, Arlington, MA (US)

(73) Assignee: Smith & Nephew, Inc., Memphis, TN (US)

( * ) Notice: Subject to any disclaimer, the term of this patent is extended or adjusted under 35 U.S.C. 154(b) by 304 days.

This patent is subject to a terminal disclaimer.

(21) Appl. No.: 10/335,491

(22) Filed: Dec. 31, 2002

(65) Prior Publication Data

US 2004/0068267 A1  Apr. 8, 2004

Related U.S. Application Data

(63) Continuation-in-part of application No. 09/604,387, filed on Jun. 27, 2000, now Pat. No. 6,620,185.

(51) Int. Cl.
*A61B 17/04* (2006.01)
(52) U.S. Cl. .......... 606/232; 606/215; 606/92
(58) Field of Classification Search .......... 606/72, 606/92, 93, 215, 216, 219, 220, 232
See application file for complete search history.

(56) References Cited

U.S. PATENT DOCUMENTS

| | | | |
|---|---|---|---|
| 3,744,921 A * | 7/1973 | Weller et al. ............ | 401/2 |
| 4,065,817 A | 1/1978 | Branemark et al. ......... | 3/1.91 |
| 4,200,939 A | 5/1980 | Oser ........................ | 3/1.9 |
| 4,263,913 A | 4/1981 | Malmin .................... | 128/330 |
| 4,274,163 A | 6/1981 | Malcom et al. ............ | 3/1.91 |
| 4,494,535 A | 1/1985 | Haig ........................ | 128/92 |
| 4,514,125 A | 4/1985 | Stol ......................... | 411/82 |
| 4,532,661 A | 8/1985 | Halpern .................... | 623/23 |
| 4,554,686 A | 11/1985 | Baker ...................... | 623/16 |
| 4,585,458 A | 4/1986 | Kurland ................... | 623/13 |
| 4,595,713 A | 6/1986 | St. John ................... | 523/105 |
| 4,625,722 A | 12/1986 | Murray ................... | 128/92 VQ |
| 4,645,503 A | 2/1987 | Lin et al. .................. | 623/16 |
| 4,653,487 A | 3/1987 | Maale ..................... | 128/92 VQ |
| 4,696,301 A | 9/1987 | Barabe .................... | 128/335.5 |
| 4,712,957 A | 12/1987 | Edwards et al. .......... | 411/82 |

(Continued)

FOREIGN PATENT DOCUMENTS

DE  25 29 699  1/1977

(Continued)

OTHER PUBLICATIONS

Knee Surg, Sports Traumatol, Arthrosc., Alfredson et al., "Treatment of tear of the anterior cruciate ligament combined with localised deep cartilage defects in the knee with ligament reconstruction and autologous periosteum transplantation", pp. 69-74, vol. 7 (1999).

(Continued)

*Primary Examiner*—Ralph A. Lewis
(74) *Attorney, Agent, or Firm*—Fish & Richardson P.C.

(57) ABSTRACT

Surgical instruments and methods are provided. In one aspect, a method of securing a fixation device within an opening in a tissue is provided, including delivering a material in a flowable state to said opening, and changing the state of the material so that the material forms an interference fit that secures the fixation device in the opening.

58 Claims, 52 Drawing Sheets

U.S. PATENT DOCUMENTS

| | | | | |
|---|---|---|---|---|
| 4,772,286 A | 9/1988 | Goble et al. | | 623/13 |
| 4,843,112 A | 6/1989 | Gerhart et al. | | 523/114 |
| 4,851,005 A | 7/1989 | Hunt et al. | | 623/18 |
| 4,997,433 A | 3/1991 | Goble et al. | | 606/64 |
| 5,102,414 A | 4/1992 | Kirsch | | 606/73 |
| 5,163,960 A * | 11/1992 | Bonutti | | 128/898 |
| 5,192,282 A | 3/1993 | Draenert | | 606/65 |
| RE34,293 E | 6/1993 | Goble et al. | | |
| 5,224,946 A | 7/1993 | Hayhurst et al. | | 606/72 |
| 5,250,055 A | 10/1993 | Moore et al. | | 606/148 |
| 5,397,572 A | 3/1995 | Coombes et al. | | 424/426 |
| 5,411,523 A | 5/1995 | Goble | | 606/232 |
| 5,433,751 A | 7/1995 | Christel et al. | | 623/16 |
| 5,441,502 A | 8/1995 | Bartlett | | 606/104 |
| 5,482,717 A | 1/1996 | Fues et al. | | 424/426 |
| 5,486,593 A | 1/1996 | Tang et al. | | 528/370 |
| 5,501,687 A | 3/1996 | Willert et al. | | 606/94 |
| 5,514,137 A | 5/1996 | Coutts | | 606/62 |
| 5,593,425 A | 1/1997 | Bonutti et al. | | 606/232 |
| 5,597,383 A | 1/1997 | Carbone | | 623/23 |
| 5,620,700 A | 4/1997 | Berggren et al. | | 424/435 |
| 5,624,462 A | 4/1997 | Bonutti | | 623/16 |
| 5,641,502 A | 6/1997 | Skalla et al. | | 424/426 |
| 5,649,959 A | 7/1997 | Hannam et al. | | 606/213 |
| 5,665,110 A | 9/1997 | Chervitz et al. | | 606/232 |
| 5,665,111 A | 9/1997 | Ray et al. | | 606/232 |
| 5,679,723 A | 10/1997 | Cooper et al. | | 523/115 |
| 5,681,873 A | 10/1997 | Norton et al. | | 523/115 |
| 5,683,419 A | 11/1997 | Thal | | 606/232 |
| 5,725,541 A | 3/1998 | Anspach, III et al. | | 606/151 |
| 5,735,875 A | 4/1998 | Bonutti et al. | | 606/232 |
| 5,753,781 A | 5/1998 | Oxman et al. | | 525/415 |
| 5,824,333 A | 10/1998 | Scopelianos et al. | | 424/423 |
| 5,871,484 A | 2/1999 | Spievack et al. | | 606/60 |
| 5,893,856 A | 4/1999 | Jacob et al. | | 606/151 |
| 5,925,036 A | 7/1999 | Maxwell, III | | 606/13 |
| 5,928,239 A | 7/1999 | Mirza | | 606/79 |
| 5,928,267 A | 7/1999 | Bonutti et al. | | 606/216 |
| 5,935,131 A | 8/1999 | Bonutti | | 606/80 |
| 5,964,783 A | 10/1999 | Grafton et al. | | 606/232 |
| 5,976,127 A | 11/1999 | Lax | | 606/32 |
| 5,980,524 A | 11/1999 | Justin et al. | | 606/75 |
| 5,980,559 A | 11/1999 | Bonutti | | 606/232 |
| 5,993,451 A | 11/1999 | Burkhart | | 606/73 |
| 5,993,459 A | 11/1999 | Larsen et al. | | 606/104 |
| 6,007,567 A | 12/1999 | Bonutti | | 606/232 |
| 6,013,083 A | 1/2000 | Bennett | | 606/104 |
| 6,022,373 A | 2/2000 | Li | | 606/232 |
| 6,203,565 B1 * | 3/2001 | Bonutti et al. | | 606/232 |
| 6,464,713 B1 * | 10/2002 | Bonutti | | 606/232 |
| 6,610,079 B1 | 8/2003 | Li et al. | | 606/232 |
| 6,620,185 B1 * | 9/2003 | Harvie et al. | | 606/232 |

FOREIGN PATENT DOCUMENTS

| | | |
|---|---|---|
| DE | 3841 704 A1 | 6/1990 |
| DE | 195 45 612 A1 | 6/1997 |
| DE | 299 14 192 U 1 | 11/1999 |
| EP | 0 464 479 A1 | 1/1992 |
| EP | 0 496 140 A1 | 7/1992 |
| EP | 0 700 671 A1 | 3/1996 |
| EP | 0 714 666 A1 | 6/1996 |
| WO | WO 97/10743 | 3/1997 |
| WO | WO 97/13461 | 4/1997 |
| WO | WO 97/36555 | 10/1997 |
| WO | WO 98/26814 | 6/1998 |
| WO | WO 98/30141 | 7/1998 |
| WO | WO 02/00119 A2 | 1/2002 |

OTHER PUBLICATIONS

Appendix "Principles of Polymerization" pp. 96-99 by McGraw-Hill (9170).

Utah State University, Development of an Adhesive Suture Anchor, Fronk et al., pp. 1-98 (1998).

* cited by examiner

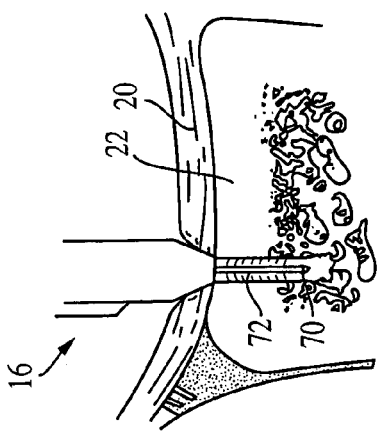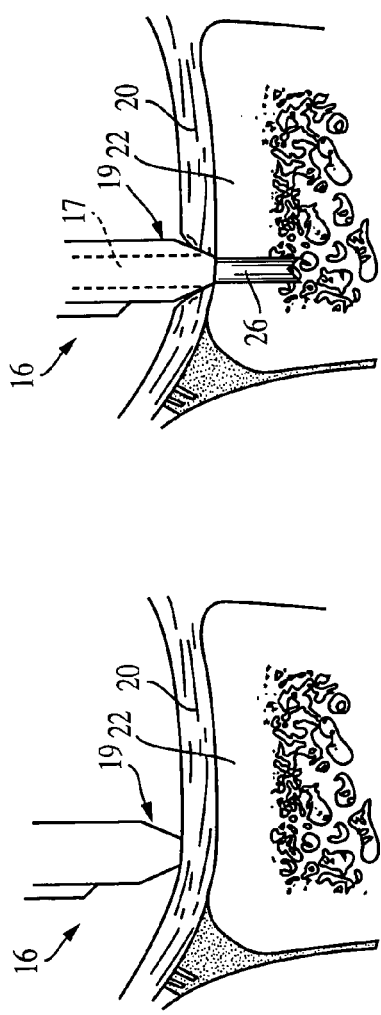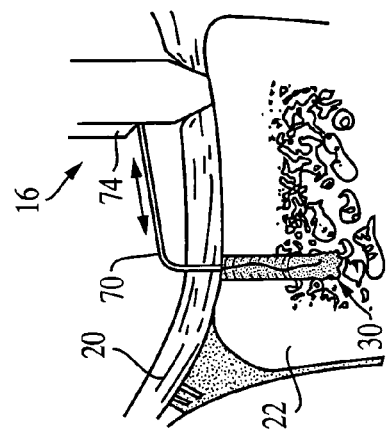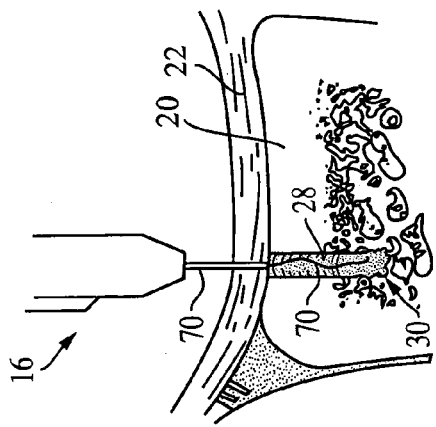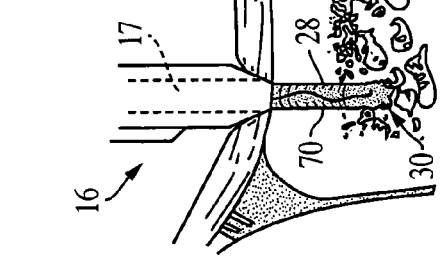

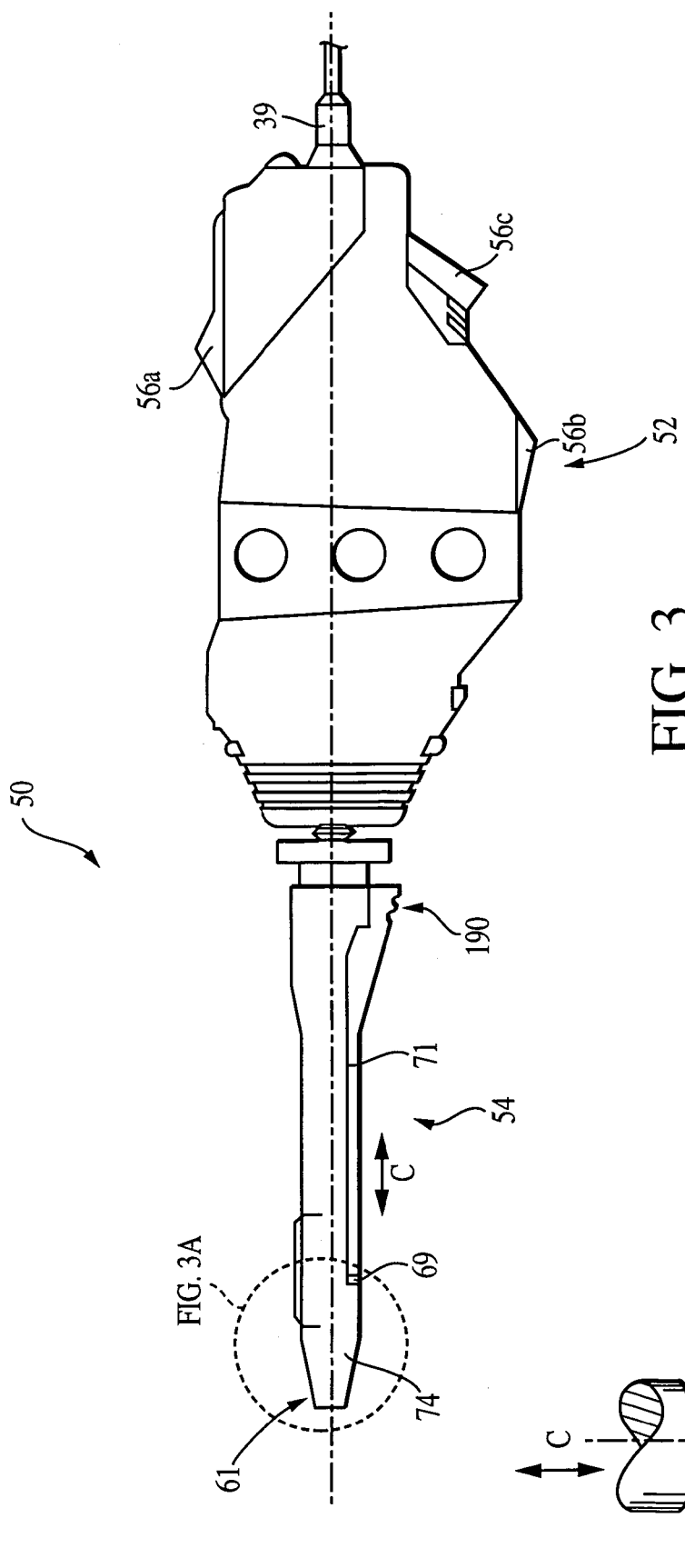

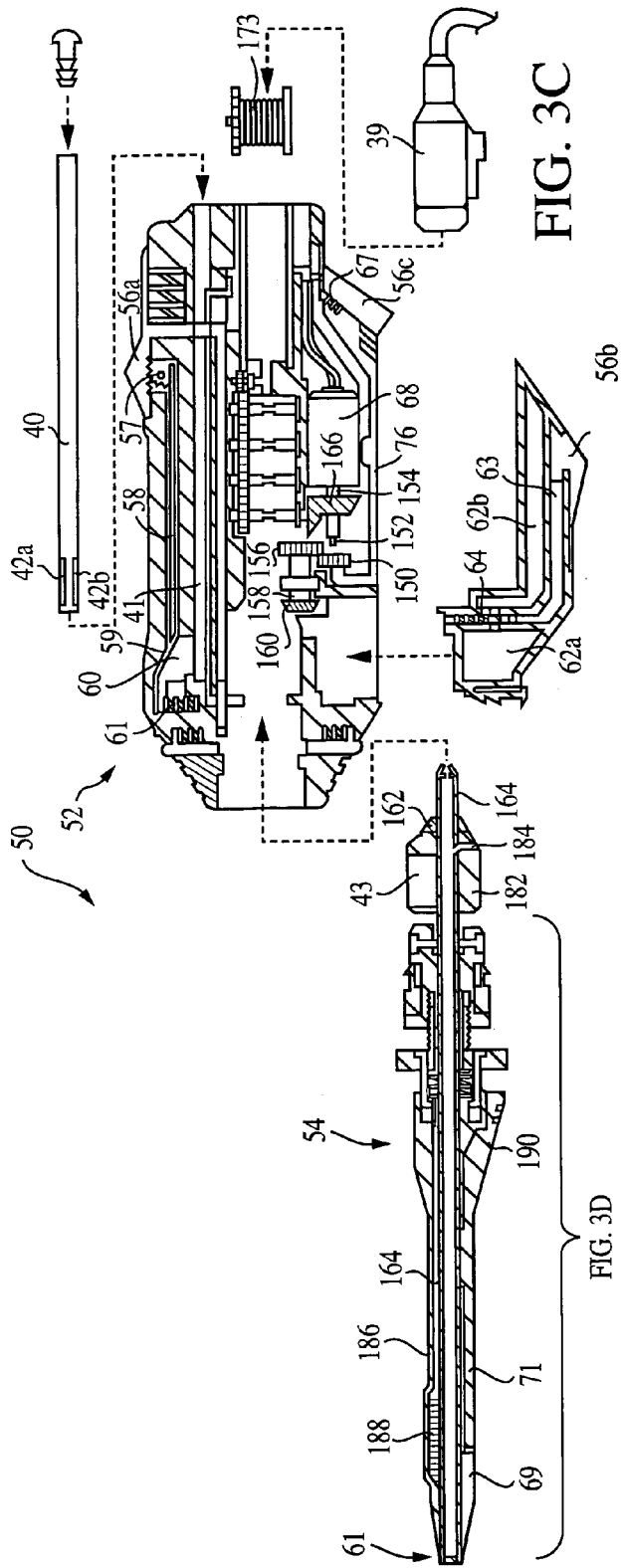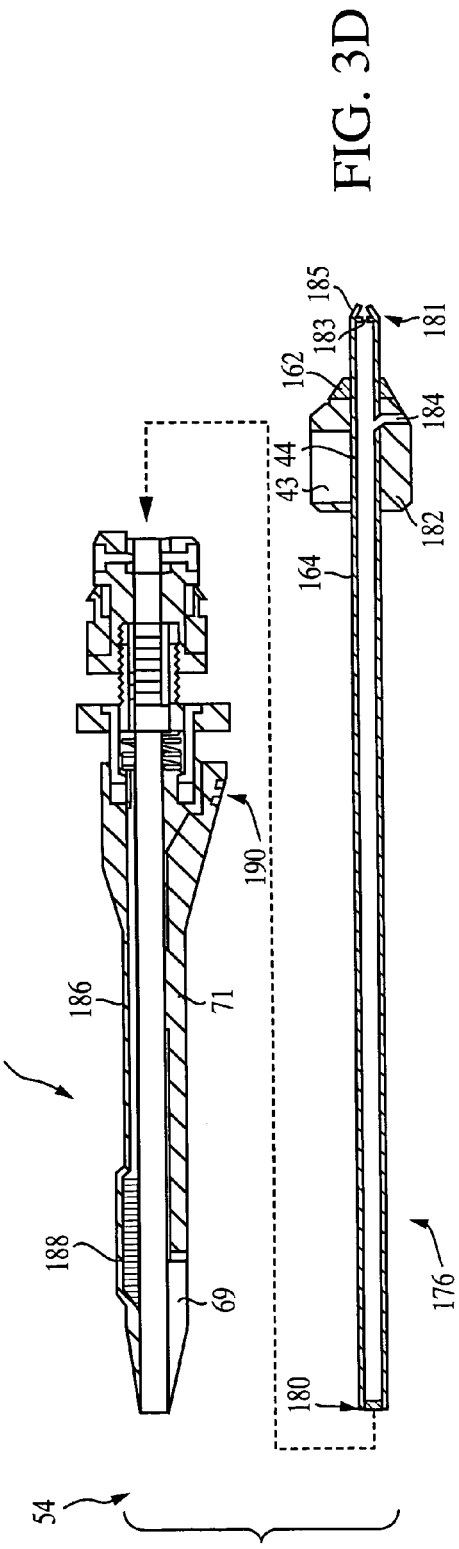

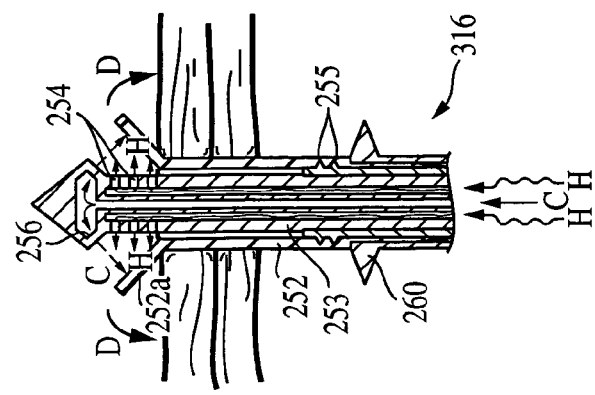
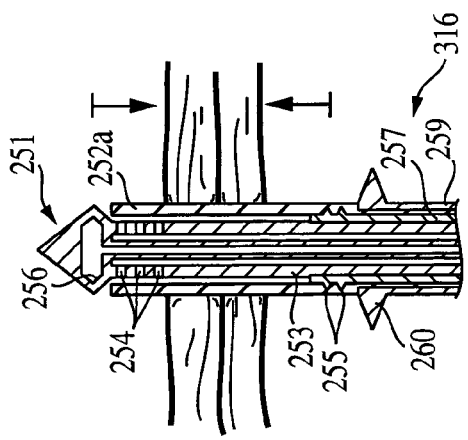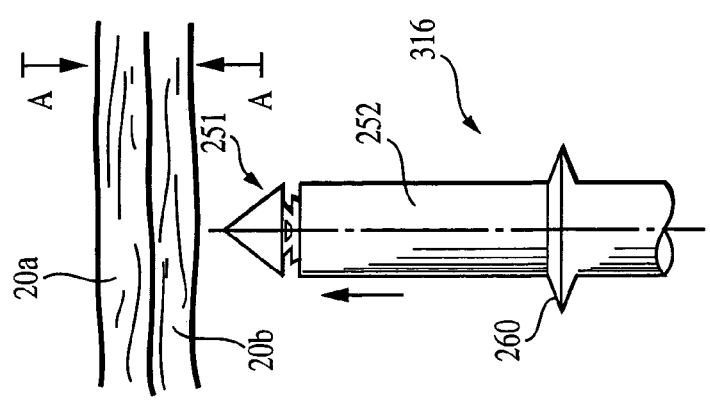
FIG. 8B
FIG. 8A
FIG. 8

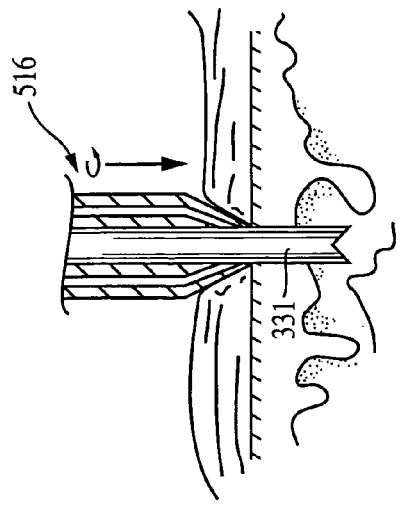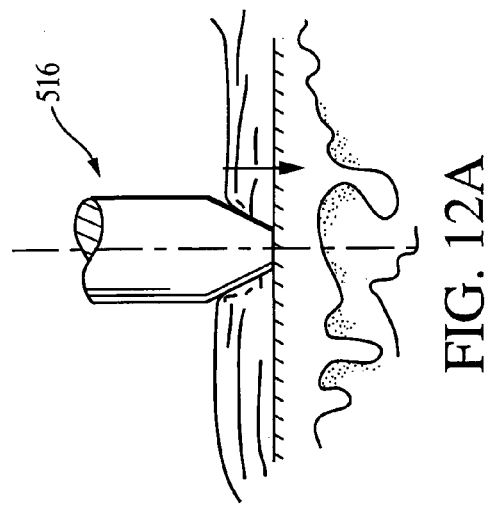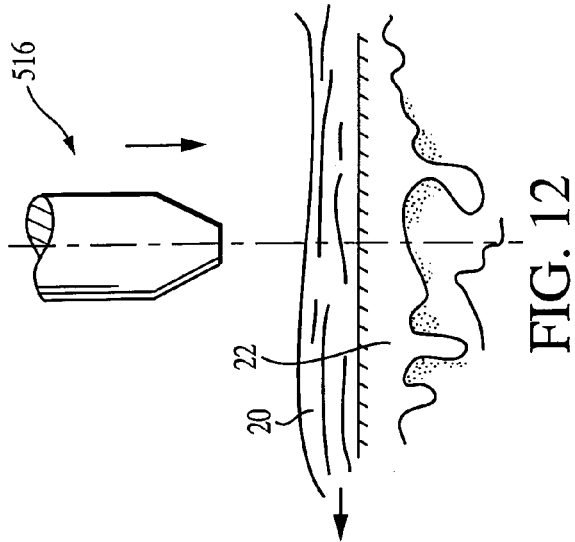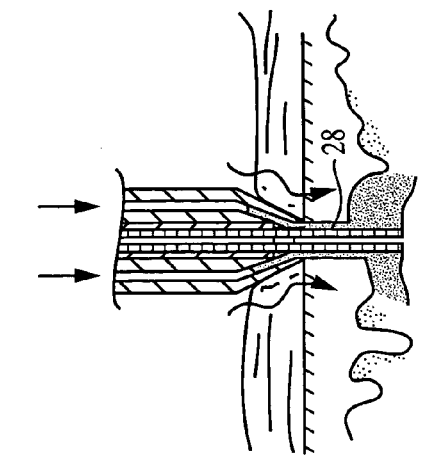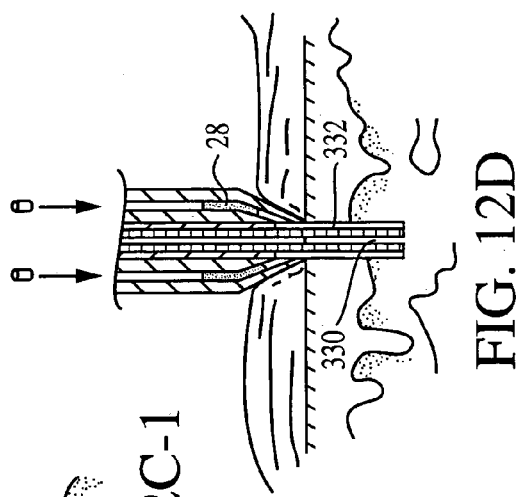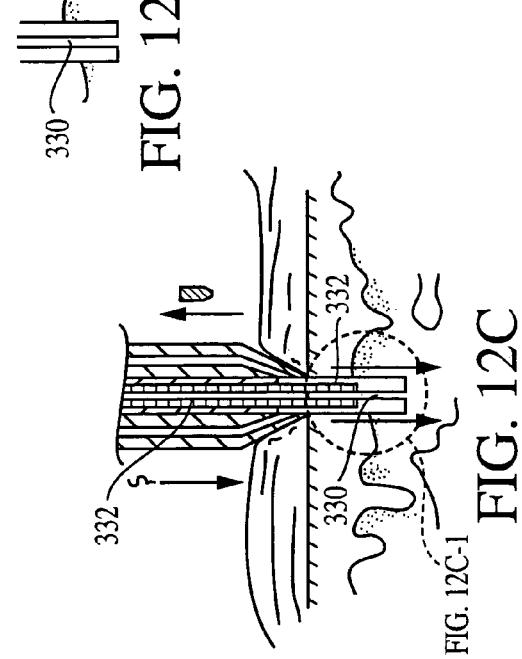

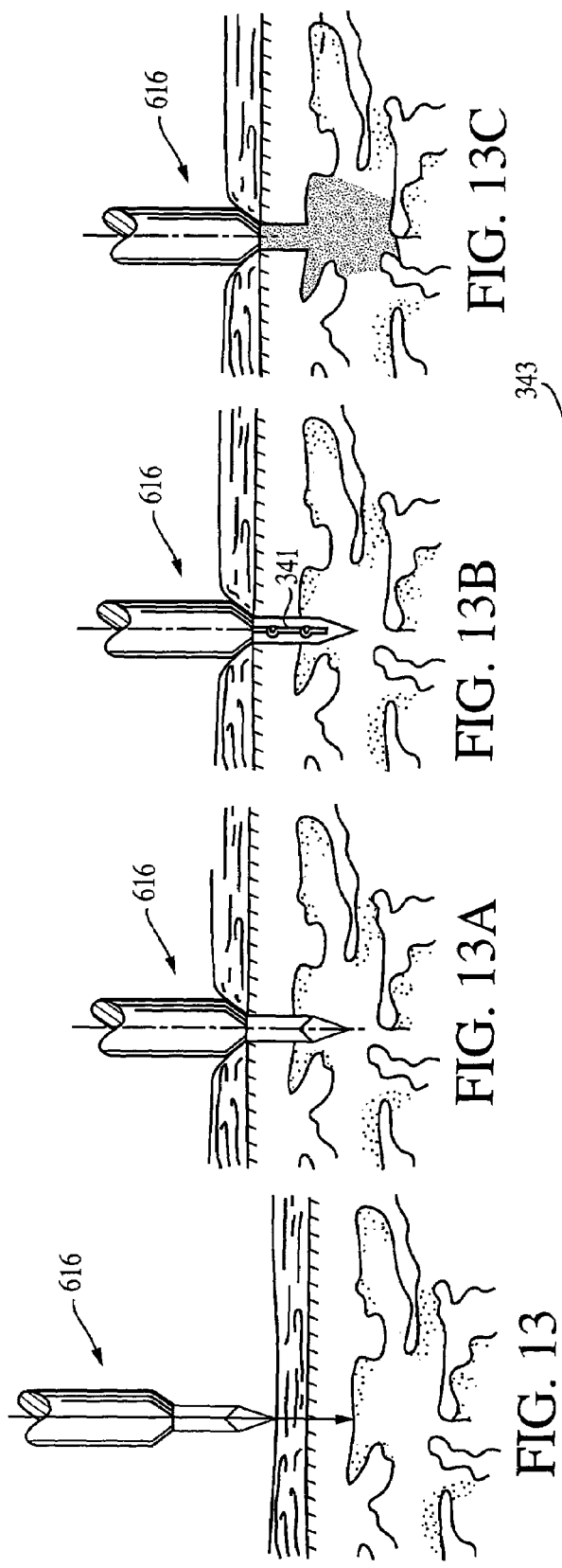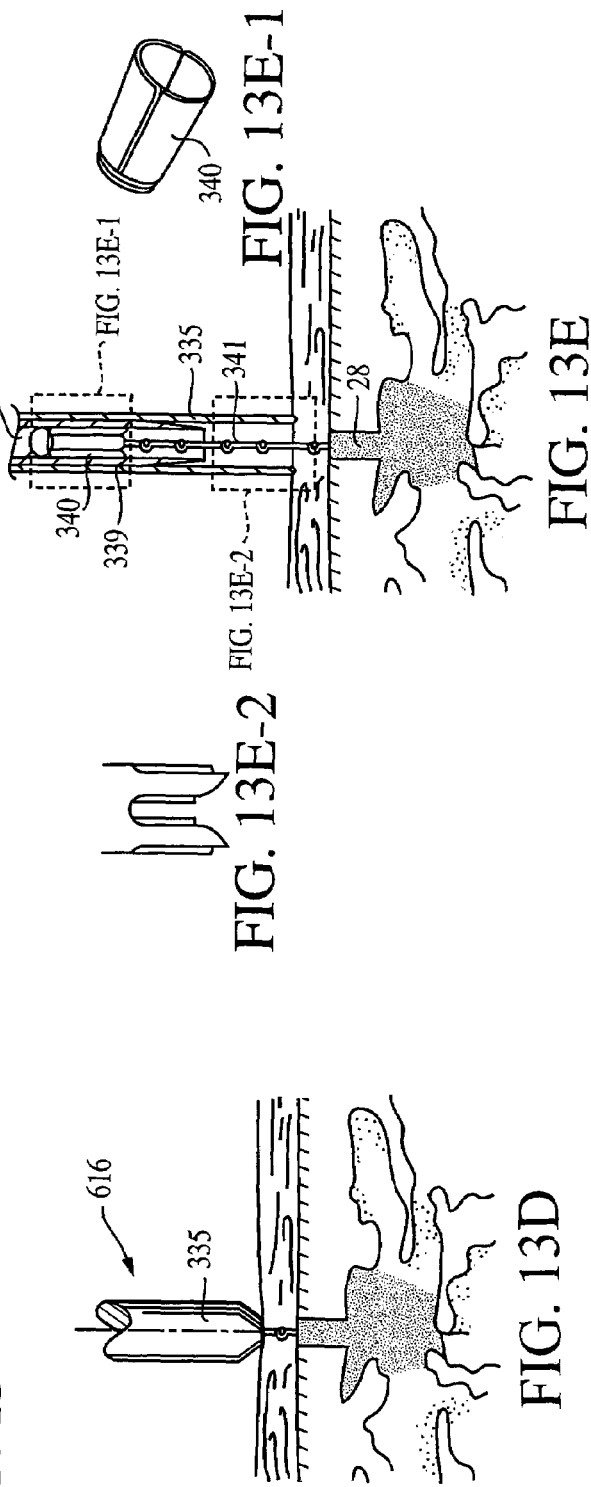

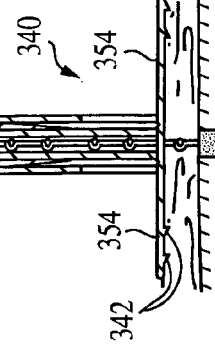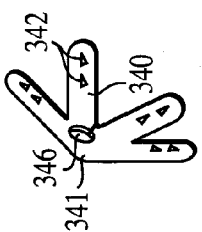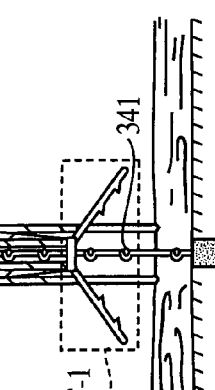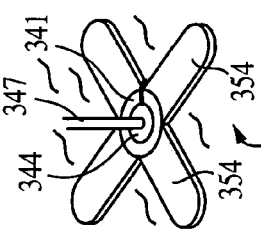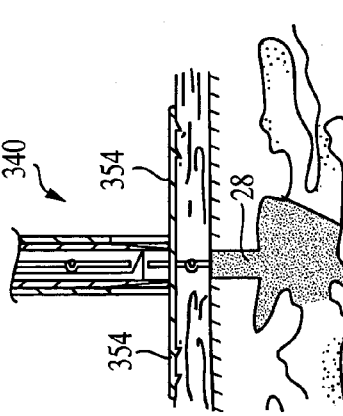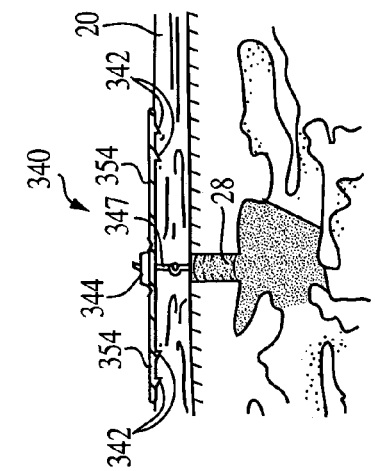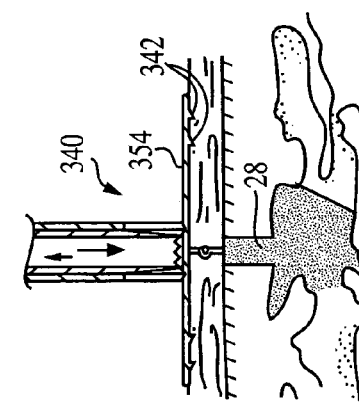

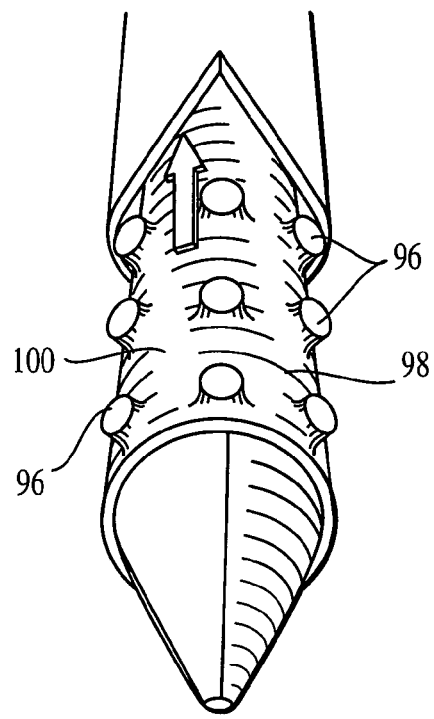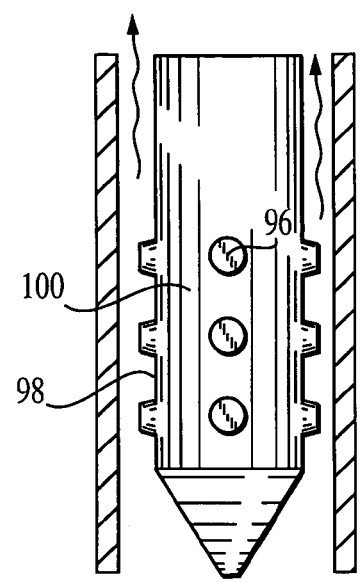
FIG. 15      FIG. 15A
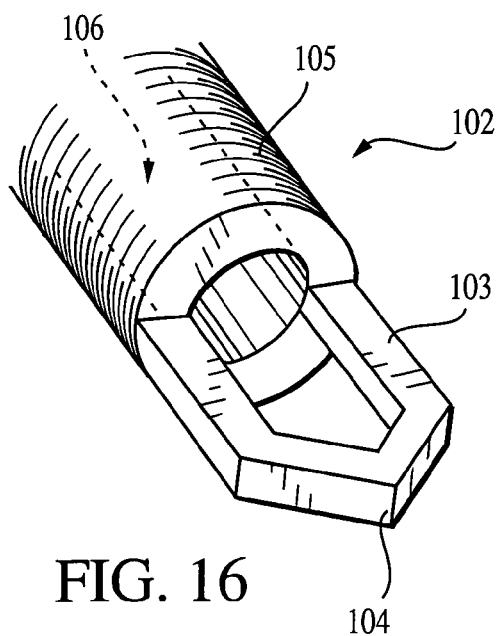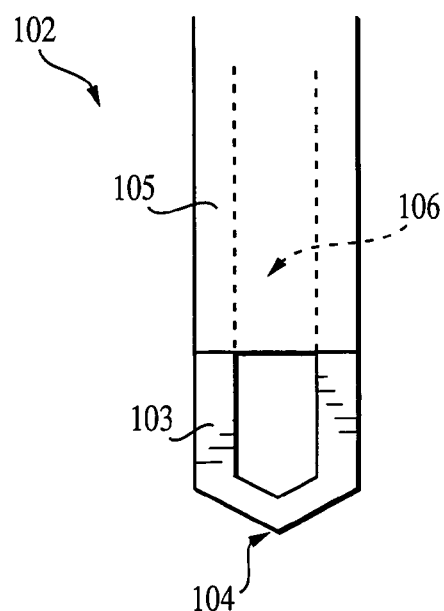
FIG. 16      FIG. 16A

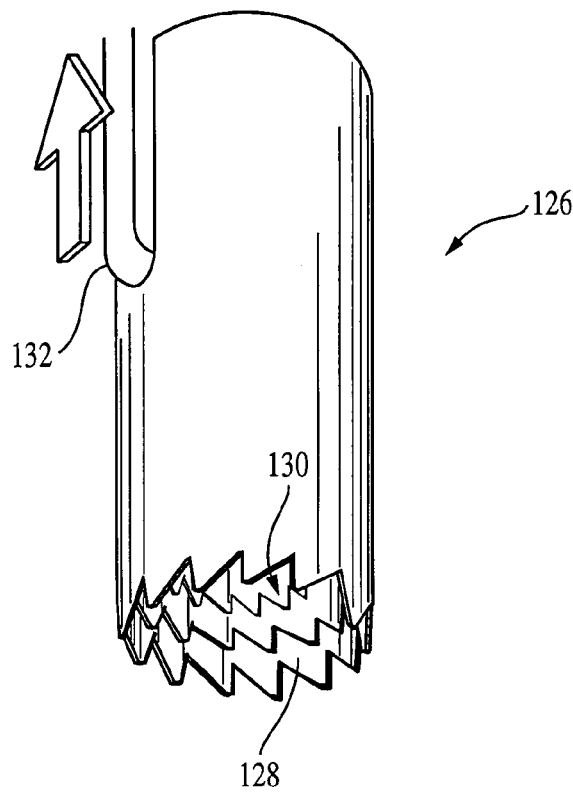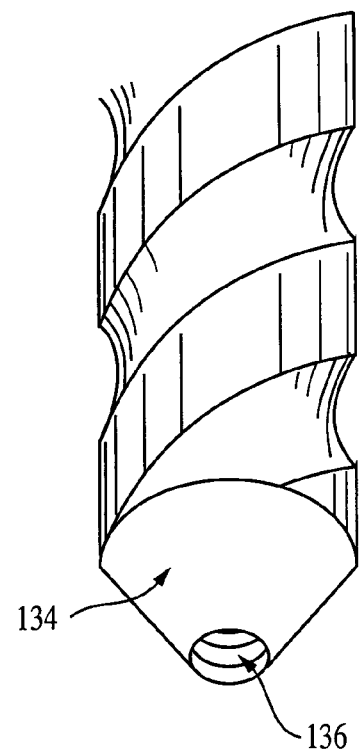
FIG. 19  FIG. 20
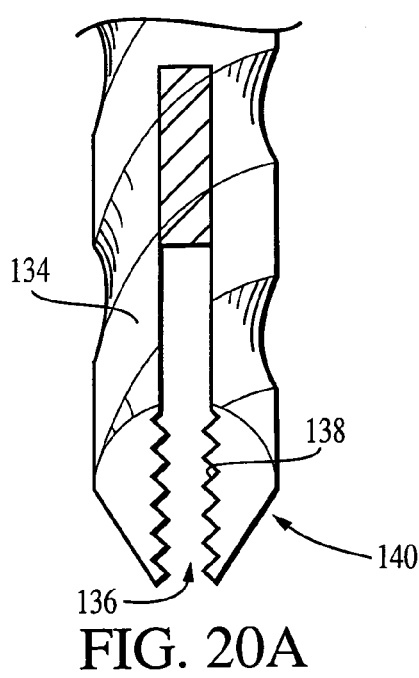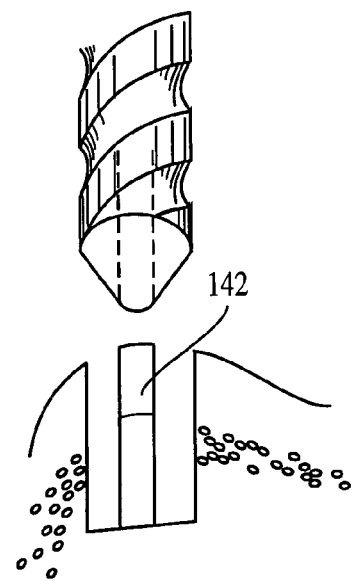
FIG. 20A  FIG. 20B

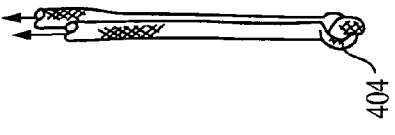
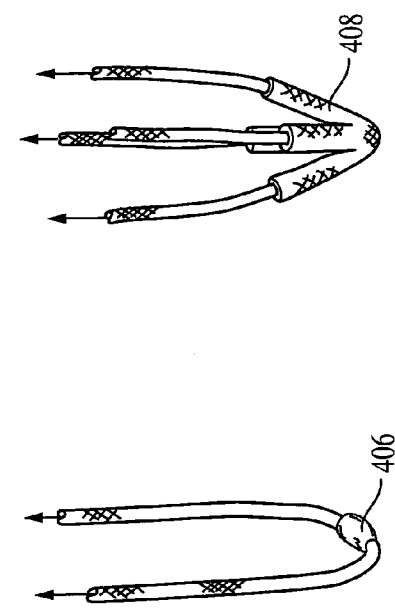
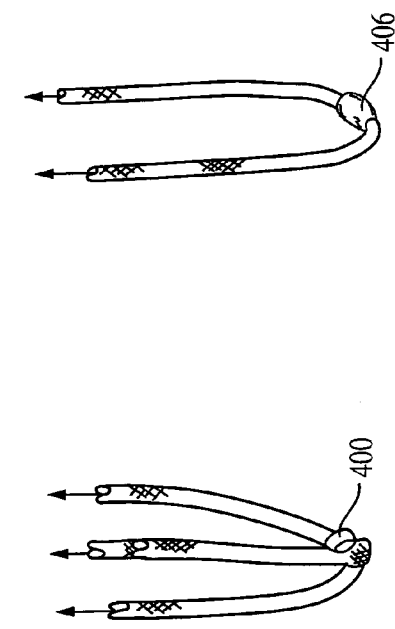
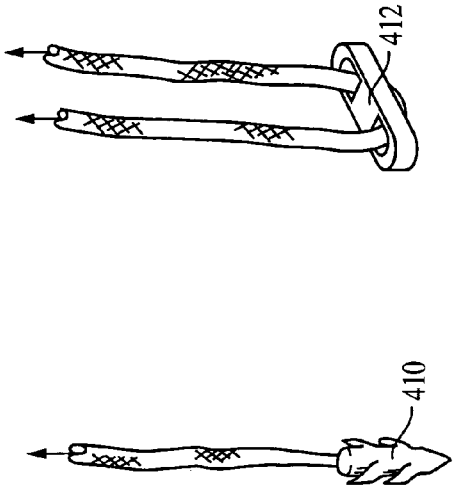
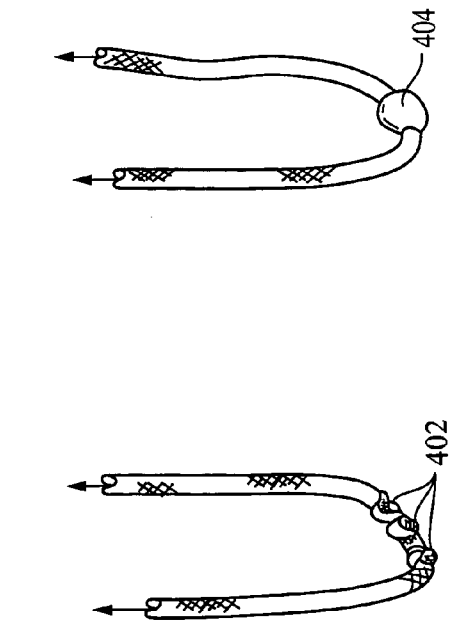

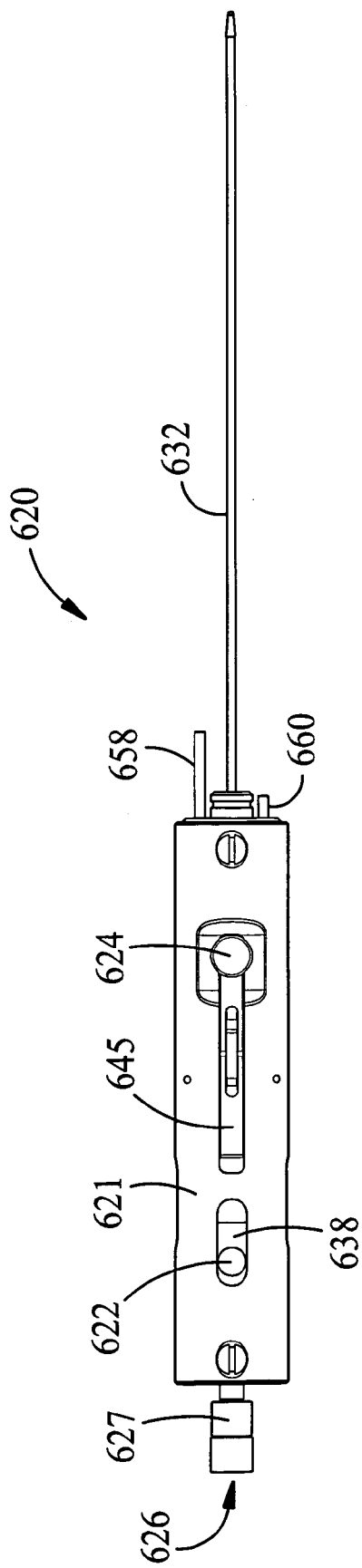
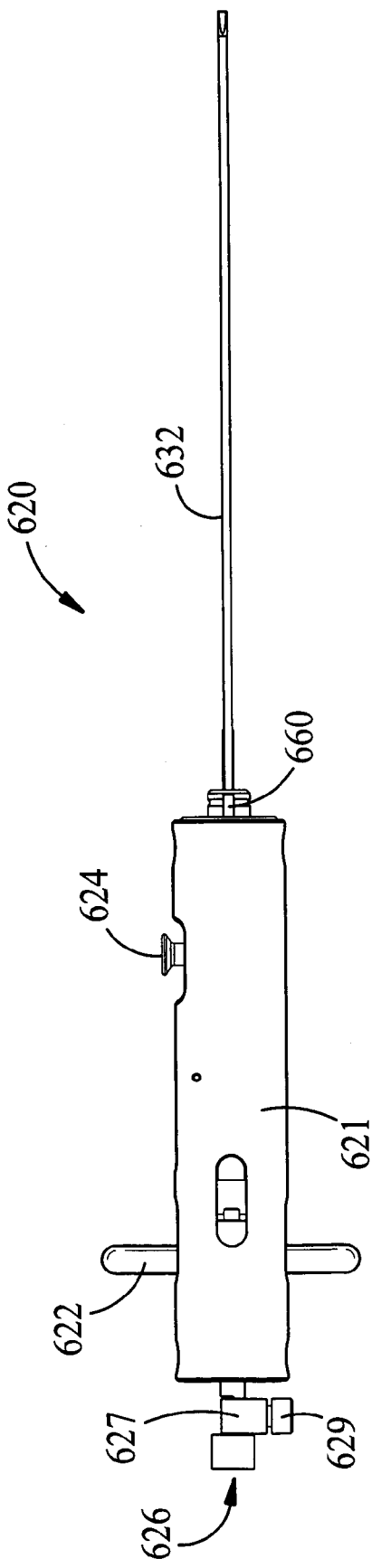
FIG. 35A
FIG. 35B

SURGICAL PROCEDURES AND INSTRUMENTS

CROSS-REFERENCE TO RELATED APPLICATIONS

"This application is a continuation-in-part application of and claims priority to U.S. application Ser. No. 09/604,387, filed on Jun. 27, 2000, now U.S. Pat. No. 6,620,185, the full disclosure of which is incorporated by reference herein."

TECHNICAL FIELD

This invention relates to surgical procedures and instruments.

BACKGROUND

Many surgical procedures involve fixing soft tissue to bone, particularly in the area of shoulder surgery, for example rotator cuff repairs and instability repair. Generally, in these procedures, the surgeon forms an incision to access the surgical site and then uses one of the following techniques to reattach the soft tissue.

In one technique, the surgeon drills bone tunnels through which a suture is passed. The suture is tied through the soft tissue, which is then reapproximated back to the bone.

In an alternative technique, the surgeon drills a cavity in the bone and inserts a bone anchor. Typically, the bone anchor is formed of metal, plastic or a resorbable material, and is held in place by wings or barbs that deploy outward, by threads or by radial expansion. The anchor includes an eyelet through which a suture is threaded. After placing the anchor, the surgeon ties the suture through the soft tissue, connecting it to the eyelet of the bone anchor and thus reapproximating the soft tissue to the bone.

If multiple sutures are needed to attach the soft tissue, either technique is repeated multiple times at different locations in the bone, with a separate knot tied at each location. It is generally not possible to connect a series of anchors formed using the techniques described above, due to the difficulty of tightening stitches between the anchors.

SUMMARY

According to one aspect of the invention, fixation of soft tissue to bone or to other soft tissue is performed using a flowable material, e.g., a polymer, in place of, or in addition to, a conventional bone anchor. Because the flowable material generally infiltrates the porous cancerous bone (also known as the "trabecular network"), the flowable material effectively forms an anchor that extends under the stronger cortical bone. As a result, an anchor formed in this manner typically exhibits a high pull-out strength. In some implementations, bone fragments are incorporated into the flowable material as an autologous filler, to enhance regrowth of bone into the material during natural healing.

Using preferred surgical procedures and instruments of the invention, fixation can be performed endoscopically, rather than in an open surgical procedure, resulting in less invasive treatment with minimal trauma to the patient. In some implementations piercing of soft tissue, drilling of a cavity, delivery of a suture and/or bone anchor (if used), and injection of the flowable material into the cavity are performed using a single endoscopic surgical instrument. In some preferred implementations knot-tying, which tends to require considerable skill and dexterity and is generally time-consuming, is not necessary. Thus, the surgical procedures of the invention are generally relatively quick, reducing trauma, and relatively easy to perform. In some implementations, the methods of the invention allow a series of connected, tensioned stitches to be made to fix a region of soft tissue to bone.

In implementations in which a conventional bone anchor is not used with the flowable material, certain risks that may be associated with such bone anchors are eliminated. For example, if a suture is used the suture does not run through an eyelet, and thus will not be microscopically damaged by friction between the suture and eyelet. Also, anchors formed using a flowable material do not rely heavily on the quality and density of the bone in which the anchor is placed, and thus a placement in compromised, low density bone may still exhibit good holding power.

The invention also features surgical procedures involving endoscopic application of polymers for other purposes, e.g., to repair a bone defect, to fill holes that are left when bone plugs are harvested, to repair osteochondritis dessicans injuries, for repair or revision of ACL grafts that exhibit micromovement, for spine fusion, for meniscal repair, and to repair bone fractures. The use of endoscopic devices and techniques significantly reduces invasiveness, generally resulting in less trauma and quicker recovery.

In one aspect, the invention features a method of securing a fixation device within an opening in a tissue, including (a) delivering a material in a flowable state to the opening, and (b) changing the state of the material so that the material forms an interference fit that secures the fixation device in the opening. The fixation device may also be secured in the opening by other, supplemental means, e.g., threaded engagement, but at least a portion of the securing is provided by the interference fit.

Implementations of this aspect of the invention may include one or more of the following features. The tissue includes bone and/or soft tissue. The fixation device is selected from the group consisting of suture, anchors, and screws. The changing step includes allowing the material to at least partially harden. The changing step includes at least partially cross-linking the material. The material includes a polymer, e.g., a thermoplastic polymer. The material includes a hydrogel. The method further includes using the fixation device to secure a second tissue to the tissue having the opening. The tissue having the opening includes bone and the second tissue includes soft tissue. The method further includes, prior to delivery of the material, piercing the soft tissue; forming the opening in an underlying area of the bone; and delivering the fixation device through the pierced tissue; wherein the fixation device is constructed to hold the soft tissue in place against the bone. The fixation device includes a suture. The suture includes a region of increased surface area to enhance anchoring, e.g., a knot, barb, braided area, ball or shaped element. All of the steps of the method are performed endoscopically, for example the steps are performed using a single endoscopic surgical tool having a plurality of attachments, and the tool is not removed from the patient until after the steps are completed. The method further includes incorporating bone fragments, e.g., fragments generated during the forming step, into the material during or prior to the delivering step. The method further includes causing the material to infiltrate the trabecular network. The material includes an osteoconductive filler. The opening is formed using micro-tooling. The opening has a diameter of less than about 3 mm. The forming step includes forming the opening using a consumable cutting tool, and the delivering step includes causing the cutting tool to melt in response to frictional heat generated during the forming step. The forming step includes forming the opening with a cutting tool having a detachable portion, and the method further includes detaching the detachable portion in the opening after the forming step is completed, to serve as the fixation device.

In another aspect, the invention features a method of anchoring soft tissue to bone including (a) piercing the soft tissue; (b) forming an opening in an underlying area of the bone; (c) delivering a material, in a flowable state, to the opening; and (d) molding a portion of the material that is not in the opening to form a fixation device constructed to hold the soft tissue in place against the bone after the material changes state to a relatively less flowable state.

Implementations of this aspect of the invention may include one or more of the following features. The molding step includes forming a portion of the material into a shape that extends radially over a portion of the soft tissue surrounding the opening. The forming step includes drilling or abrading. All of the steps are performed endoscopically. The method further includes incorporating bone fragments generated during the forming step into the material during or prior to the delivering step. The material includes an osteoconductive filler. The method further includes causing the material to infiltrate the trabecular network The opening has a diameter of less than about 3 mm, more preferably from about 0.1 to 6.0mm. The forming step is performed using micro-tooling. The material includes a polymer. The formed portion extending radially over the soft tissue is coextensive with the material in the opening, defining a bolt-like anchor.

In a further aspect, the invention features a method of fixing soft tissue to bone including (a) at a first location, piercing through the soft tissue; (b) forming an opening in the bone underlying the soft tissue; (c) delivering a fixation device through the pierced tissue to the opening; (d) delivering a material, in a flowable state, to the opening; and (e) causing the material to change state, to a relatively less flowable state, to anchor at least a portion of the fixation device in the opening. The fixation device is selected from the group consisting of suture, anchors and screws. The method further includes (f) drawing the suture across the soft tissue to a second location, and (g) repeating steps (a)-(e) at the second location to form a stitch with the suture between the first and second locations, the stitch securing the soft tissue to the bone. The method further includes gripping the soft tissue to hold it in place against the bone. The method further includes (h) cutting the suture. Steps (a) and (h) are performed with a single tool. Steps (a)-(d) are performed endoscopically. The method further includes repeating steps (f)-(g) at subsequent locations to form a line of connected stitches. Steps (c) and (d) are performed substantially simultaneously, or, alternatively, step (c) is performed prior to step (d). The method further includes delivering the suture as a continuous length from a supply of suture material. The material is provided in the form of a pellet, powder, chips, flakes or rod, and the method further includes melting the material prior to delivery. The method further includes incorporating bone fragments generated during the forming step into the material during or prior to the delivering step. The method further includes incorporating an osteoconductive filler into the material. The method further includes causing the material, in its flowable state, to infiltrate the trabecular network The forming step includes forming a opening having a diameter of less than about 3 mm. The opening has a diameter of from about 0.1 to 6.0 mm. The forming step includes drilling or abrading. The forming step is performed using micro-tooling. The forming step is performed in the bone of a human shoulder.

In yet another aspect, the invention features a surgical instrument for tissue fixation including (a) a handpiece constructed to be held by a surgeon during a fixation procedure; and (b) a fixation instrument, mounted on the handpiece and including (i) a piercing element constructed to pierce through the tissue and form an opening therein; and (ii) a lumen for delivery of a material, in a flowable state, and a fixation device to the opening.

Implementations of this aspect of the invention may include one or more of the following features. The fixation device includes a suture. The surgical instrument further includes a suture feed mechanism constructed to deliver the suture through the lumen to the opening. The surgical instrument is constructed for endoscopic use. The surgical instrument further includes a heating element for heating the material to a molten state. The heating element is mounted on the fixation instrument. The suture feed mechanism includes a movable needle. The surgical instrument further includes a probe constructed to tighten a stitch formed with the suture, e.g., mounted on an external surface of the fixation instrument. The probe is constructed to be manually actuated by a surgeon during an endoscopic procedure. The handpiece includes a reservoir for receiving the material in solid form. The reservoir is constructed to receive a supply of pellets of the material and the handpiece further comprises a mechanism for delivering the pellets from the reservoir to the lumen. Alternatively, the reservoir is constructed to receive a supply of powdered material and the handpiece further comprises a mechanism for delivering a predetermined dose of powdered material from the reservoir to the lumen. The fixation instrument is detachable from the handpiece. The surgical instrument further includes a mixing device constructed to mix bone fragments and debris generated during opening forming into the material prior to delivery to the opening. The surgical element further includes a drive mechanism constructed to drive the piercing element and, if it is included, the suture feed mechanism. The drive mechanism is disposed in the handpiece. The surgical instrument further includes a clutch mechanism constructed to allow a surgeon to selectively engage and disengage the drive of the piercing element and the drive of the suture feed mechanism. The handpiece is constructed to receive attachments other than the fixation instrument. The piercing element is constructed to cut the suture. The fixation instrument is constructed to perform a complete fixation procedure without removing the fixation instrument from the surgical site.

In another aspect, the invention features a surgical method including (a) forming an opening in bone of a patient; (b) incorporating bone fragments generated during the forming step into a polymer as an autologous filler to form a bone/polymer blend; and (c) delivering the bone/polymer blend, in a flowable state, to the patient; wherein steps (a)-(c) are performed endoscopically. In some implementations, the bone/polymer blend is delivered to the opening.

In yet another aspect, the invention features a method of securing a first layer of soft tissue to a second layer of soft tissue including (a) forming an opening extending through both layers of soft tissue; (b) delivering a material, in a flowable state, through the opening so that the flowable material extends beyond the soft tissue at each end of the opening; and (c) causing the material to change state, to a relatively less flowable state, forming an anchor to secure the two layers of soft tissue together.

In a further aspect, the invention features a method of securing a first layer of soft tissue to a second layer of soft tissue including (a) forming an opening extending through both layers of soft tissue; (b) delivering a thermoplastic member to the opening, so that a portion of the member extends beyond the soft tissue at each end of the opening; (c) softening the extending portions of the member; and (d) forming each of the softened extending portions so that each extends radially over a portion of the soft tissue to secure the two layers of soft tissue together.

In some implementations, the member includes a hollow tube and the forming step results in a rivet-like anchor.

In another aspect, the invention features a method of securing two tissues together including (a) forming an opening extending through the two tissues, (b) delivering a material, in a flowable state, to the opening, and (c) causing the material to change state, to a relatively less flowable state; wherein the material forms an anchor that secures the two tissues together. In some implementations, the anchor is a bolt-like anchor.

In a further aspect, the invention features an endoscopic instrument for securing two tissues together including (a) a piercing device constructed to form an opening extending through the two tissues; and (b) a delivery device constructed to deliver a material, in a flowable state, and a fixation device, to the opening.

In another aspect, the invention features surgical instruments constructed to perform the steps of the methods described above. Preferred instruments are constructed to perform all steps of the methods endoscopically.

The invention also features, in another aspect, a surgical instrument for tissue fixation including: (a) a handpiece constructed to be held by a surgeon during a fixation procedure; (b) a cannulated tube defining a lumen, mounted on the handpiece; (c) a delivery device, constructed to be mounted on the handpiece, for delivering a flowable material through the lumen to an opening in bone; and (d) a suture control device for delivering a suture material from a supply to a distal end of the cannulated tube.

Some implementations include one or more of the following features. The delivery device includes a heating element for heating said material to a flowable state. The delivery device further includes a reservoir containing a supply of the flowable material, and the heating element is constructed to deliver heat to at least a portion of the reservoir. The heating element is positioned adjacent at least a portion of the reservoir. The delivery device further includes a delivery tube in communication with the reservoir, the delivery tube being constructed to be disposed within the cannulated tube when the delivery device is mounted on the handpiece. The heating element is constructed to deliver heat to the delivery tube. The heating element includes a terminal portion, adjacent a distal end of the delivery tube, which can be turned off while heat is being delivered to the remainder of the heating element, so as to allow the flowable material at the distal end of the delivery tube to solidify and shut off flow from the delivery tube. The delivery device comprises an elongated nozzle having a distal end constructed to receive a portion of suture, and a mechanism constructed to extend the nozzle out of the distal end of the cannulated tube to push the portion of the suture into the opening and to retract the nozzle after delivery of the suture. The elongated nozzle is cannulated to provide a path for delivery of the flowable material to the opening. Prior to initial use of the surgical instrument, the delivery tube contains a supply of the flowable material. The delivery device comprises a mechanism for metering a predetermined dose of the flowable material.

Alternatively, the heating element includes an elongated member having a tip constructed to deliver a polymer pellet through the lumen to the opening, the tip having an area to which heat can be delivered to melt the pellet. The delivery device further includes a plunger tube constructed to be disposed within the cannulated tube when the delivery device is mounted on the handpiece, and the elongated member is constructed to be inserted through the plunger tube. The delivery device further includes a mechanism for moving said plunger tube between an extended position and a retracted position. The delivery device further includes a mechanism for moving said elongated member between an extended position and a retracted position. The mechanisms for moving the plunger tube and elongated member can be simultaneously activated by the surgeon, and operate counter to one another. The heating element comprises metal tube and, within the tube, an insulated current-carrying wire, the wire and tube being joined at a distal end to form a circuit, and the metal tube including a first portion having a relatively low resistance and a second, distal portion having a relatively higher resistance. The delivery device includes an elongated plunger constructed to be extended through the cannulated tube into the opening to compact the flowable material. The elongated plunger defines a lumen through which a heating element is inserted into the opening.

The heating element is constructed to melt the material prior to delivery to the opening. The heating element is constructed to melt the material after delivery to the opening. The delivery device is detachable from said handpiece. The suture control device is constructed to control the tension applied to a free end of the suture. The supply of suture material is disposed within the handpiece. The suture control device comprises nested tubes, surrounding the cannulated tube, which define a path for the suture from the supply to the distal end. The nested tubes include an outer tube, and a middle tube disposed between the outer tube and the cannulated tube, and the path is defined by a groove extending longitudinally along the length of the middle tube. The suture control device includes a suture lock, actuatable by the surgeon, to hold the suture in place at the distal end of the cannulated tube. The suture control device comprises a suture displacement device for controlling the position of the suture at the distal end. The suture control device comprises a tensioning device for maintaining tension on the suture. The tensioning device is constructed to tighten a stitch formed with the suture. The tensioning device includes a spring mechanism. The tensioning device is constructed to be manually actuated by the surgeon.

The surgical instrument is constructed to allow the surgeon to perform a complete fixation procedure at a surgical site without removing the cannulated tube from the surgical site. The surgical instrument is constructed for use in an endoscopic procedure.

In another aspect, the invention features a surgical instrument for tissue fixation including (a) a handpiece constructed to be held by a surgeon during a fixation procedure; (b) a cannulated tube defining a lumen, mounted on the handpiece; and (c) a delivery device for delivering a flowable material through the lumen to an opening in bone, the delivery device comprising a heating element for heating said material to a flowable state.

The heating element is configured to heat the material within the opening, and the flowable material may be delivered through the lumen in solid form. The delivery device may be configured to deliver a metered dose of the flowable material.

In a further aspect, the invention features a surgical instrument for tissue fixation including: (a) a handpiece constructed to be held by a surgeon during a fixation procedure; (b) a cannulated tube, mounted on the handpiece; and (c) a suture control device for delivering a suture material from a supply within the handpiece to a distal end of the cannulated tube.

The invention also features a method of securing a tissue to bone, including: (a) forming an opening in the bone at a first location; (b) delivering a flowable material and a suture to said opening; (c) allowing the flowable material to at least partially solidify and secure a portion of the suture in the opening; (d) drawing a free portion of the suture that extends from the secured portion across the soft tissue to a second location; (e) forming a second opening in the bone at the second location; (f) delivering a flowable material and a portion of the suture to said second opening; and (g) allowing the flowable material to at least partially solidify, the suture defining a stitch between the first and second locations.

In yet another aspect, the invention features a method of fixing soft tissue to bone comprising: (a) at a first location, piercing through the soft tissue; (b) forming an opening in the bone underlying the soft tissue; (c) delivering a fixation device through the pierced tissue to the opening; (d) delivering a material, in a non-liquid state, to the vicinity of the opening; and (e) after delivery, liquifying and subsequently resolidifying the material to anchor at least a portion of the fixation device in the opening.

Other features and advantages of the invention will be apparent from the description and drawings, and from the claims.

DESCRIPTION OF DRAWINGS

FIGS. 3–3E are views of a surgical instrument suitable for performing the method shown in FIGS. 2–2K. FIG. 3 is a side view of the surgical instrument. FIG. 3A is a highly enlarged detail perspective view of area A of FIG. 3. FIG. 3C is an exploded cross-sectional view of the surgical instrument of FIG. 3. FIG. 3D is an exploded view of area D of FIG. 3C. FIG. 3E is an exploded view showing an enlarged cross-sectional view of the polymer cartridge of the instrument.

FIGS. 13–13J are diagrammatic views of yet another alternative procedure for fixing soft tissue to bone.

FIGS. 15 and 15A are perspective and side views, respectively, of an alternative cutting tool.

FIGS. 16 and 16A are perspective and side views, respectively, of an alternative cutting tool.

FIG. 19 is a perspective view of an alternative cutting tool.

FIGS. 20 and 20A are perspective and cross-sectional views, respectively, of an alternative cutting tool. FIG. 20B is a diagrammatic cross-sectional view showing the cutting tool of FIGS. 20–20A in use.

FIGS. 21–21G are diagrammatic views of various types of augmented sutures.

FIGS. 30 and 30A are schematic perspective views, in partial cross-section, of the distal end of the polymer delivery assembly, showing the use of a nozzle to deploy a suture from the suture control assembly into a hole in bone and to inject a polymer into the hole. The suture control assembly, which would normally surround the polymer delivery assembly when the surgical instrument is in use, is omitted here for clarity.

FIGS. 31 and 31A are highly enlarged perspective views of the distal end of the nozzle and inner portion of the suture control assembly, in the positions shown in FIGS. 29 and 29A.

FIGS. 35A and 35B are, respectively, top and side views of the polymer delivery assembly of FIG. 35.

DETAILED DESCRIPTION

Figure 1:
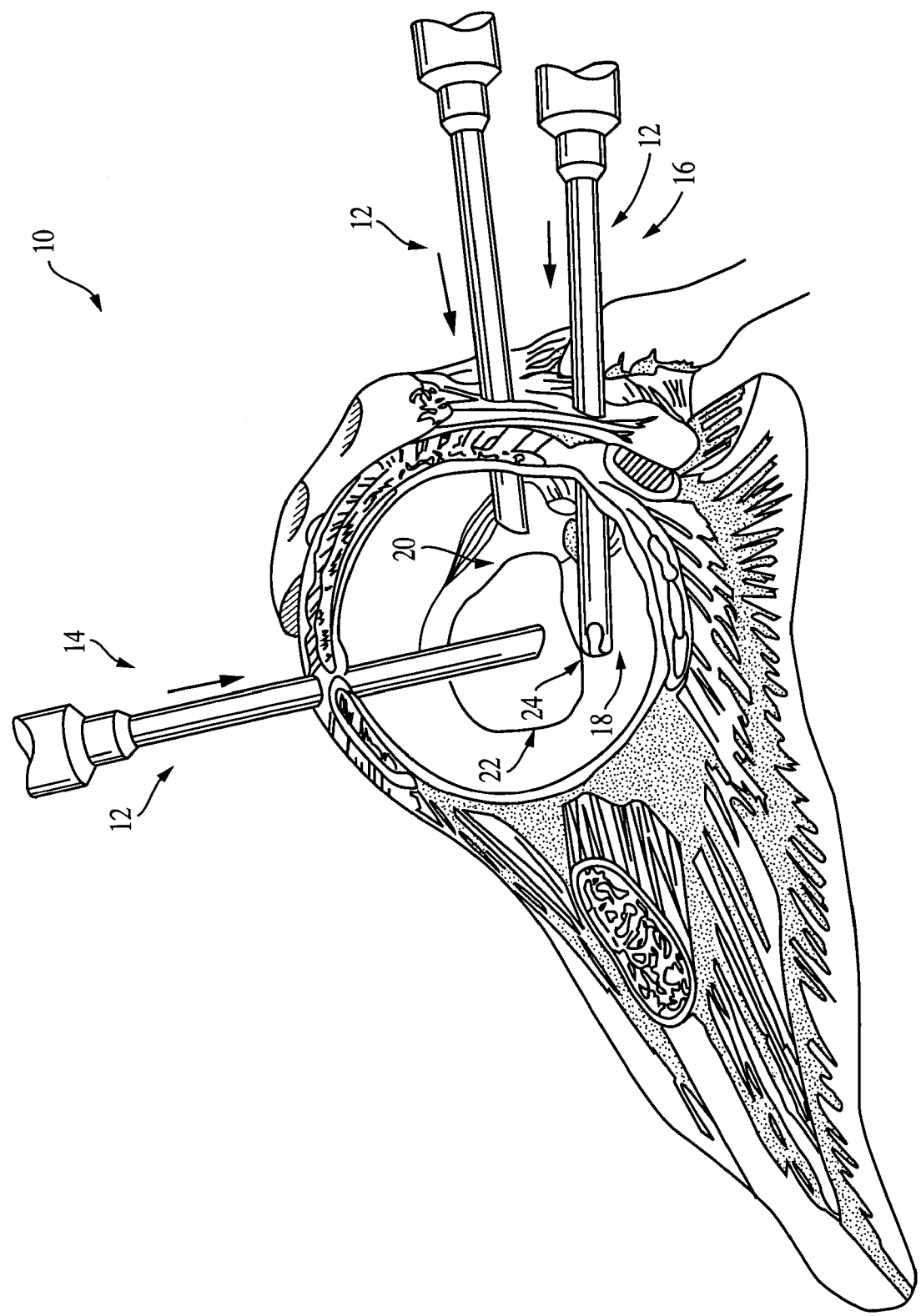
FIG. 1 is a diagrammatic perspective view of the surgical environment of an endoscopic procedure according to one embodiment of the invention.

Referring to FIG. 1, a surgical site 10 includes a number of portals 12, through which endoscopic devices can be inserted. The surgeon can view the surgical site using an arthroscope 14, while placing a polymeric anchor, as will be discussed in detail below, using a surgical instrument 16. Surgical instrument 16 generally depicts an instrument for placing a polymeric anchor. Examples of particular instruments that are suitable for use in the various methods of the invention will be discussed in further detail below. In the initial step shown in FIG. 1, the surgeon is using a shaver 18 to remove a portion of soft tissue 20, expose the surface 24 of bone 22 and create a bleeding bone bed, in preparation for the surgical procedures described below. While shaver 18 is shown as a separate instrument in FIG. 1, it may instead be integrated with surgical instrument 16.

Figure 2F:
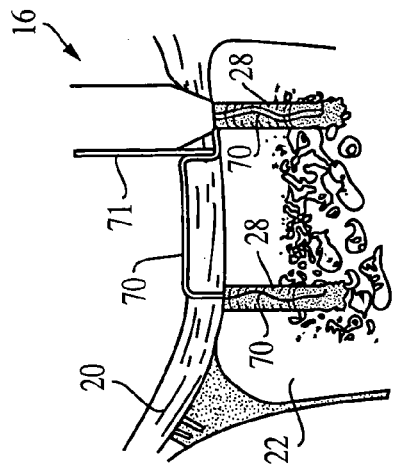
FIGS. 2–2K are diagrammatic views of a procedure for forming a series of polymeric anchors connected by stitching.
Figure 2G:
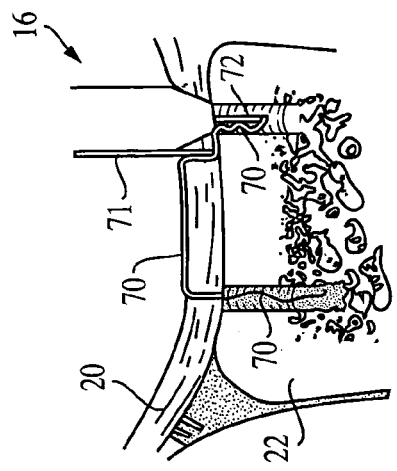
Figure 2H:
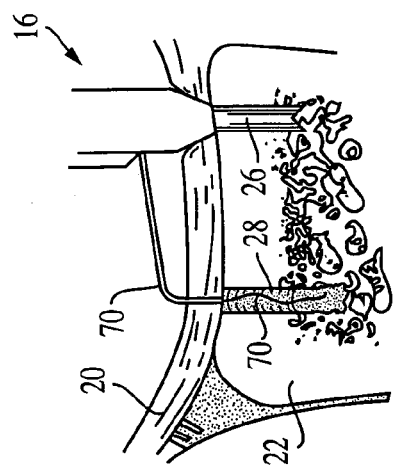
Figure 2I:
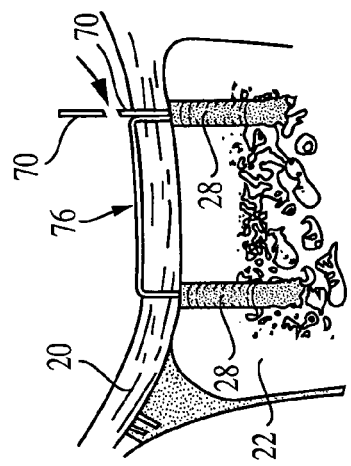
Figure 2J:
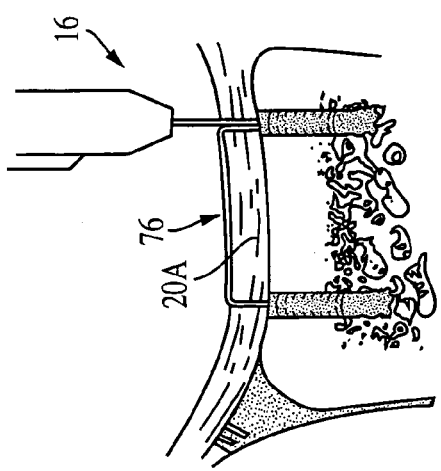
Figure 2K:
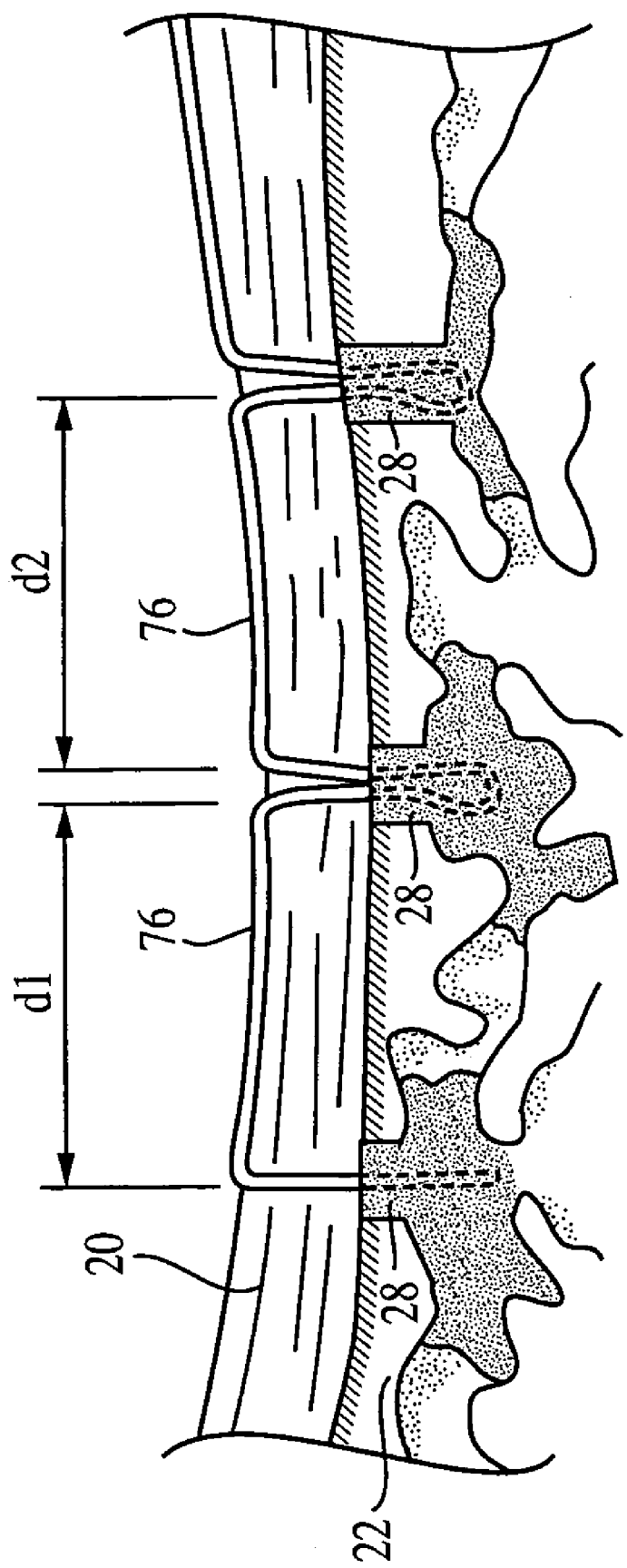

A procedure for fixing soft tissue to bone is shown in FIGS. 2–2K. In this procedure, one or more stitches are formed to fix the soft tissue to the bone over an area. The steps shown in FIGS. 2–2K are performed endoscopically, in the environment shown in FIG. 1. However, for the sake of clarity, only the surgical instrument 16, the bone and the soft tissue are shown in FIGS. 2–2K.

The steps shown in FIGS. 2–2K are performed using an endoscopic surgical instrument 16 that is constructed to perform a stitching operation. Generally, surgical instrument 16 includes a cannulated tube, a cutting tool within the cannulated tube, and a drive mechanism constructed to power the cutting tool to pierce soft tissue and form a cavity in the underlying bone. The drive mechanism is programmable, to allow the cutting tool to be either rotated or reciprocally oscillated (i.e., rotated back and forth through successive cycles, each rotation cycle being less than 360 degrees), as desired, for reasons that will be discussed below. The surgical instrument also includes a supply of suture material, e.g., on a spool, a mechanism for advancing the suture material through the cannulated tube, a chamber containing a supply of polymer in solid form (e.g., powder or pellets), and a heating element for melting the polymer for delivery in molten form. When the cutting tool is retracted, the suture and polymer are delivered through the cannulated tube, as will be described below, to anchor a portion of the suture in the cavity. Optionally, the surgical device may include a cannulated needle for positioning the suture in the cavity.

Using surgical instrument 16, a stitching procedure is performed as follows. First, the soft tissue 20 is held in place by the proximal end 19 of surgical instrument 16, and pierced by a cutting tool 26 (FIG. 2A). Cutting tool 26 also forms a cavity in bone 22 (FIG. 2A). Next, the cutting tool is retracted and a suture 70 is fed through the cannula 17 of the surgical instrument 16, e.g., from a reel of suture material (not shown) in the surgical instrument. The suture 70 may be positioned in the cavity by advancing a cannulated needle 72, through the cannula of which the suture is fed, into the cavity, as shown in FIG. 2B. Alternatively, the suture may be positioned by gravity or in any suitable manner.

After the suture is positioned, needle 72 is retracted and molten polymer 28 is injected into the cavity around suture 70 (FIG. 2C). The polymer 28 penetrates through the side walls and bottom of the cavity into the trabecular network (cancerous bone) in region 30.

Once polymer 28 has at least partially solidified, anchoring the suture in the cavity, the surgical instrument 16 is retracted (FIG. 2D), and suture 70 is fed from the surgical instrument as the surgical instrument is moved to a second location (FIG. 2E). As shown in FIG. 3A, and discussed in further detail below, as the suture 70 is fed from the instrument it exits the instrument through an inverted-L-shaped channel 69 extending up the side 74 of the surgical instrument, so that the suture is not cut during the piercing of the soft tissue.

When the surgical instrument is positioned at the second location, the surgical instrument again holds the soft tissue 20 in place, and cutting tool 26 again pierces the soft tissue 20 (FIG. 2E). The cutting tool 26 is then reciprocally oscillated to form a second cavity, as shown in FIG. 2F. (At this stage, the cutting tool cannot be rotated 360 degrees, as this would cut or break the suture, or cause the suture to wind around the cutting tool. Thus, the surgeon sets the programmable drive mechanism to an oscillating mode. The surgeon can use either a rotating or an oscillating motion to form the first cavity (FIG. 2A), depending on the surgeon's preference.) The suture 70 is fed from the supply reel into the new cavity, and positioned by advancing needle 72 into the cavity, as shown in FIG. 2G (as discussed above, the suture could instead be positioned by gravity).

A probe 71 is used to press the suture through the soft tissue, compressing the soft tissue against the surface of the bone in the vicinity of the second cavity and tensioning the suture material as it passes between the cavities, tightening the "stitch" that will be formed between the cavities. Needle 72 is retracted, leaving a loop of suture material (not shown) in the cavity, and molten polymer 28 is injected into the second cavity around the suture 70 (FIG. 2H).

Once the polymer in the second cavity has at least partially solidified, the surgical instrument 16 is again retracted (FIG. 2I). At this point, a "stitch" 76 of suture extends between the first and second cavities, holding region 20A of the soft tissue 20 securely against bone 22. The stitching procedure can then be terminated, as shown in FIG. 2J, by cutting the suture, or stitching can be continued, by repeating the above steps, to form a line of stitches as shown in FIG. 2K. The stitches can be of uniform lengths, or of different lengths (i.e., d1 may or may not be equal to d2). The suture can be cut, at the end of the procedure, using the surgical instrument 16 or a separate tool, e.g., a scalpel that is inserted through the cannula of an endoscope.

The polymer used in the procedure described above is preferably provided in the form of a plurality of pellets or a powder, and is preloaded into the surgical instrument prior to surgery, as will be described in further detail below. One pellet or shot of powder is used to fill each cavity. The pellets or powder are melted, to form the molten polymer, immediately prior to injection.

Many types of instruments may be suitable for use as surgical instrument 16 in the procedure described above with reference to FIGS. 2–2K. An example of a suitable surgical instrument, stitching instrument 50, is shown in FIGS. 3–3E.

Figure 7:
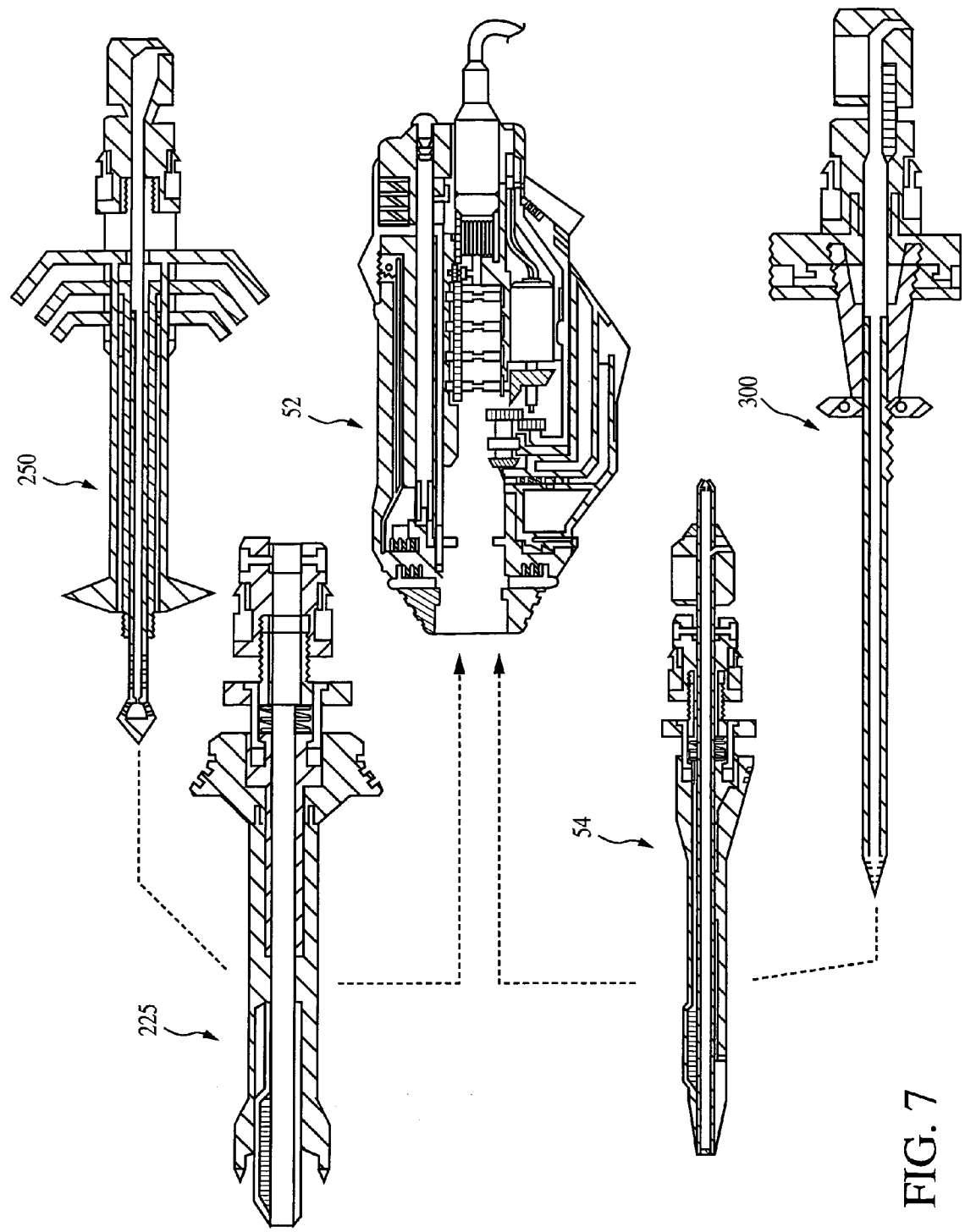
FIG. 7 is a diagrammatic cross-sectional view showing a handpiece and a number of interchangeable attachments that are mountable on the handpiece.

Instrument 50 includes a handpiece 52, and a removable attachment device 54. As indicated in FIG. 7, and discussed further below, attachment device 54 is one of many modular attachment devices that may be interchangeably mounted on handpiece 52. The attachment devices may be disposable. The handpiece 52 is sterilizable and is designed for repeated use, e.g., 100 uses or more. The attachment devices are clipped into the handpiece, on a bearing, as is well known for endoscopic surgical instruments with interchangeable attachments, such as those commercially available from Smith & Nephew, Andover, Mass., under the tradename DYONICS™.

Referring to FIG. 3, handpiece 52 is constructed to be held by a surgeon during a surgical procedure, and includes switches 56a, 56b and 56c that are positioned to be easily actuated by the surgeon to control the functions of the surgical instrument, as will be discussed below. Handpiece 52 is connected to a power supply by an adapter cord 39 (e.g., a Dyonics EP1 power supply cord, available from Smith & Nephew). The handpiece 52 may be fitted with interchangeable molded grips, e.g., two-piece housings that snap on over the handpiece 52 and include recesses through which switches 56 extend, thus providing the surgeon with a more customized grip.

Figure 3B:
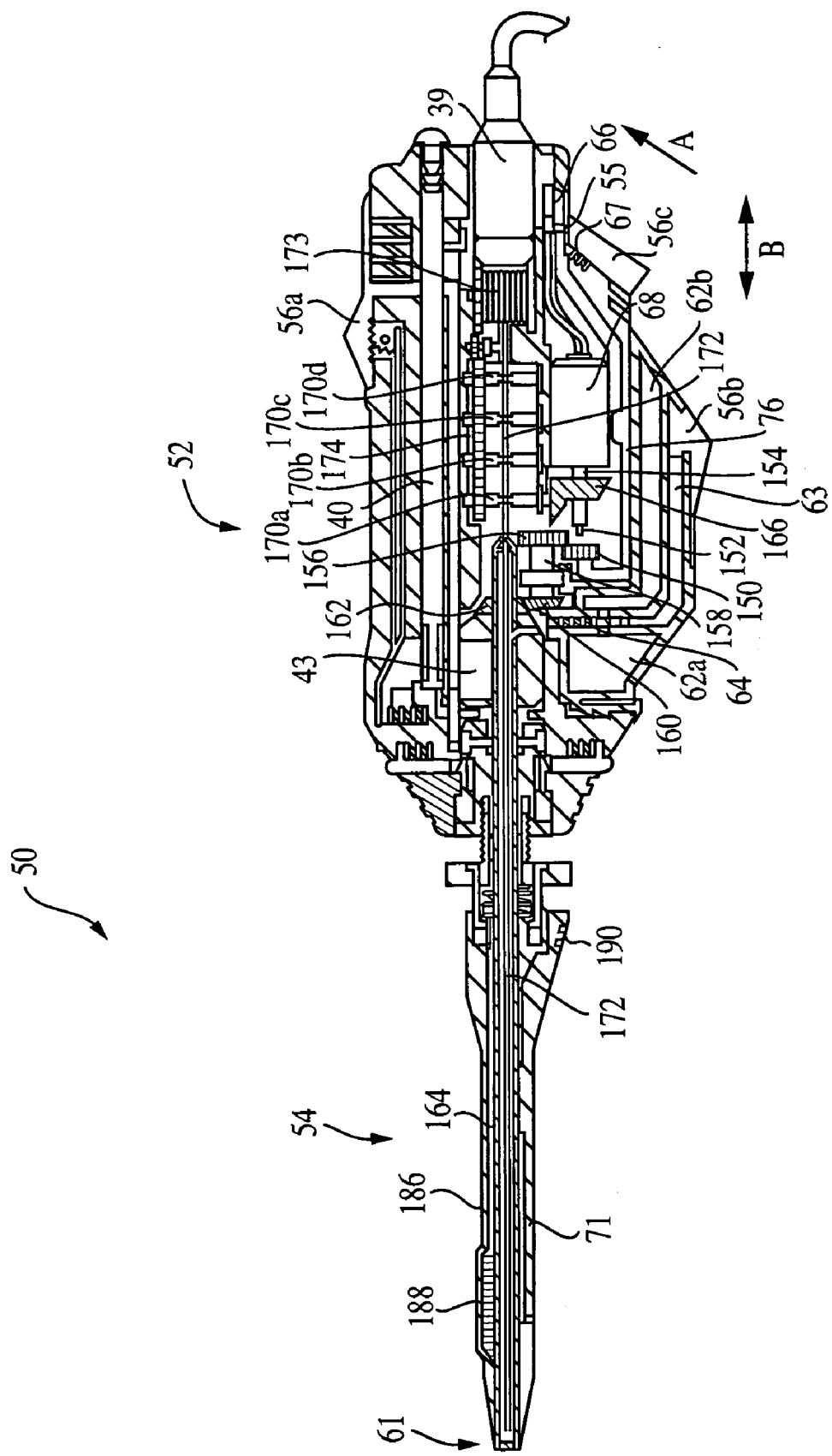
FIG. 3B is a cross-sectional view of the surgical instrument of FIG. 3.
Figure 3E:
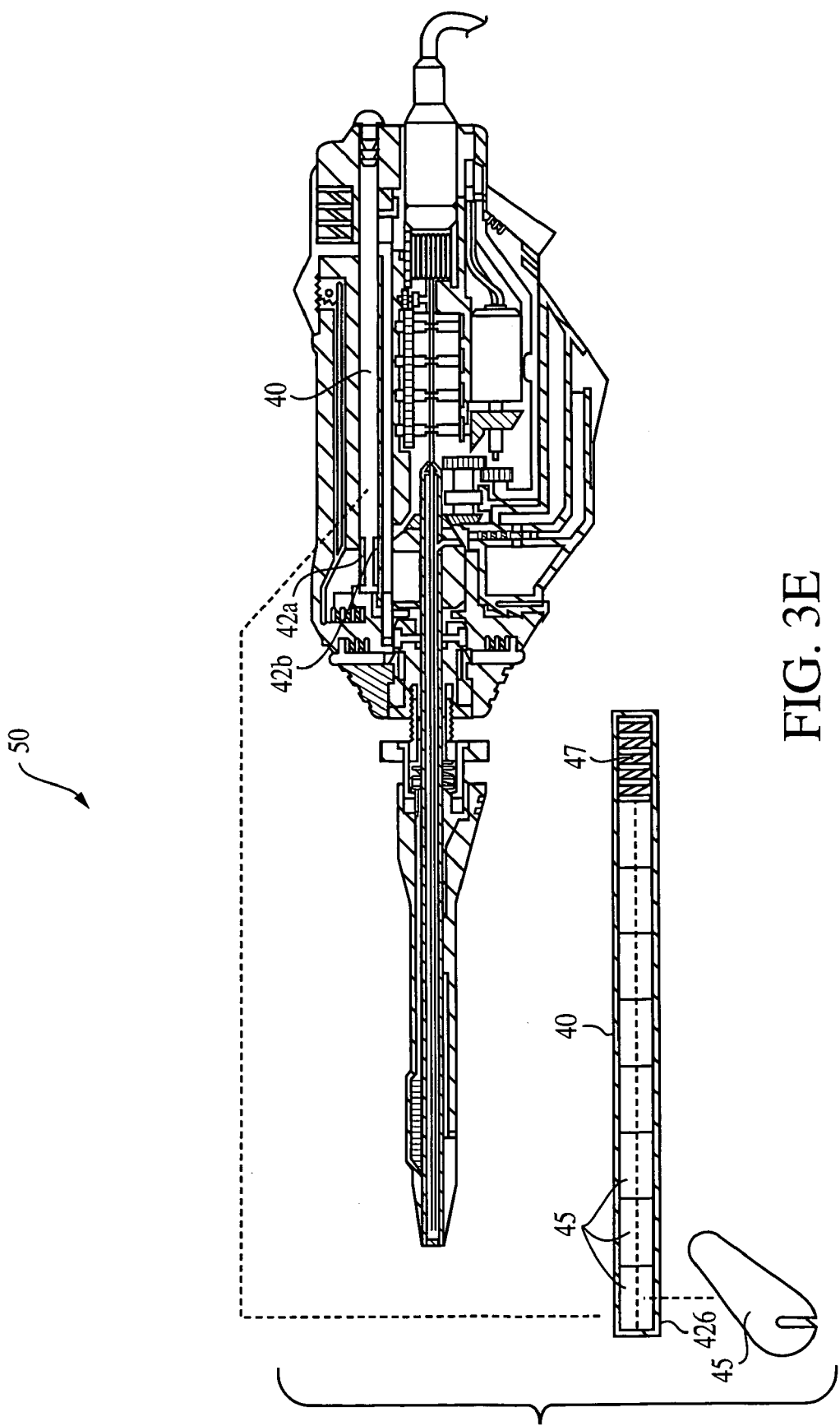

Referring now to FIGS. 3B and 3C, the handpiece 52 includes a removable polymer cartridge 40 that is preloaded with a supply of polymer pellets 45 (FIG. 3E) prior to surgery, and a chamber 41 (FIG. 3C) for receiving the polymer cartridge. The polymer cartridge 40 includes aligned slots 42a, 42b, through which a pellet can be pushed out for delivery to a cavity.

To push a pellet out of the cartridge for delivery, the surgeon pulls back on switch 56a. This causes toothed cam 57 to push rod 58 against inclined surface 59 of block 60, causing block 60 to move downward through slot 42a, thereby displacing the pellet through slot 42b into chamber 43 through an cavity that is not shown in the cross-section of FIG. 3B. The pellet then passes into the lumen of the attachment 54 through an cavity 44 (FIG. 3D). After the pellet has been dispensed, block 60 is returned to, and biased in, its previous position by spring 61. This reverses the movement of the rod 58 and toothed cam 57, returning the switch 56a to its normal position. The pellets are advanced toward the proximal end of the cartridge, to move a new pellet into place for delivery through slot 42b, by spring 47 (FIG. 3E).

The polymer pellet is moved to the delivery end 61 (FIG. 3B) of the instrument 50 by compressed gas delivered from pre-filled reservoirs 62a and 62b. To deliver air to move the pellet, the surgeon pushes switch 56b forward, which moves a hydraulic fluid in chamber 63 against spring 64, cavity a valve (not shown) to release the compressed gas from the reservoirs into the lumen of the attachment 54.

The cutting tool (cutting device 176, discussed below) and the suture delivery mechanism are both driven by a single motor, and a clutch mechanism and switch are provided to allow the surgeon to selectively activate the piercing/cavity forming function of the cutting device and the suture delivery function (performed by the suture delivery mechanism), as will be discussed below. The motor is normally off, and is activated by the surgeon pressing switch 56c upward (arrow A, FIG. 3B), moving contact 65 into engagement with contact 66 of motor 68. The switch is held in the engaged position by a catch (not shown), so that to deactivate the motor the surgeon needs to press the switch upward again, as which point spring 67 will return the switch to its normal position.

The surgeon can select between the piercing/cavity forming function and the suture delivery function by moving switch 56c back and forth axially (arrow B, FIG. 3B). This causes member 76 to move axially, engaging a set of gears that drives one of these functions and disengaging a set of gears that drives the other function, as will be discussed further below.

When the suture delivery function is selected, i.e., when switch 56c is in the position shown in FIG. 3B (its left-hand position), bevel gear 166, mounted on drive shaft 154 of the motor, is engaged with bevel gear 168, which drives a suture feed cog 170a, through which a suture 172 (FIG. 3B) is fed from a reel 173. A series of bearings 174 drive suture feed cogs 170b–170d, which advance the suture towards the delivery end 61 of the surgical instrument.

When the piercing/cavity forming function is selected, i.e., when switch 56c is moved to the right in FIG. 3B, a spline (not shown) in the center of cog 150 engages end 152 of drive shaft 154 of the motor. Simultaneously, the teeth of cog 150 engage the teeth of cog 156, causing shaft 158 to rotate, driving bevel gear 160 which engages bevel gear 162 on the cutting tube 164 of attachment 54. Engagement of bevel gears 160 and 162 rotates the cutting device 176 (or oscillates the cutting device, depending on the setting of the programmable drive). The motor is programmed to stop rotation, when the piercing/cavity forming function is deselected, in a position in which cavity 44 is aligned with the polymer-delivery cavity in the handpiece that is in turn aligned with cavity 42b of the polymer cartridge.

Referring to FIG. 3D, the attachment 54 includes an inner cutting device 176 that slides into an outer guide/heating device 178 when the surgical instrument is assembled for use. When the instrument is assembled, as shown in FIG. 3C, the guide/heating device 178 snaps into the handpiece 52, and the cutting device 176 is trapped between the handpiece 52 and the guide/heating device 174.

Cutting device 176 includes a cannulated cutting tube 164 having a cutting tip 180, a member 182 that defines chamber 43 and a gas inlet 184, and bevel gear 162. End 181 of the cutting tube includes a flap valve 183 to prevent the compressed gas from escaping through end 181. When the suture delivery function is selected, the pressure of the end of the advancing suture opens valve 183, and the suture is guided through the cavity at end 181 by a conical portion 185.

Guide/heating device 174 includes a cannulated guide tube 186 and, within the guide tube, a heating element 188 for melting the polymer pellets. The guide tube 186 includes a movable probe portion 71, which can be moved axially (arrows C, FIGS. 3 and 3A) by the surgeon, using grip 190, to push the suture 172 against the soft tissue as discussed above. The probe portion is in its upper position in FIG. 3A, allowing clearance for the suture as it feeds from the tip. It is lowered prior to dispensing the polymer (to keep the polymer from escaping through channel 69), and to tighten the suture when a stitch is formed. The guide tube 186 is spring loaded so that it will retract under pressure when pressed against the soft tissue, allowing the cutting tip to penetrate the bone to a desired depth which is determined by the degree of spring loading. When pressure is released, the guide tube is biased by the spring load back to its normal, extended position. The guide/heating device also includes an attachment portion 200 that releasably snap fits into the handpiece.

Thus, to use the stitching instrument 50 in the procedure shown in FIGS. 2–2K and described above, a surgeon would first preload a supply of polymer into the instrument 50, by installing polymer cartridge 40, preprogram the programmable drive mechanism as desired, and move probe portion 71 to its lowered position. The surgeon would then press the delivery end 61 of the device against the soft tissue, and select the piercing/cavity forming function by moving switch 56*c* to the appropriate position, to pierce the soft tissue and form a cavity. Next, the surgeon would move switch 56*c* to select the suture delivery function, and deliver a desired amount of suture material to the cavity. After delivery of the suture, the surgeon would move switch 56*c* to deactivate the drive motor (turning off both the piercing/cavity forming and suture delivery functions), and pull back on switch 56*a* and push forward on switch 56*b* to deliver polymer to the cavity. Once the polymer had at least partially solidified, the surgeon would raise probe portion 71, move switch 56*c* to select the suture delivery function, and feed out suture while moving the instrument 50 to a second location. At the second location, the surgeon would move switch 56*c* to select the piercing/cavity forming function, and form a second cavity. The surgeon would then move switch 56*c* to select the suture delivery function, deliver a desired amount of suture to the cavity, move switch 56*c* to deactivate the drive motor, lower probe portion 71 to tighten the "stitch" between the cavities, and move switches 56*a* and 56*b* to deliver polymer to the cavity. These steps would be repeated to form as many stitches as desired.

If desired, the surgical instrument may be used to deliver polymer without performing any cutting procedure.

Figure 4A:
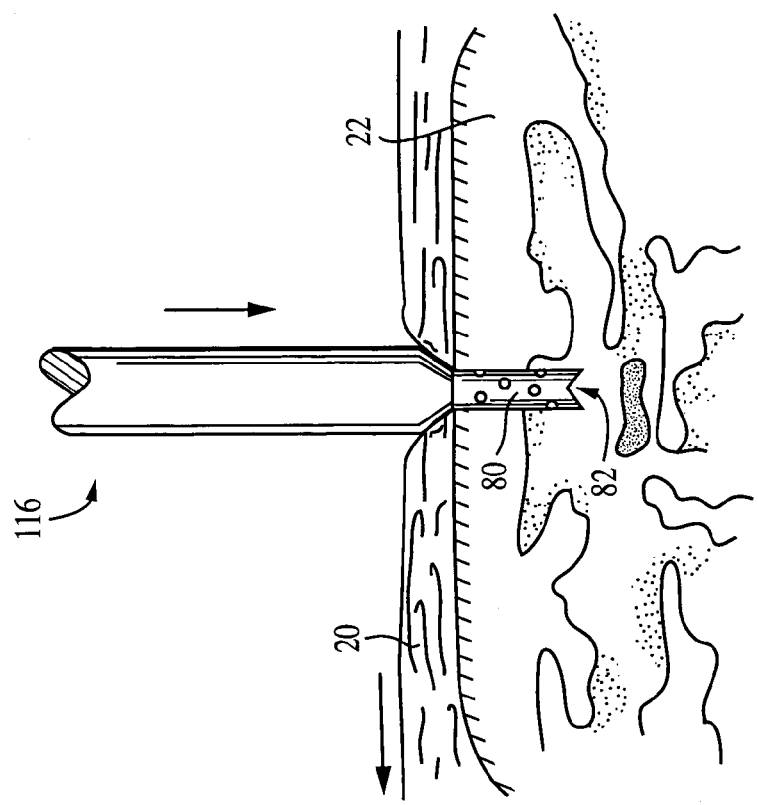
FIGS. 4–4J are diagrammatic views of an alternative procedure for forming a series of polymeric anchors connected by stitching.
Figure 4:
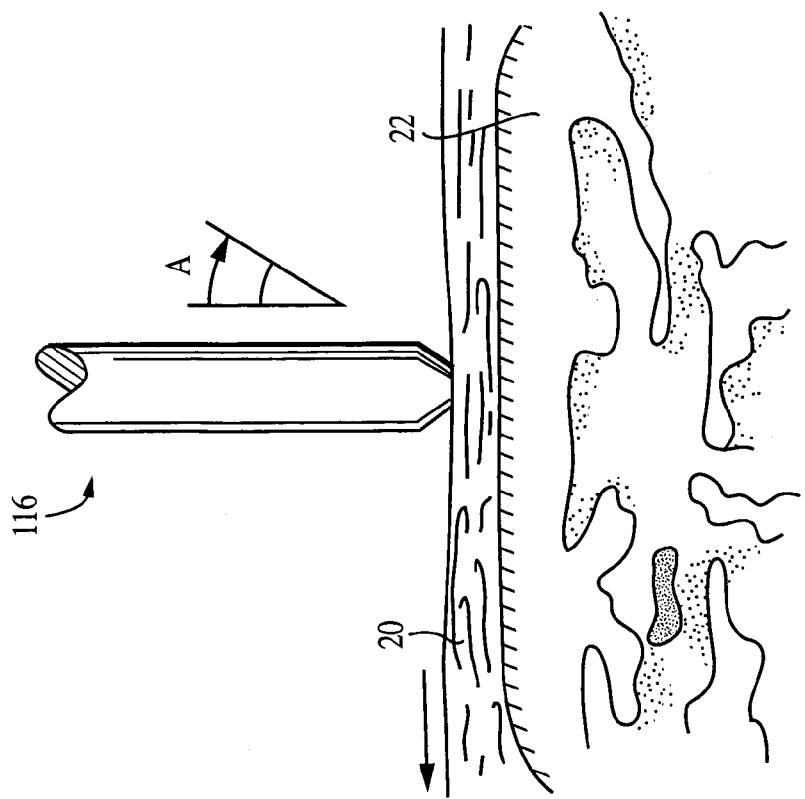
Figure 4C:
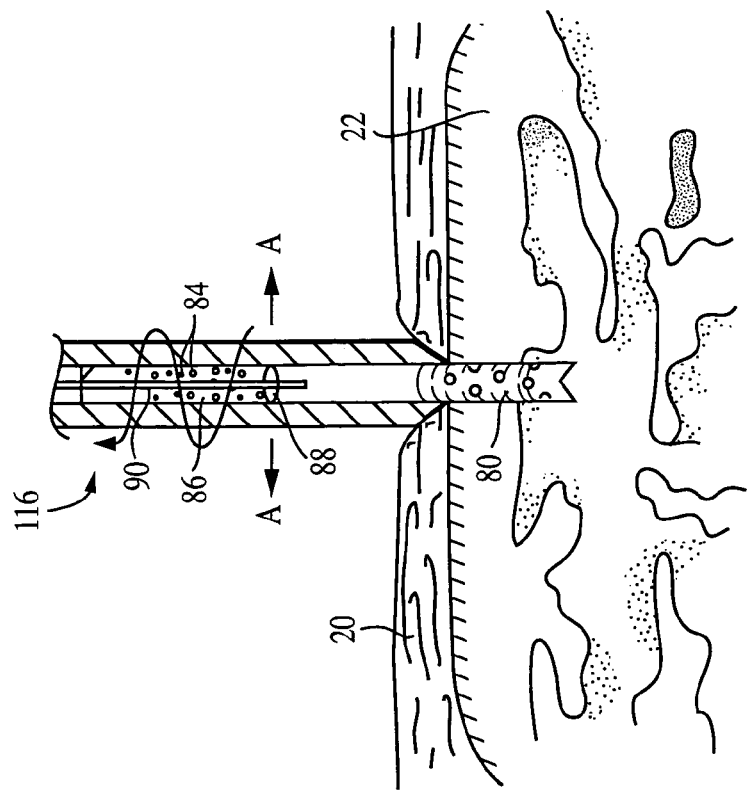
Figure 4B:
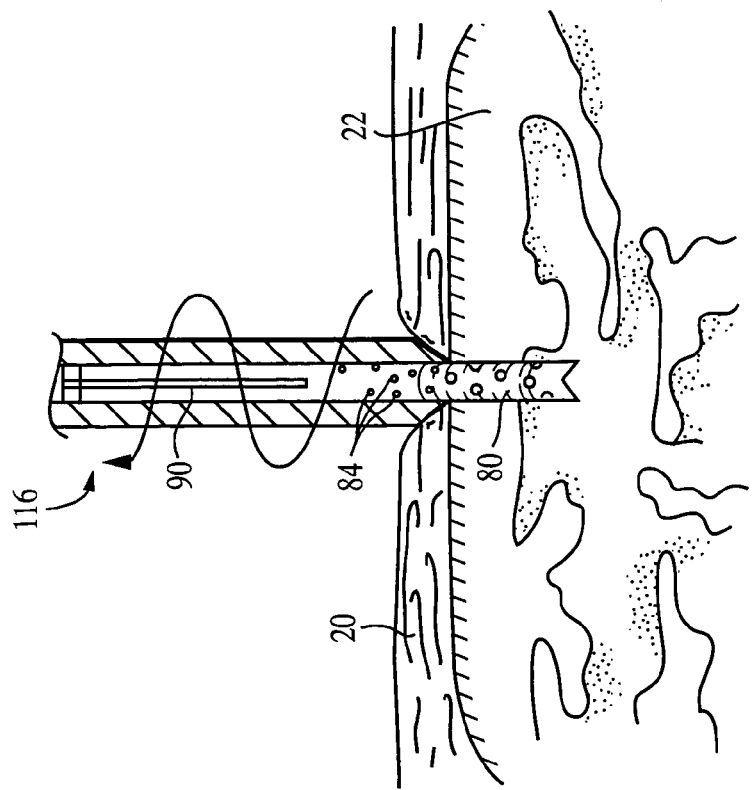
Figure 4E:
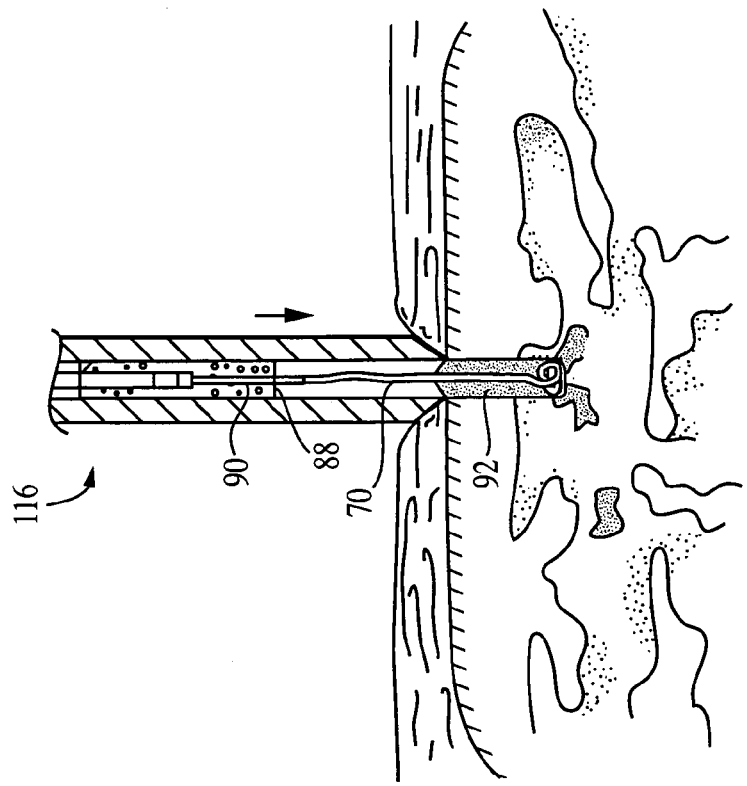
Figure 4D:
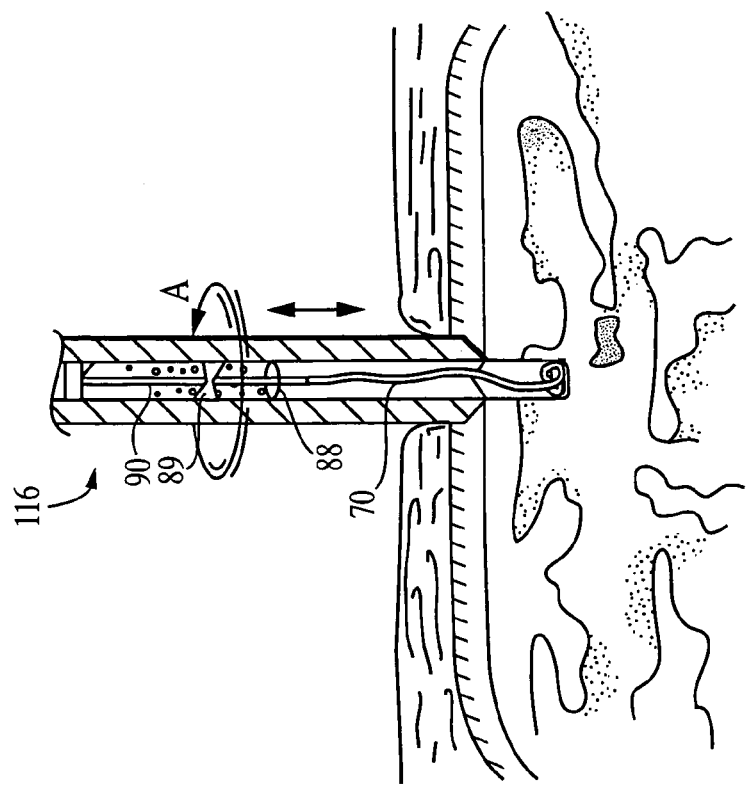
Figure 4G:
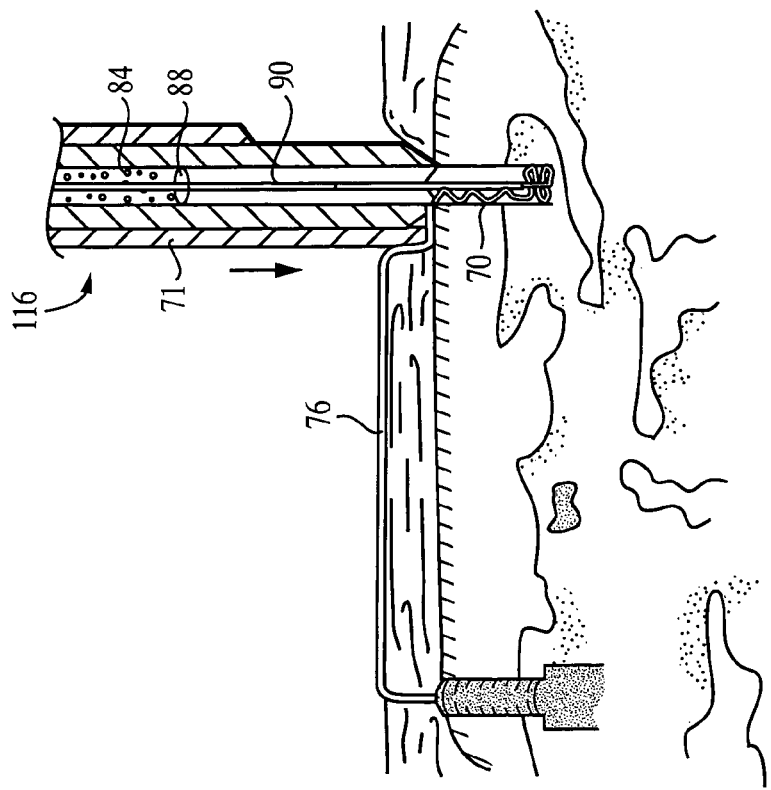
Figure 4F:
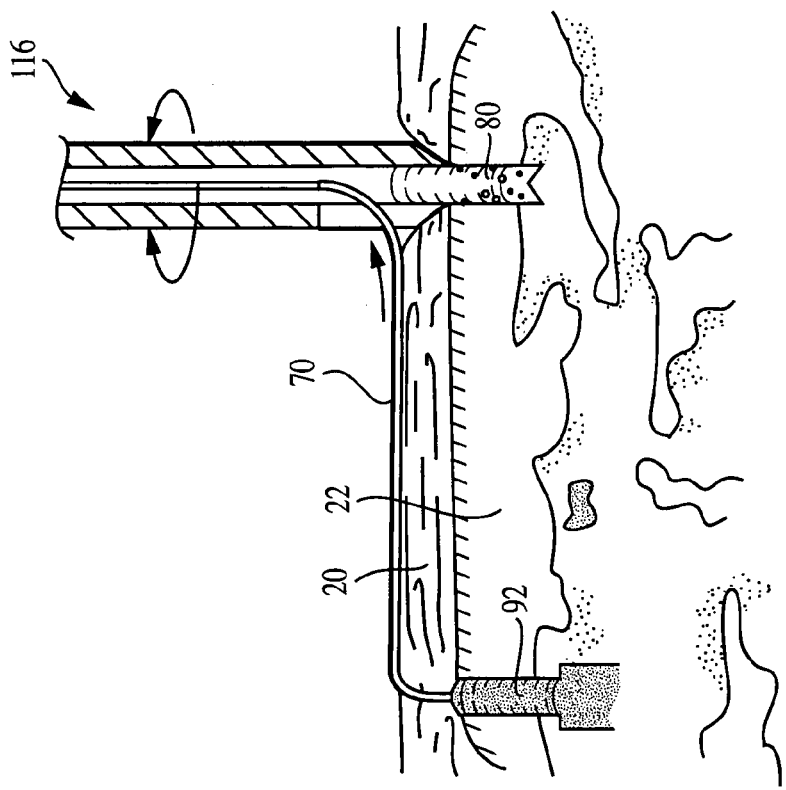
Figure 4I:
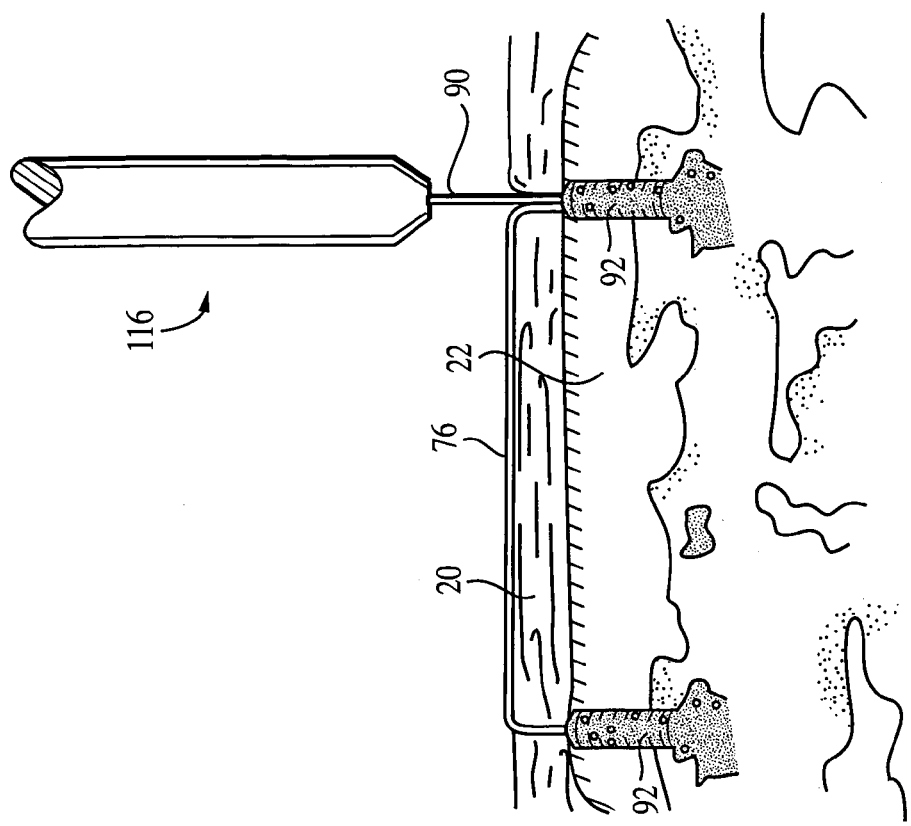
Figure 4H:
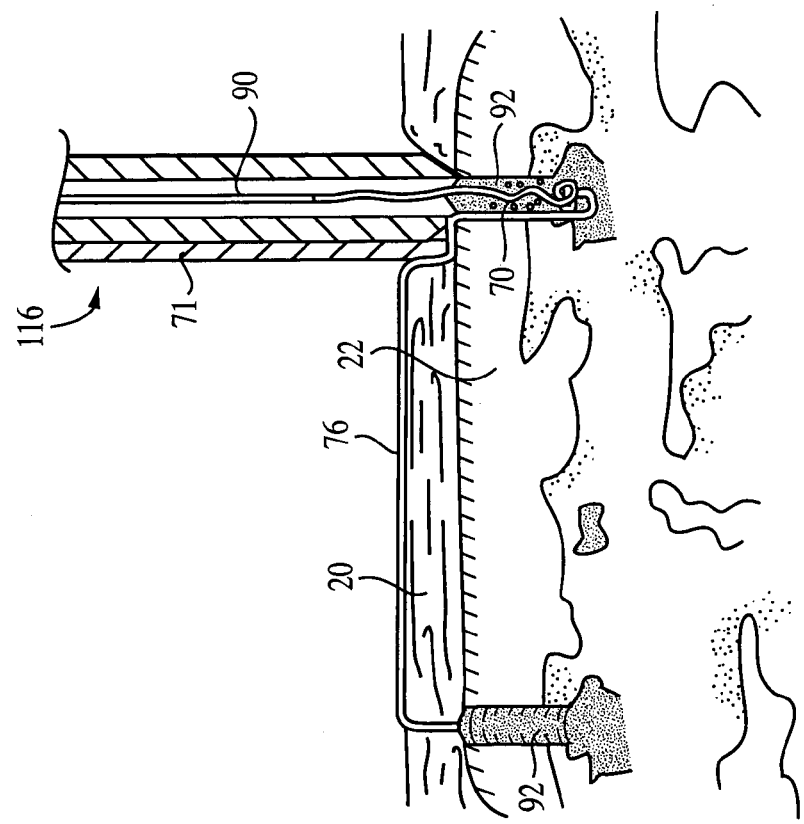
Figure 4J:
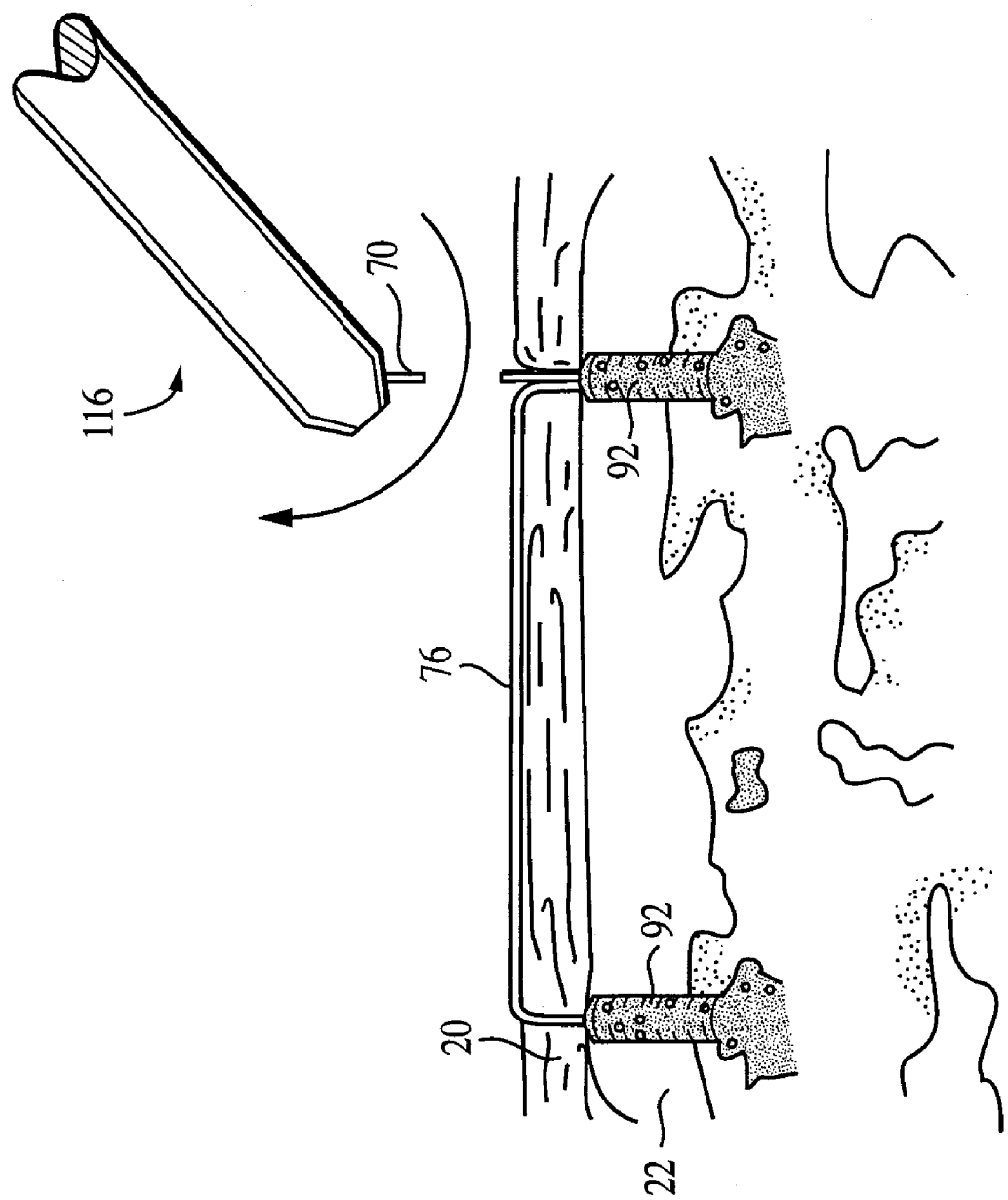

An alternative procedure for forming a row of stitches is shown in FIGS. 4–4G. In this procedure, the bone fragments and debris generated during cavity forming are incorporated into the polymer as a filler. It is noted that bone fragments and debris can be incorporated into the polymer in a similar manner in any of the procedures described herein. The procedure shown in FIGS. 4–4G is performed using a surgical device 116 that is similar to surgical device 16, except that it also includes a suction device for extracting bone fragments and debris from the cavity, and a mixing chamber and a mixing device, for incorporating the bone fragments and debris into the polymer.

Referring to FIGS. 4 and 4A, using surgical instrument 116 the soft tissue 20 is pierced and a cavity is drilled in the bone 22, as discussed above. In this embodiment, the cutting tool is a perforated drill 80 (similar to a grater), having a serrated tip 82. Because the drill tip is serrated, it is preferred that the surgical instrument 116 be held at an angle, rather than perpendicular to the surface of the soft tissue 20, as indicated by angle A in FIG. 4, until the soft tissue 20 has been pierced. During drilling, the resulting bone fragments and debris 84 are suctioned out of the cavity and up through the cannula of the drill, as indicated schematically in FIG. 4B. The bone fragments/debris are then retained in a temporary chamber 86, defined by the cylindrical cutting tool barrel and a balloon diaphragm 88, suspended on a needle 90, that is inflated at this point in the procedure (arrows A, FIG. 4C). As shown in FIG. 4D, the surgeon then delivers suture 70 through needle 90, while simultaneously adding polymer to chamber 86 and mixing the polymer with the bone fragments/debris 84 (arrow A). Using the air supply, the polymer is fed to chamber 86, in powder form, from a reservoir that is preloaded prior to surgery. Mixing can be performed using any desired mixing device, e.g., a mobius band 89 mounted on needle 90. The polymer is heated during or after mixing. Once the polymer has melted, the polymer/bone fragment mixture 92 is delivered from the temporary chamber 86 to the cavity by collapsing the diaphragm 88 so that the polymer mixture will flow into the cavity due to the force of gravity (FIG. 4E). The surgeon collapses the diaphragm by operating a switch on the surgical device which inflates and deflates the diaphragm, in the same manner that balloon catheters are conventionally actuated. The remaining steps of the procedure, shown in FIGS. 4F–4J, are conducted in the same manner as the steps shown in FIGS. 2E–2J and discussed above, except that bone fragments and debris are collected and mixed into the polymer each time a cavity is drilled.

Figure 5B:
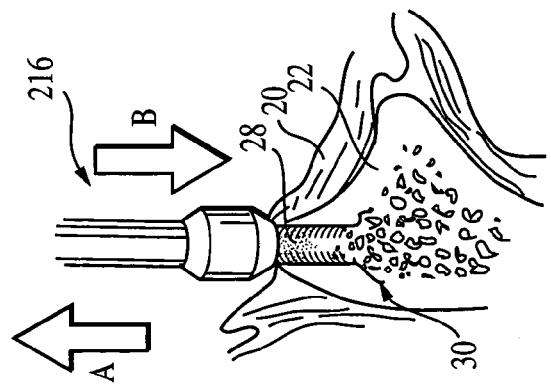
FIGS. 5–5F are diagrammatic views of a procedure for forming a sutureless polymeric anchor to fix soft tissue to bone.
Figure 5A:
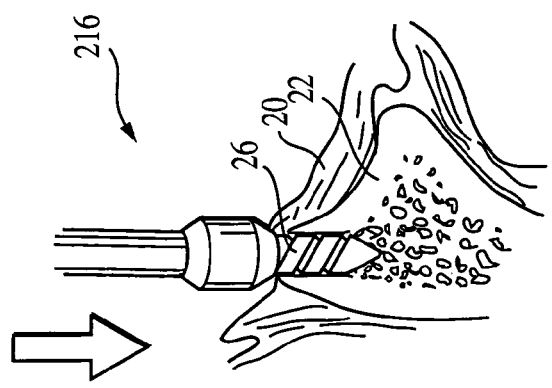
Figure 5:
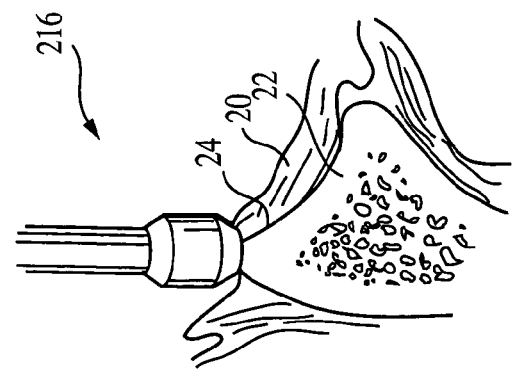
Figure 5C:
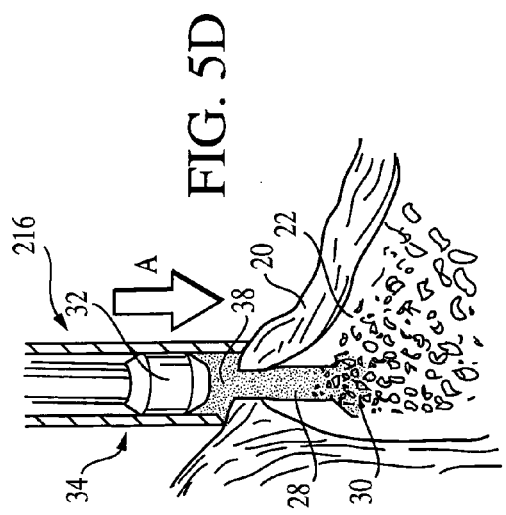
Figure 5D:
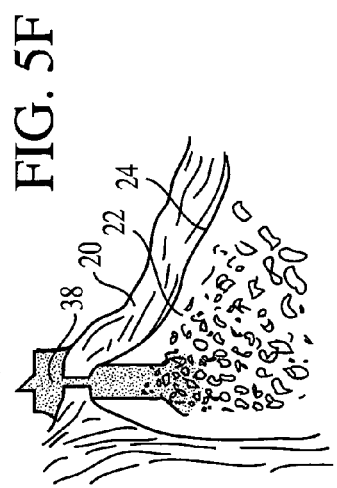
Figure 5E:
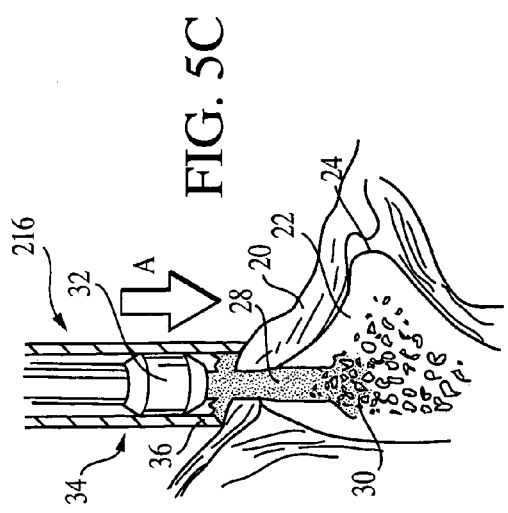
Figure 5F:
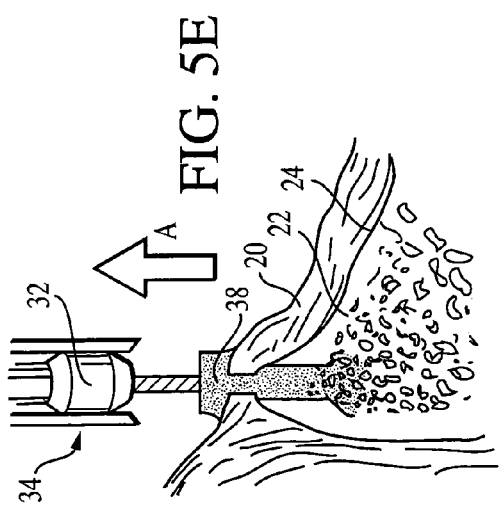

An alternate surgical procedure, used to form a single, bolt-like polymeric anchor, is shown in FIGS. 5–5F. This procedure utilizes a surgical instrument 216, which includes a cutting tool to pierce soft tissue and form a cavity in bone, a supply of polymer and a heating element to melt the polymer, a cannulated tube to guide the cutting tool and deliver the polymer to the cavity, and a compounder that is constructed to form a molding cavity for shaping the "head" of the bolt-like anchor.

Referring to FIGS. 5–5F, a surgical instrument 216 is pressed against the soft tissue 20, which is in turn pressed against the bone surface 24 (FIG. 5), and a cutting tool, e.g., a drill bit 26, is used to pierce soft tissue 20 and form a cavity in bone 22 (FIG. 5A). The cutting tool is then retracted (arrow A, FIG. 5B), and a molten polymer 28 (e.g., melted as described above) is injected into the cavity (arrow B, FIG. 5B) through a cannula of the surgical instrument 216.

Next, a compounder 34 (a part of surgical instrument 16 that has been retracted in previous steps) is extended (arrow A, FIG. 5C) so that the tip 36 of the compounder presses against soft tissue 20 to hold it against bone surface 24. Meanwhile, the cannulated head 32 of the surgical instrument 16, through which the polymer is delivered, is retracted a short distance so that, with the cylindrical wall of the compounder, it defines a small molding chamber. Polymer continues to be delivered through the cannula of the surgical instrument and this polymer fills the molding chamber to form a polymeric "bolt head" 38 (FIG. 5D). The bolt head 38 is integral with the polymer in the cavity, which extends through the soft tissue 20. Thus, the polymer forms a bolt-like anchor that secures the soft tissue to the bone (FIGS. 5E and 5F).

As shown in FIGS. 5E and 5F, the procedure is completed by removing the surgical instrument 16 (arrow A, FIG. 5E) and snipping any excess polymer off at the top of the bolt head. The manner in which the polymer is snipped off is not shown; if this step is necessary, it can be performed using a clipper attachment to the surgical instrument 16, or using a separate device such as a scalpel.

Figure 6:
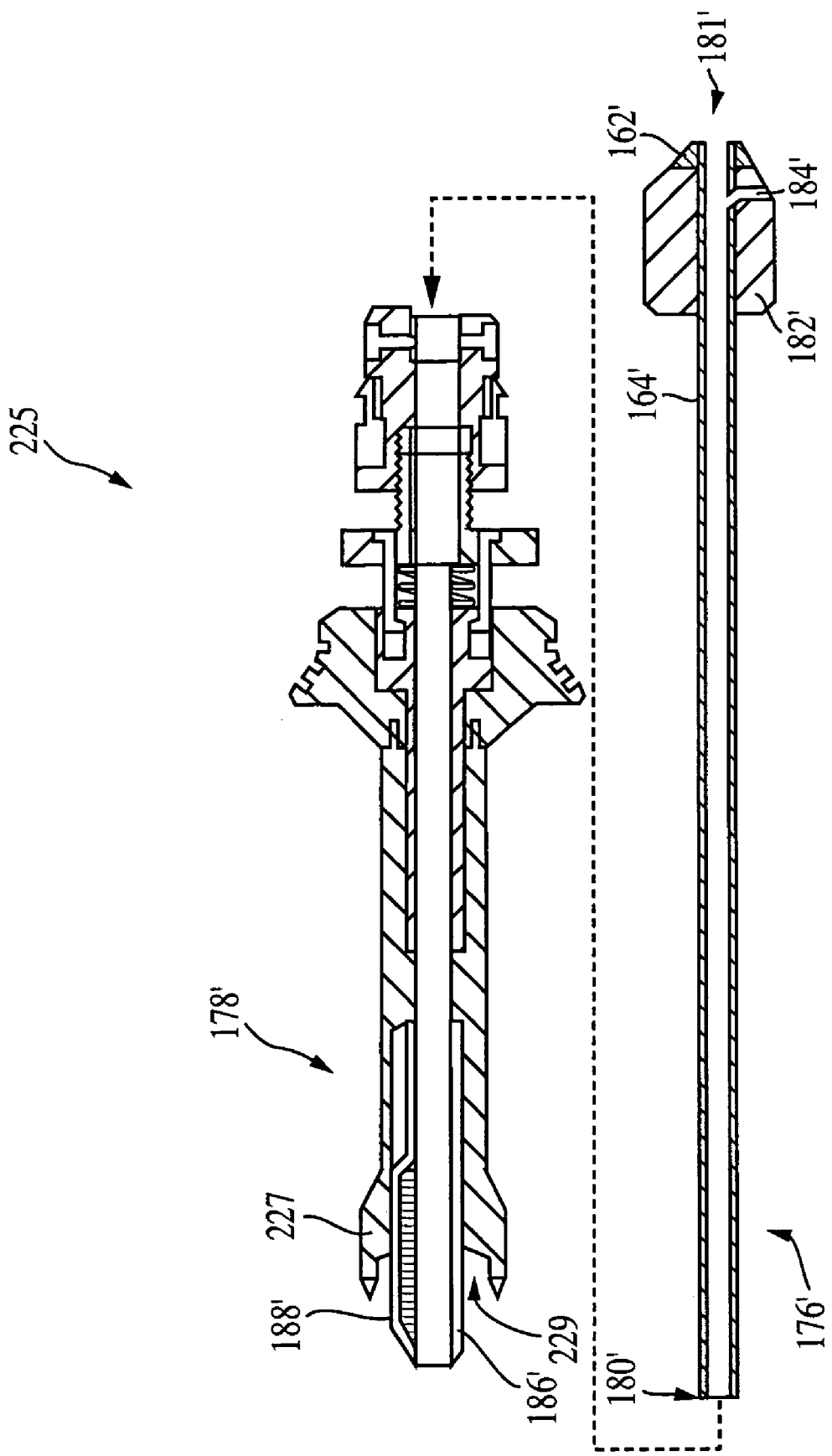
FIG. 6 is an exploded cross-sectional view of a surgical instrument attachment suitable for use in the procedure of FIGS. 5–5F.

The procedure shown in FIGS. 5–5F can be performed using an attachment 225, shown in FIG. 6, mounted on the handpiece 52 that is shown in FIGS. 3–3D and discussed above. The handpiece 52 can be used with a wide variety of interchangeable attachments, suitable for use in various procedures of the invention. For example, as shown in FIG. 7, the handpiece can be used with attachment 54 to perform a stitching procedure, with attachment 225 to form a bolt-like polymeric anchor using the procedure shown in FIGS. 5–5F, and with attachments 250 and 300 to perform soft tissue to soft tissue fixation procedures that will be described below.

Figure 6A:
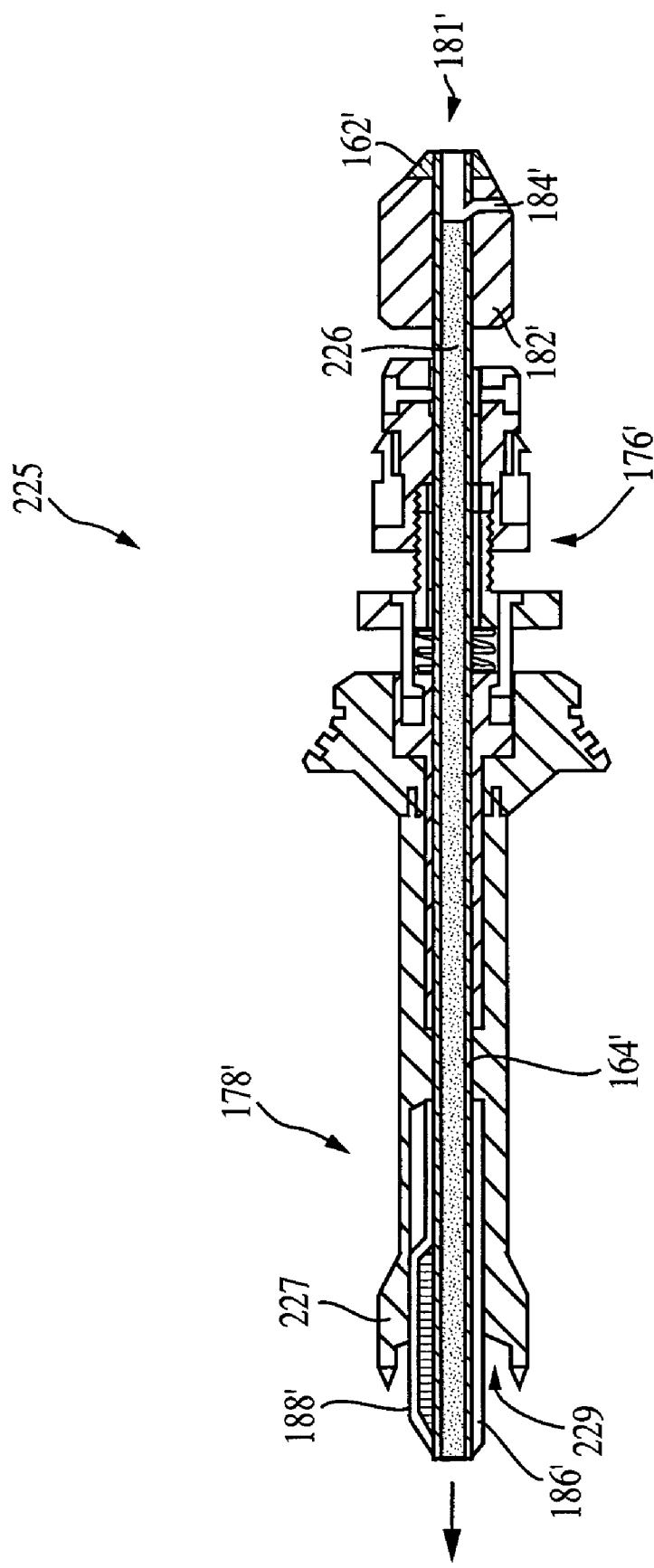
FIG. 6A is a cross-sectional view of the surgical instrument attachment of FIG. 6 assembled.

Attachment 225 is similar to attachment 54, discussed above, except that it does not include a chamber or cavity for receiving a polymer pellet. Instead, a polymer rod 226 (FIG. 6A) is advanced through the handpiece using the suture delivery function. The polymer rod 226 includes a grommet (not shown) at its distal end 228, to prevent gas from escaping through end 181'. Also, the guide/heating device 178' includes a compounder 227 which defines a molding chamber 229, as discussed above. The compounder 227 is moved axially by the surgeon as discussed above with reference to FIGS. 5C–5E.

In another embodiment, fixation methods are provided for attaching soft tissue to soft tissue. These fixation methods are suitable for use, for example, in laparoscopic surgery. Procedures and devices for soft tissue to soft tissue fixation are shown in FIGS. 8–11 and described below.

Figure 8E:
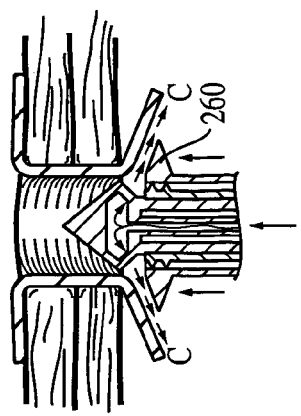
FIGS. 8–8F are diagrammatic views of a procedure for fixing soft tissue to soft tissue with a polymeric anchor.
FIG. 8G is a partial perspective view of the finished anchor.
Figure 8D:
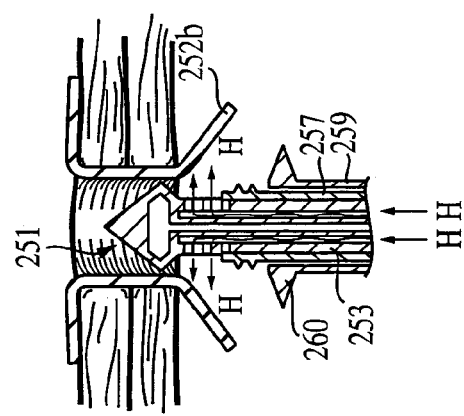
Figure 8C:
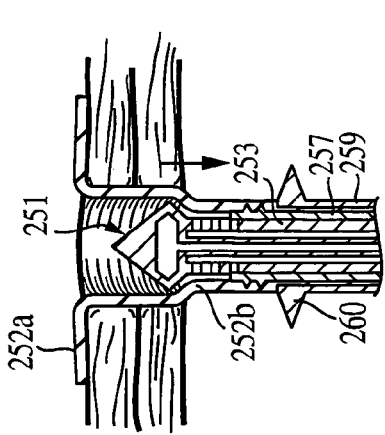
Figure 8G:
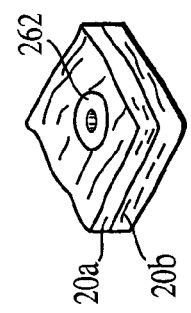
Figure 8F:
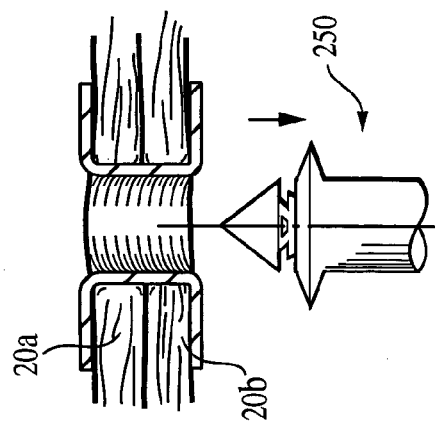
Figure 9:
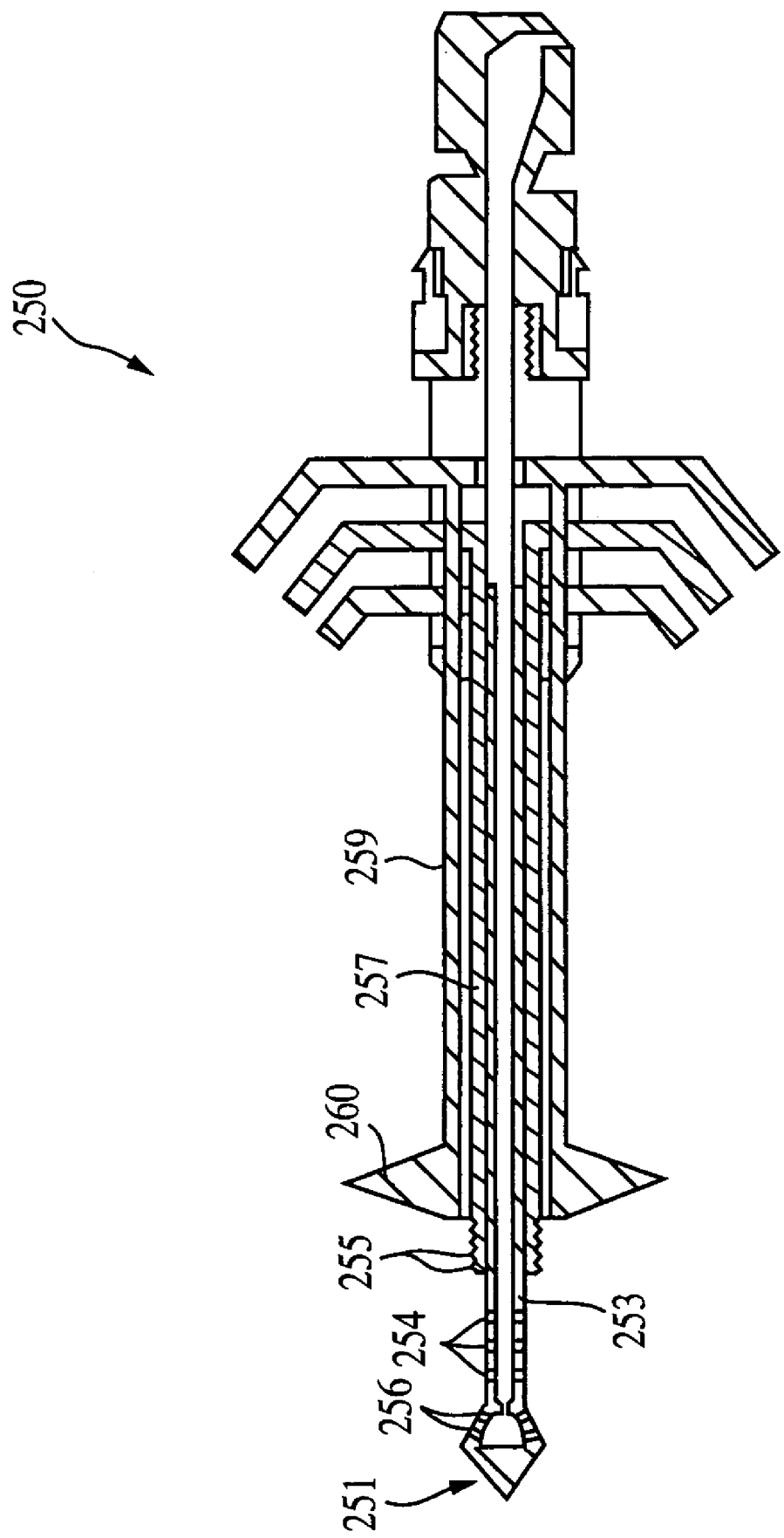
FIG. 9 is a cross-sectional view of a surgical instrument attachment suitable for use in the procedure of FIGS. 8–8F.

A first procedure, which forms a polymeric "rivet", is shown in FIGS. 8–8F. This procedure uses a surgical instrument 316, which generally includes an inner, axially movable tube having a sharp tip for piercing through soft tissue, and a cannulation in communication with a number of openings for delivery of hot and cold air from the inner tube. The surgical device also includes an outer tube, on which is mounted a polymeric sheath that will be softened and shaped by the delivered air to form the rivet, and a compounder, surrounding the outer tube, that includes a flange for directing the air and shaping the polymeric sheath into a rivet shape.

Referring to FIG. 8, two portions of soft tissue 20a, 20b, are compressed together (arrows A, FIG. 8), using known surgical techniques. Next, the tip 251 of an inner, axially movable tube 253 (FIG. 9) of surgical device 316 is punched through the soft tissue (FIG. 8A). A polymeric sheath 252 is mounted on outer tube 257, and a portion 252a of the polymeric sheath is carried through the soft tissue and out the other side. The polymeric sheath is held in place by ridges 255 on outer tube 257. Outer tube 257 is surrounded by compounder 259, the function of which will be described below.

Hot air (arrows H, FIG. 8B) is then directed out of side openings 254 of tip 251, and cold air (arrows C, FIG. 8B) is directed out of tip openings 256. The hot air melts the polymeric sheath, and the cold air forces it downward (arrows D, FIG. 8B) against the soft tissue (FIG. 8D). The hot air is generated at the tip due to the relationship between the air pressure being forced out of the tip and the size of side openings 254.

The inner tube 253 of instrument 250 is then withdrawn through the polymeric sheath until the side openings 254 are aligned with portion 252b of the polymeric sheath (FIG. 8C). Hot air is directed out through the side openings 254 (arrows H, FIG. 8D) to melt portion 252b. Flange 260 of compounder 259 is then pressed against portion 252b, while cold air is directed out through tip openings 256 (FIG. 8E), solidifying portion 252b in place against the soft tissue (FIG. 8F). The air is directed by flange 260, which also serves to press portion 252B against the soft tissue. The surgical instrument 316 is then withdrawn (FIG. 8F), leaving a rivet-like anchor 262 (FIG. 8G) to hold the soft tissue firmly together.

A surgical instrument attachment 250, for use with handpiece 52 to form a surgical instrument 316 suitable for performing the procedure shown in FIGS. 8–8F and described above, is shown in FIG. 9. Attachment 250 includes the components described above with reference to FIGS. 8–8F, and can be mounted on bandpiece 52 in the same manner as attachment 54, discussed above.

Figure 10B:
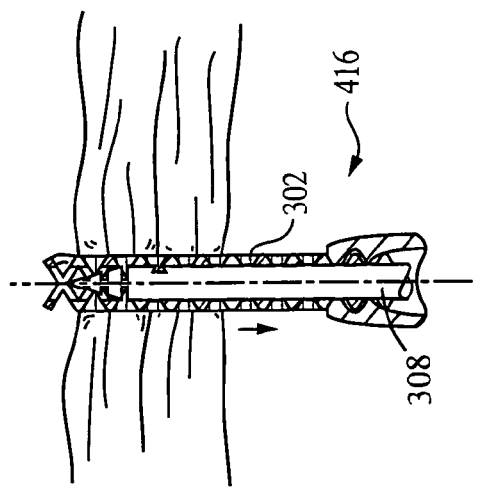
FIGS. 10–10H are diagrammatic views of an alternative procedure for fixing soft tissue to soft tissue with a polymeric anchor.
Figure 10A:
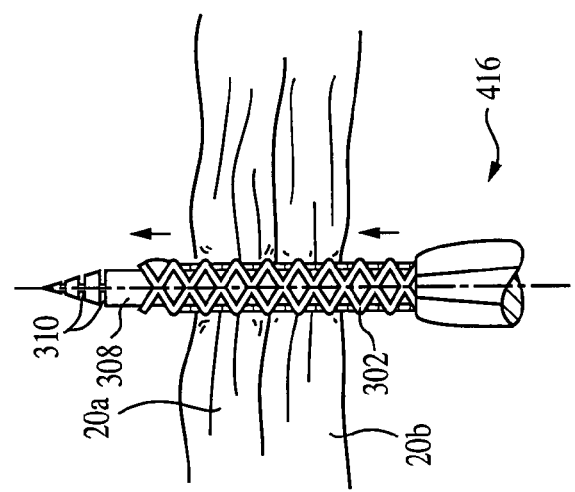
Figure 10:
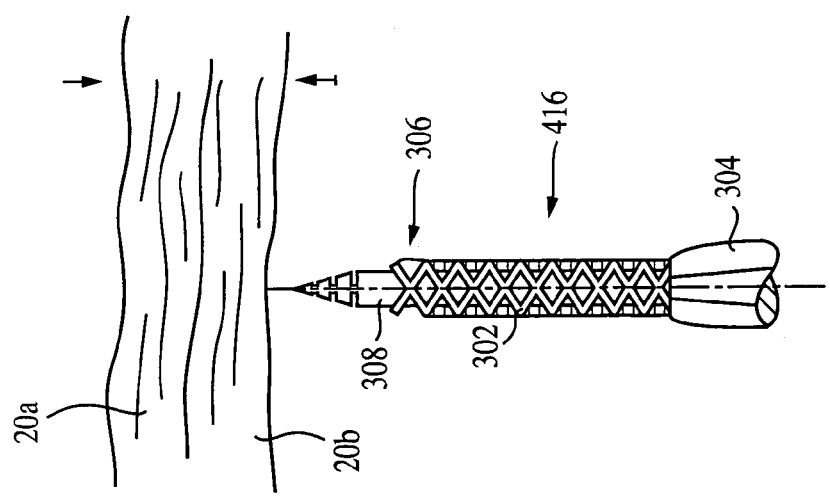
Figure 10C:
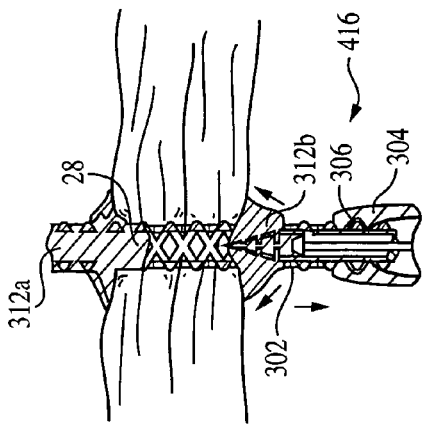
Figure 10D:
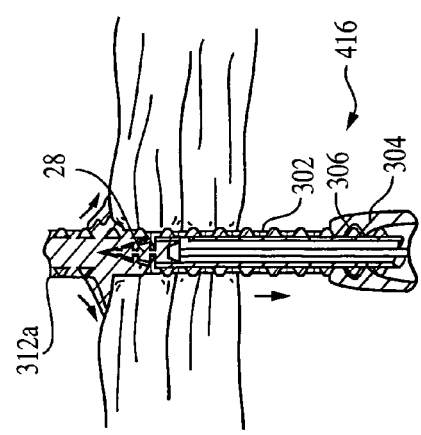
Figure 10F:
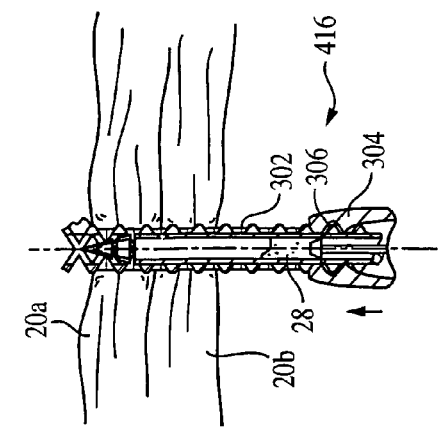
Figure 10E:
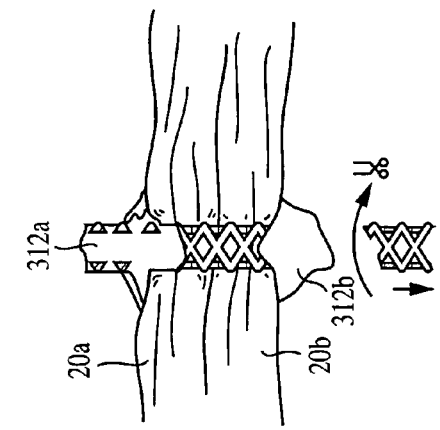
Figure 10G:
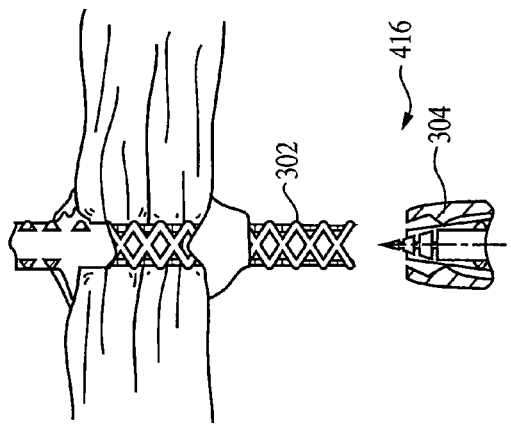
Figure 10H:
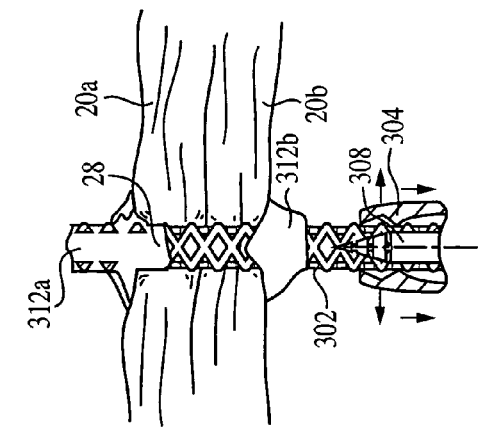

An alternative procedure for fixing soft tissue to soft tissue is shown in FIGS. 10–10H. This procedure is performed using a surgical instrument 416, which generally includes an inner tube having a sharp tip for piercing soft tissue and a cannulation for delivery of polymer. The surgical instrument 416 also includes a device for releasably mounting a porous sheath over the inner tube.

First, the soft tissue is compressed and is pierced by the sharp tip of surgical device 416 (FIGS. 10, 10A), as described above with reference to FIGS. 8 and 8A. The distal end 306 of a porous sheath 302, e.g., a braid or mesh, is gripped by a releasable chuck 304. A small polymer weld (not shown) near distal end 306 of the sheath keeps the sheath from being forced backwards during the piercing step.

The inner tube 308 is then withdrawn slightly (FIG. 10B), breaking the polymer weld and leaving the sheath 302 in position, and molten polymer 28 is delivered down the central cannulation of inner tube 308 and out of tip openings 310 (FIGS. 10C, 10D). The polymer bleeds out of the open end of sheath 302, and also out through the open structure of the mesh or braid, forming a "blob" 312a of polymer on top of the soft tissue and adhering the side walls of the sheath to the side walls of the opening in the soft tissue (FIG. 10D). The inner tube 308 is then withdrawn further, while continuing to deliver polymer through openings 310, filling the sheath with polymer and forming a "blob" 312b of polymer on the side of the soft tissue opposite blob 312a. Thus, the polymer defines a bolt-like anchor extending through the soft tissue.

To complete the procedure, the sheath is released from chuck 304 (FIG. 10G), the attachment 300 is removed, and any excess sheath material is snipped off (FIG. 10H).

Figure 11:
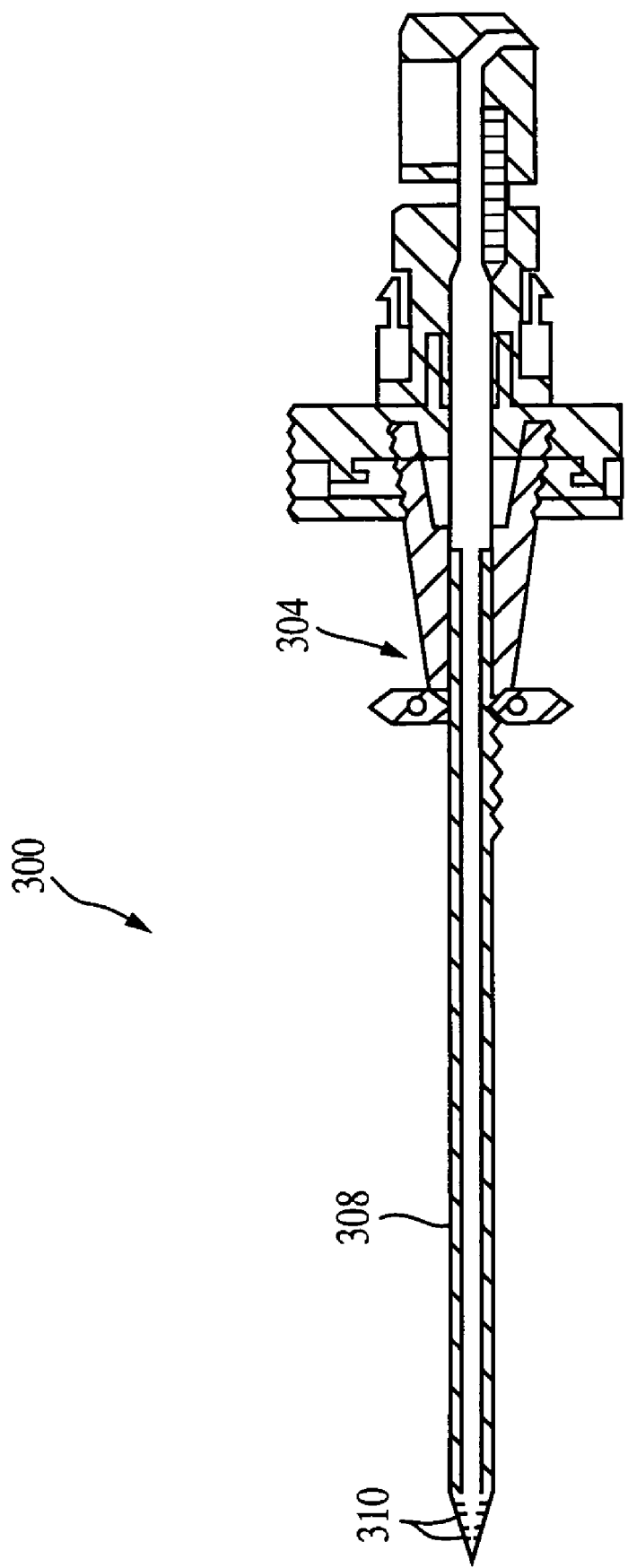
FIG. 11 is a cross-sectional view of a surgical instrument attachment suitable for use in the procedure of FIGS. 10–10H.

An attachment 300, suitable for use with handpiece 52 to form a surgical instrument 416, is shown in FIG. 11. Attachment 300 includes the components described above with reference to FIGS. 10–10H, and can be mounted on handpiece 52 in the same manner as attachment 54, discussed above.

Figure 12F:
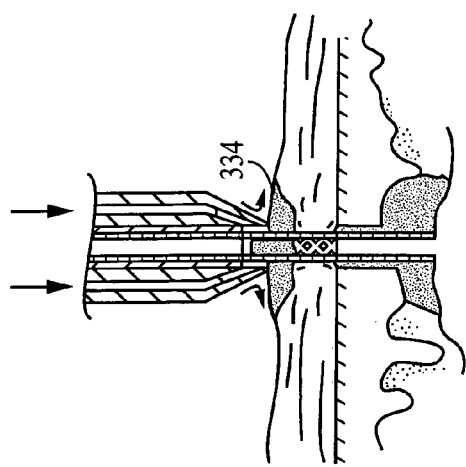
FIGS. 12–12I are diagrammatic views of another alternative procedure for fixing soft tissue to bone.
Figure 12G:
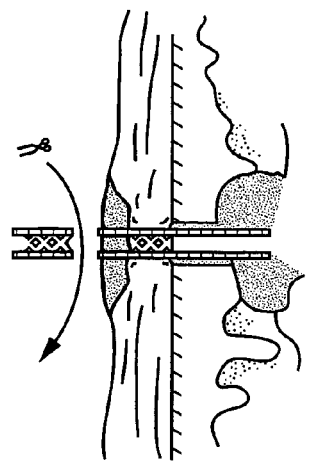
Figure 12H:
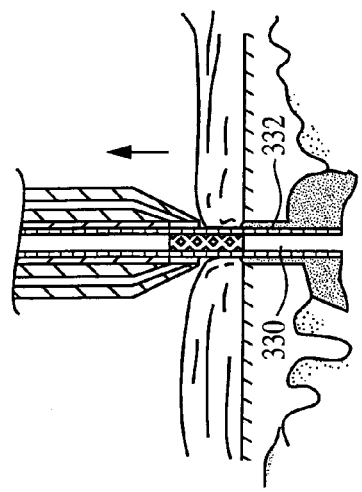
Figure 12I:
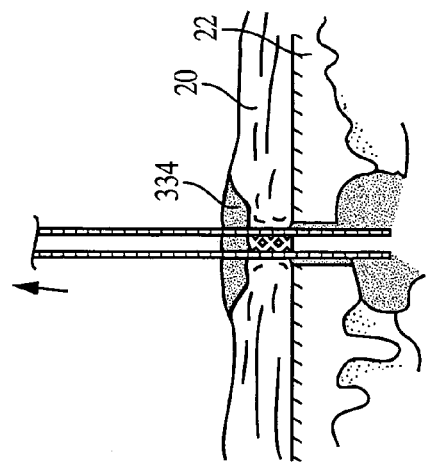

An alternative soft tissue to bone fixation procedure is shown in FIGS. 12–12I. In this procedure, a bone core is used to provide an osteoconductive medium within the polymeric anchor. This procedure is performed using a surgical instrument 516 that includes a cutting tool that is capable of forming in bone while leaving a bone core extending upward from the base of the opening. The surgical instrument 516 is constructed to deploy a tubular suture over the core, and deliver a polymer to the opening.

First, soft tissue is pierced, and a cavity is drilled (FIGS. 12–12B). The cavity is drilled using a cannulated cutting tool 331 that is constructed to leave a bone core 330 in the cavity (FIG. 12C). A flexible sleeve 332, e.g., a braided hollow suture, is deployed over the core 330, as shown in FIG. 12C. Polymer 28 is then delivered to the cavity (FIGS. 12D, 12E) around the sleeve 332 and core 330, and impregnates the sleeve 332. More polymer is delivered, while retracting the surgical instrument (FIGS. 12F, 12G), to form a blob 334 on the surface of the soft tissue, anchoring the soft tissue against the bone (FIG. 12H). Any excess sleeve material is then snipped off (FIG. 12I). The presence of the bone core in the anchor will tend to increase bone remodeling, and thus the suture may become embedded in bone more rapidly than would occur if the bone core were not present.

Another alternative soft tissue to bone fixation procedure is shown in FIGS. 13–13J. In this procedure, a suture is anchored in a cavity, using polymer, and a fixation device 340 is deployed around, and adhered to, the suture above the soft tissue to mechanically clamp the soft tissue in place. This procedure provides a low-profile anchor that may be useful in low clearance areas to prevent impingement. This procedure is performed using a surgical instrument 616 that includes a cutting tool to pierce soft tissue and form a cavity in underlying bone, a cannulated tube for delivery of a suture and polymer to the cavity and deployment of a fixation device around the suture, and a compounder to press the soft tissue against the bone and the fixation device against the soft tissue.

As shown in FIGS. 13–13C, soft tissue is pierced, a cavity is formed, and suture and polymer are delivered as discussed above, e.g., with regard to the procedures shown in FIGS. 2–2K. Next, while holding down the soft tissue with a compounder 335 (FIG. 13D), an expandable fixation device 340 is deployed around the suture to clamp the soft tissue in place (FIGS. 13E–13G). The expandable fixation device 340 includes a central region 341, having a bore 346, and a plurality of wings 354 extending radially from the central region. Wings 354 are joined to central region 341 by a plastic hinge having a memory that biases the wings toward an open position (FIG. 13F), while allowing the wings to be moved to a compressed position (FIG. 13E) so that the device can be deployed through a cannula. Thus, fixation device 340 is compressed and placed in delivery tube 339, with a suture 347 threaded through central bore 346, and is deployed by pressing down on the fixation device 340 with a cannulated probe 343 (FIGS. 13E–G). As the fixation device exits the compounder 335, the wings 354 expand outward to their normal position (FIG. 13F), and the compounder 335 presses the fixation device 340 down to flatten it against the soft tissue (FIG. 13G). Barbs 342 on wings 354 hold the fixation device 340 in place against the soft tissue, in its flattened position. The suture 347 is then snipped (FIG. 13H), and a blob of polymer 344 is delivered on top of the fixation device to cover bore 346 and adhere to the suture, anchoring the fixation device in place (FIGS. 13I and 13J). Preferably, fixation device 340 is formed of a resorbable plastic.

Many different types of cutting tools may be used in the procedures of the invention. Generally, it is preferred that the cutting tool not compact the bone fragments and debris into the side wall of the cavity, as this may impede infiltration of the polymer into the trabecular network surrounding the cavity. Thus, for example, a twist drill is generally preferred to a compacting drill. Some of the types of cutting tools that may be used are discussed below.

Figures 1, 14:
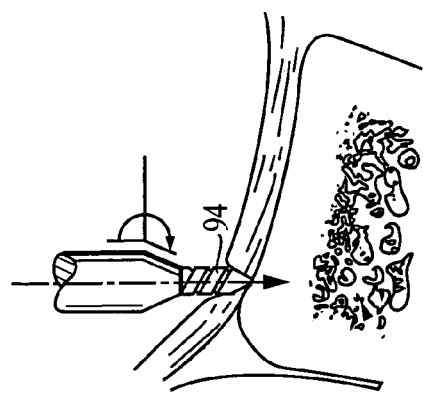
FIGS. 14–14D are diagrammatic views showing a cavity being drilled with a consumable drill bit.
Figure 14:
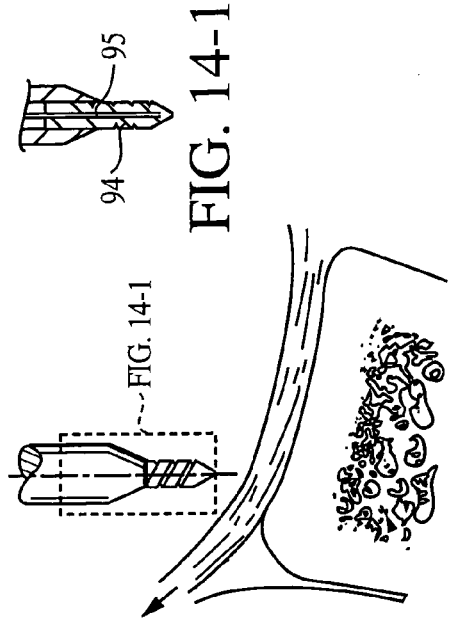
Figure 14A:
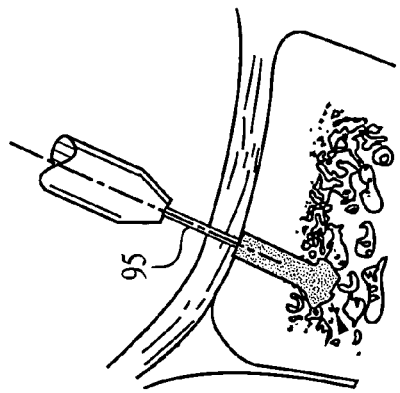
Figure 14C:
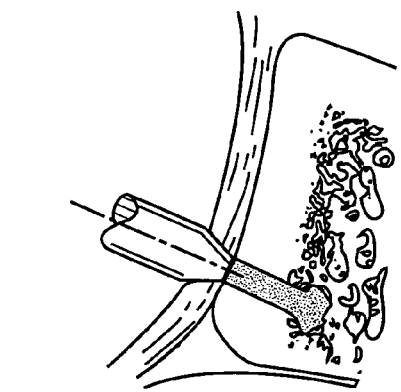
Figure 14B:
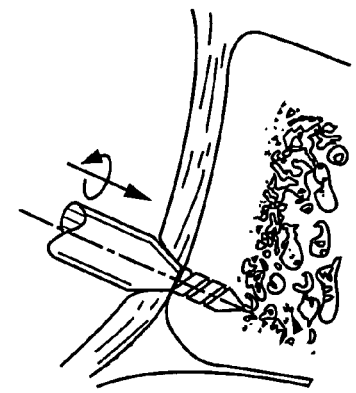
Figure 14D:
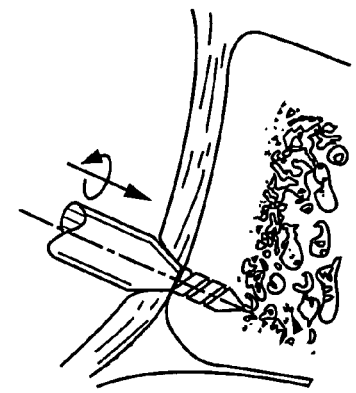

Referring to FIGS. 14–14D, the cutting tool may be a drill bit 94 that is consumable, i.e., the drill bit is formed of a polymer that melts during drilling (FIGS. 14B–14C), as a result of the heat generated by friction, to fill the cavity with molten polymer. A suture 95 is attached to the drill bit 94, so that the suture is delivered with the polymer and left behind when the surgical instrument is retracted (FIG. 14D). In this case, it is generally preferred that the drill bit be coated with a very thin layer of porous ceramic, just thick enough to provide the drill with sufficient hardness to penetrate the cortical bone and sufficiently thin so that the polymer will be able to melt during drilling. The ceramic can be applied by firing, plasma coating, deposition, or other suitable methods. Alternatively, a thin, hollow ceramic preform can be formed and then filled with polymer. Preferred polymers have a sufficiently low melting point to melt under drilling friction, and sufficient strength to contribute mechanical strength to the drill bit. The suture 95 may be conductive, to allow it to serve as a heating element to assist in melting the polymer if drilling does not generate sufficient heat.

FIGS. 15–20 show various suitable cutting tool geometries.

FIGS. 15 and 15A show a perforated drill 100, including openings 96 and sheath 98. Perforated drill 100 is useful when bone fragments/debris are to be collected for incorporation into the polymer (as discussed above with reference to FIGS. 4–4J), and when it is necessary that the cutting tool oscillate, rather than rotating (e.g., to avoid cutting or breaking a suture between stitches).

FIGS. 16–16A show a configured head 102, having a blade 103 that includes an opening 104 through which a suture can be threaded for delivery, and a barrel 105 defining a lumen 106 for suture and polymer delivery. Lumen 106 is generally substantially coaxial with opening 104.

Figure 17:
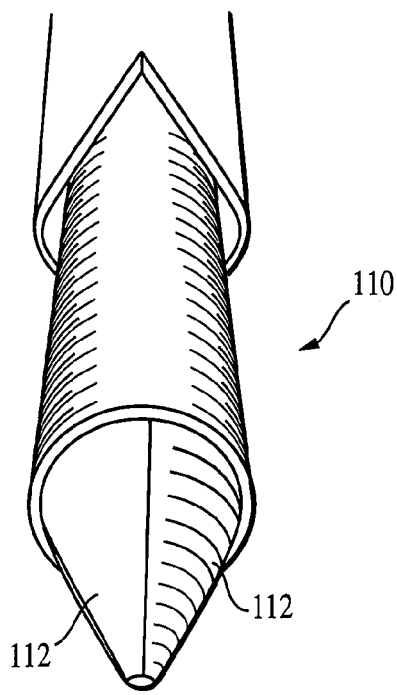
FIGS. 17 and 17A are perspective views of an alternative cutting tool in closed and open positions, respectively.
Figure 17A:
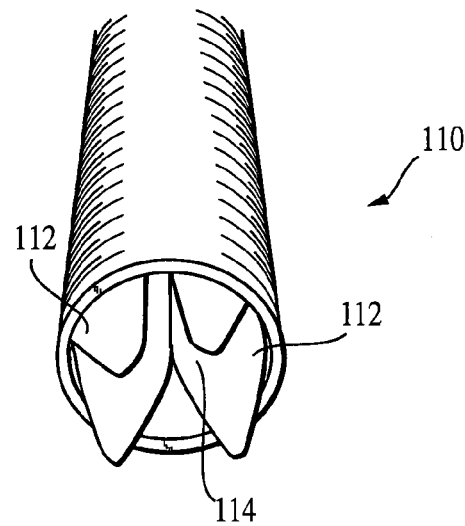

FIGS. 17–17A show an awl 110. Awl 110 includes a plurality of retractable "petals" 112, which when closed (as shown in FIG. 17) define a drill tip. When open (as shown in FIG. 17A), the petals 112 allow polymer and suture to be delivered through lumen 114. The petals may be opened and closed using a spring mechanism (not shown) or other suitable actuator.

Figure 18:
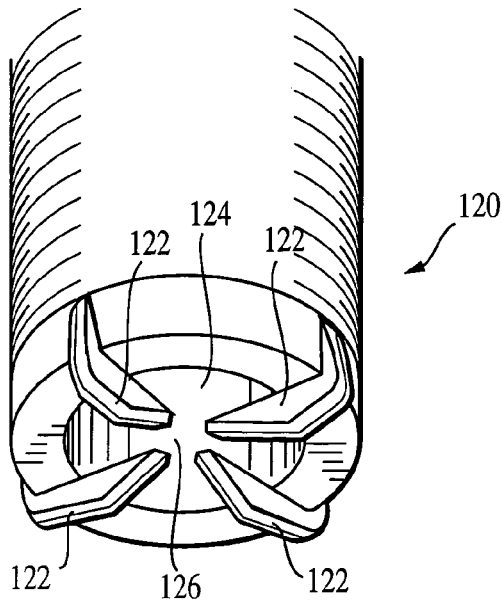
FIGS. 18 and 18A are perspective and front views, respectively, of an alternative cutting tool.
Figure 18A:
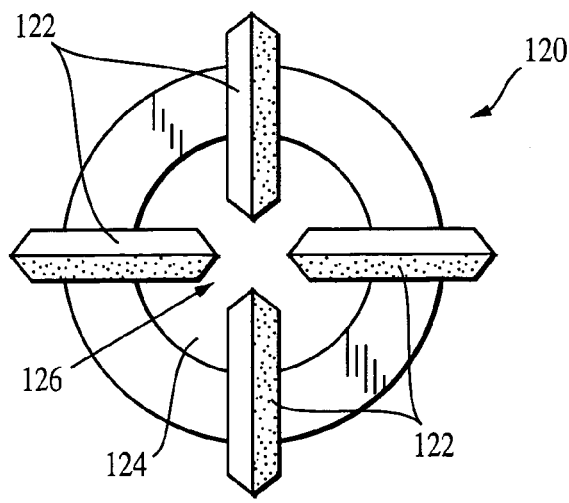

FIGS. 18–18A show a cutting head 120 having blades 122 radially extending crosswise across an open lumen 124. An open area between the blade tips defines an eyelet 126, to allow delivery of a knotted suture.

FIG. 19 shows a borer 126, including a plurality of serrated cutting/abrading tubes 128, a central lumen 130 through which polymer and suture can be delivered, and an extraction tube 132 for drawing bone fragments/debris away from the cutting site by suction. If desired, the contents of the extraction tube can be fed into the barrel of the borer, or elsewhere into the surgical instrument, at a location where the bone fragments/debris can be blended into the polymer prior to delivery of the polymer.

FIGS. 20–20B show a twist drill bit 134 having a delivery channel 136 for delivery of polymer and suture. The inner wall 138 of the delivery channel, in the vicinity of the tip 140 of the drill bit, may be abrasive, so as to break up the bone "core" 142 (FIG. 20B) if a bone core is not desired.

Cutting can also be accomplished using other techniques, such as laser, ultrasonic or water jet cutting. For example, water jet cutting could be performed using the saline supply that is present in the operating room. In this embodiment, a dynamo generator would be included in the surgical instrument, to power the water jet, and the surgical instrument would include an adaptor to allow the saline supply to be plugged in to the surgical instrument. Other suitable techniques include crush indentation, hot needle drilling, thermally degrading the bone, e.g., with RF ablation, and cryogenic freeze fracturing. In some implementations, it is preferred that the cutting method be capable of forming a very small diameter cavity, e.g., less than 2 mm and preferably less than 1.5 mm. To form such a small diameter cavity, cutting may be performed using microtooling. Because a conventional bone anchor is not needed in many of the procedures of the invention, the cavity can be made smaller than the diameter of such anchors, thereby preserving more cortical bone, limiting trauma, and potentially improving the pull-out strength of the anchor. When a very small diameter cavity is used, e.g., less than 3 mm, the cortical bone will tend to grow back over the cavity, further increasing the strength of the anchor.

While in the embodiments discussed above the polymer is generally provided in the form of a powder or pellets, the polymer may be provided in any desired form. For example, the polymer may be contained in a cartridge that can be heated using equipment that is available in the operating room, e.g., an autoclave or heated bath. Thus, the cartridge can be preheated prior to surgery, and then inserted into a surgical instrument (not shown) that is adapted to puncture the cartridge for delivery of the polymer. The polymer may also be provided as a rod, or in the form of fibers or strands to increase its surface area and thereby decrease melting time.

The polymer can be heated using any suitable method. Preferred methods will heat the polymer in a controlled manner, to a temperature just above its melting temperature, to avoid overheating and possible thermal trauma to the tissue and bone at the delivery site. To expedite the surgical procedure, it is preferred that heating occur within 2 minutes or less, unless the polymer is provided in a cartridge and is pre-heated, e.g., in an autoclave. One suitable method is to provide a heating element in the surgical instrument, as discussed above. Preferably the heating element is thermostatically controlled to prevent overheating of the polymer. Other suitable heating methods include ultrasound (which may also be used to form the cavity), use of the drive mechanism of the surgical instrument to heat the polymer, use of a conductive suture embedded in the polymer as a heating filament, laser (e.g., by including an indicator dye in the polymer and using a laser frequency that would not burn the tissue at the delivery site but would melt the polymer), and radio frequency and induction heating.

The suture material, if a suture is used, may be resorbable or non-resorbable. It is generally preferred that the suture material be braided, rather than mono filamentary, for greater surface area and surface roughness, to enhance pull-out strength. However, monofilament may be used if desired. A loose braid is generally preferred, as the spaces in the braid enhance polymer infiltration. A "bird's nest" arrangement of suture can also be formed by feeding suture out into the cavity and allowing it to pile up loosely in the cavity. Preferably, the suture does not include a polymeric coating. Suitable suture materials include polyesters, polyamides, e.g. Nylon, polybutester, polyglycolic acid, polyglyconate, poly-L-lactic acid and polydioxanone. It is generally preferred that the suture have a high tensile strength, i.e., sufficient strength so that the mode of failure during pull-out testing is not premature suture failure.

The suture may also include any desired feature or augmentation. For example, the suture may include one or more of the suture augmentations shown in FIGS. 21–21G i.e., a knot 400 or knot bundle 402 (FIGS. 21 and 21D), a sphere 404 (FIG. 21C and 21E), a shaped element 406, e.g., a larger diameter portion (FIG. 21A), a flexible 4-way connector 408 (FIG. 21B) or a t-bar 412 (FIG. 21G), or a plurality of barbs 410 (FIG. 21F). If positioned on top of the soft tissue after the suture is anchored in place, the suture augmentations shown in FIGS. 21–21G may secure the soft tissue in place against the bone. If positioned in the cavity and surrounded by polymer, these features may increase the resistance of the suture to pull-out. Other features that will provide these or other functions may also be used.

Many other types of surgical instruments may be used to perform the procedures described above. For example, an alternative surgical instrument 420 is shown in FIGS. 22–32 and described in detail below. Using this surgical instrument, the suture can be easily tensioned between stitches, fed from the surgical instrument in a controlled manner, and positioned precisely in the bone hole.

Figure 22:
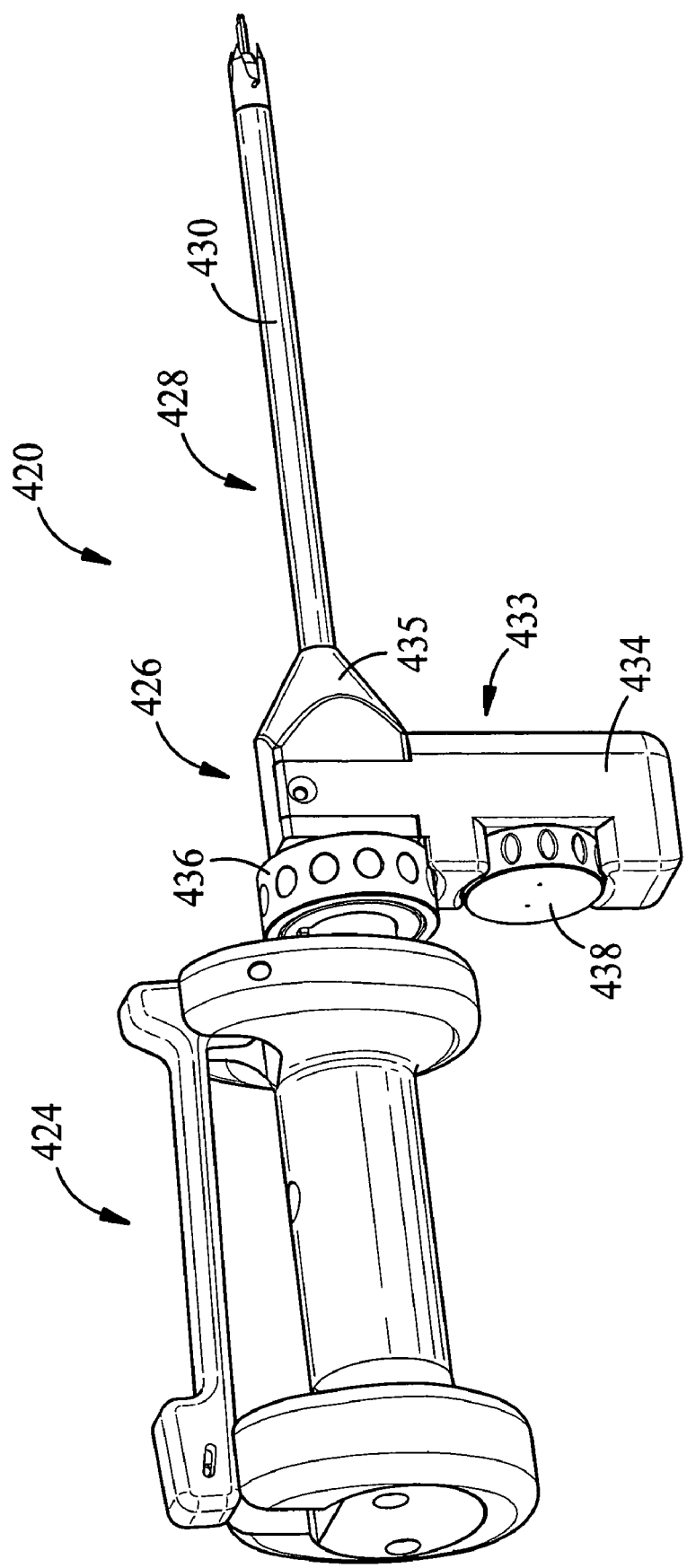
FIG. 22 is a perspective view of a surgical instrument according to an alternate embodiment of the invention.
Figure 23:
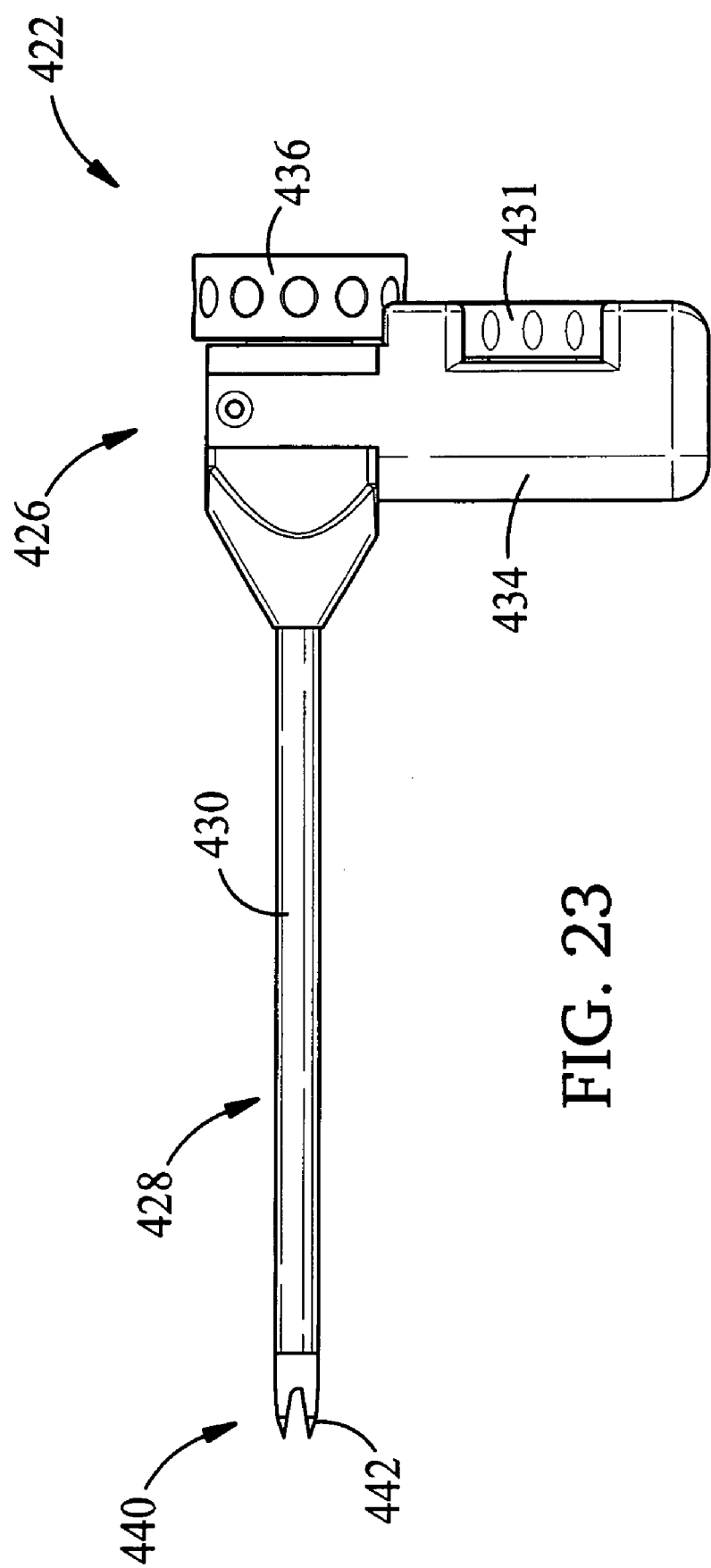
FIG. 23 is a side view of a suture control assembly portion of the surgical instrument of FIG. 22.

Referring to FIG. 22, surgical instrument 420 includes a suture control assembly 422 and a polymer delivery assembly 424. The suture control assembly 422 is used by itself, without the polymer delivery assembly 424 (as shown in FIG. 23) to position, tension and feed the suture material. The suture control assembly 422 includes a suture tensioning device 426 that maintains the desired level of tension on the suture and controls the position of the suture, and a feed tube assembly 428 through which the suture travels to the hole. The feed tube assembly 428 includes an outer tube 430, shown in FIG. 22, and other tubes, within the outer tube 430, that will be described below.

The polymer delivery assembly 424 is mounted on the suture control assembly 422 by the surgeon, to position the suture in a hole in bone and deliver a polymer to the hole. The feed tube assembly 428 defines a lumen 432 that is dimensioned to receive a delivery tube assembly 522 (FIG. 29) of the polymer delivery assembly 424 when the polymer delivery assembly is mounted on the suture control assembly as shown in FIG. 22. Lumen 432 is also dimensioned to receive a drill bit (not shown) for drilling a hole in bone. The structure and function of the suture control assembly and polymer delivery assembly will be discussed in turn below.

Referring to FIG. 23, the suture control assembly 422 includes a housing 434 that includes a handle portion 433 that is configured to be held by a surgeon, on which are positioned a suture lock/displacement knob 436, and a manual tensioning knob 438. Housing 434 also includes a mount portion 435, from which the feed tube assembly 428 extends to a distal end 440 that includes points 442 for piercing and holding soft tissue. The outer tube 430 is fixedly mounted on the mount portion 435.

Figure 23A:
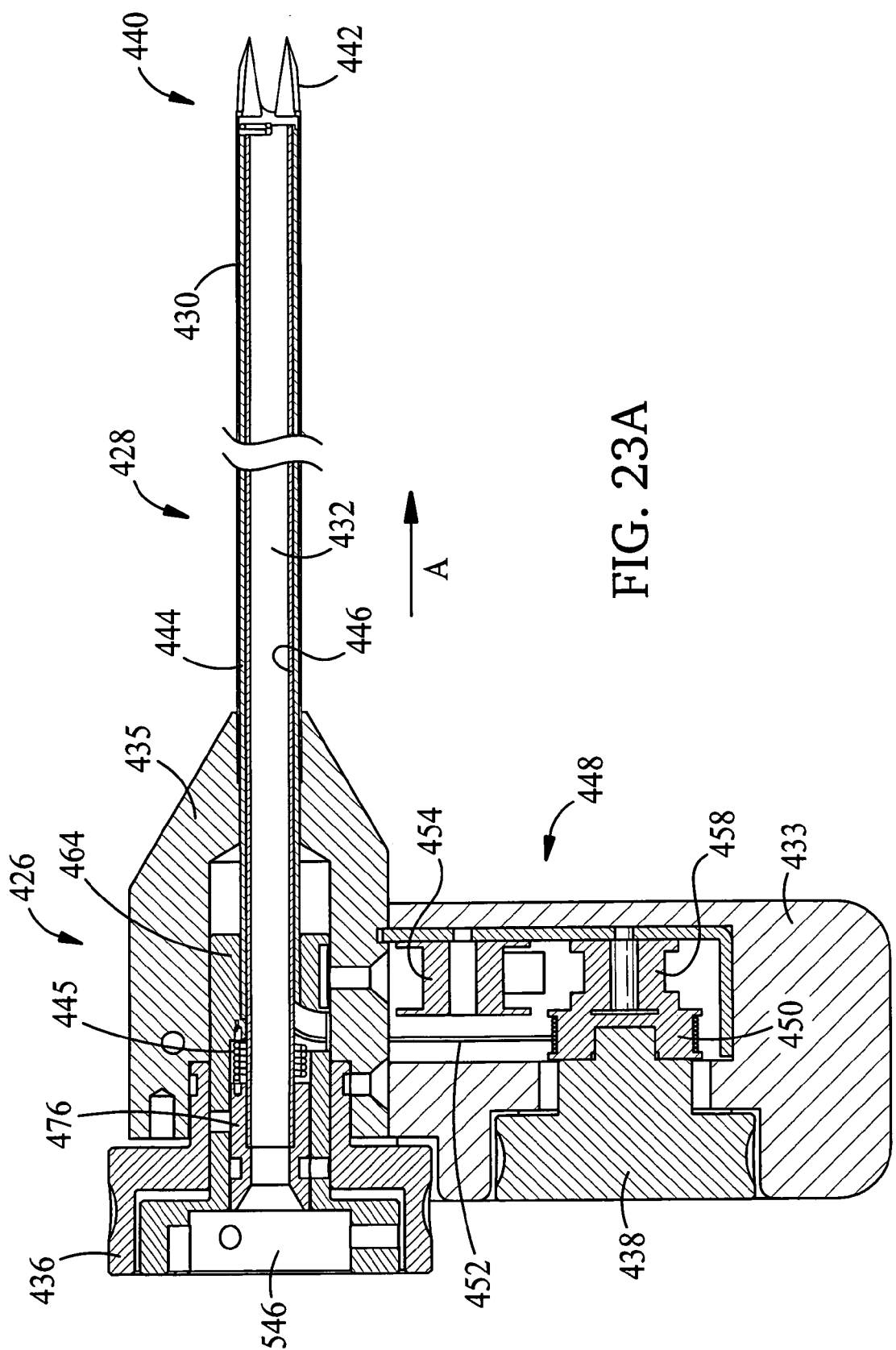
FIG. 23A is an enlarged cross-sectional view of the suture control assembly shown in FIG. 23.
Figure 25A:
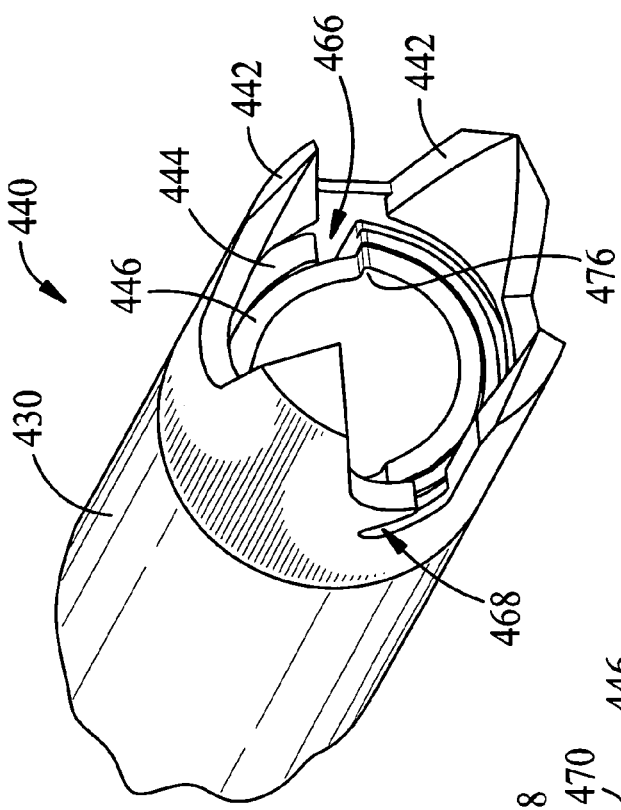
FIGS. 25 and 25A are highly enlarged perspective views, taken from different angles, of the distal end of the suture control assembly of FIG. 23.

Referring to FIGS. 23A and 25A, the feed tube assembly 428 further includes a suture delivery tube 444 (FIGS. 26, 26A) and a suture displacement tube 446 (FIG. 27, 27A), nested within the outer tube 430. Suture delivery tube 444 is interposed between suture displacement tube 446 and outer tube 430. The delivery tube 444 and displacement tube 446 are mounted for movement relative to the outer tube 430. Suture delivery tube 444 is constructed to guide the suture through the feed tube assembly and lock the suture in place at distal end 440. Suture displacement tube 446 is constructed to control the position of the suture at the distal end 440. These functions will be discussed in detail below.

Figure 24:
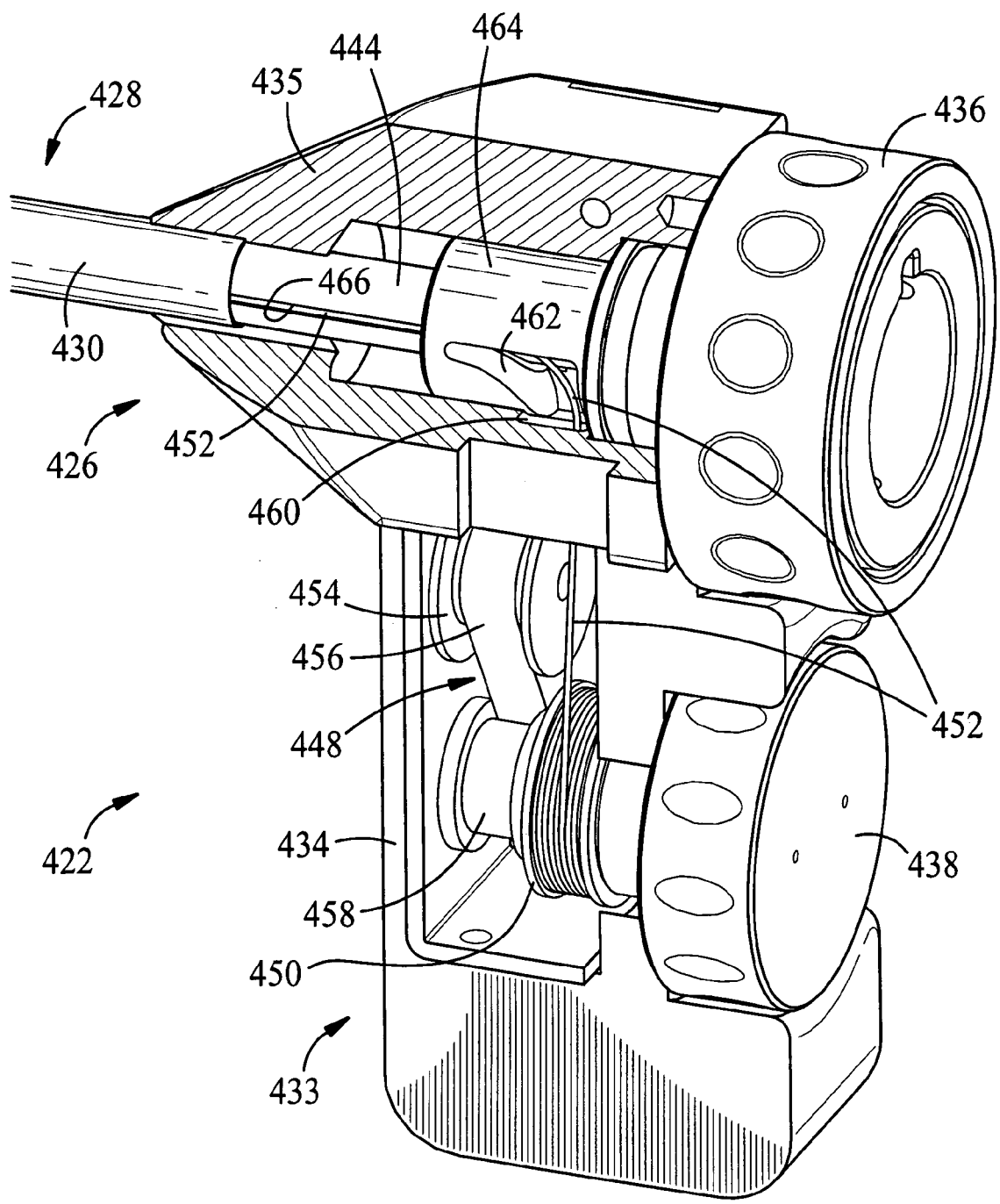
FIG. 24 is an enlarged perspective view of the suture control assembly of FIG. 23, with a portion of the housing removed.

The suture is tensioned by a spring control device 448. Referring to FIGS. 23A and 24, spring control device 448 includes a suture spool 450, on which is wound a supply of suture 452, a spring spool 454, and a constant force spring 456 extending between an extension 458 of the suture spool and the spring spool 454. The spring 456 maintains a constant tension on the suture 452 as it is fed out of the suture control assembly. The surgeon can manually apply additional tension, as desired, by rotating the manual tensioning knob 438, which is mounted on the suture spool 450.

Figure 25:
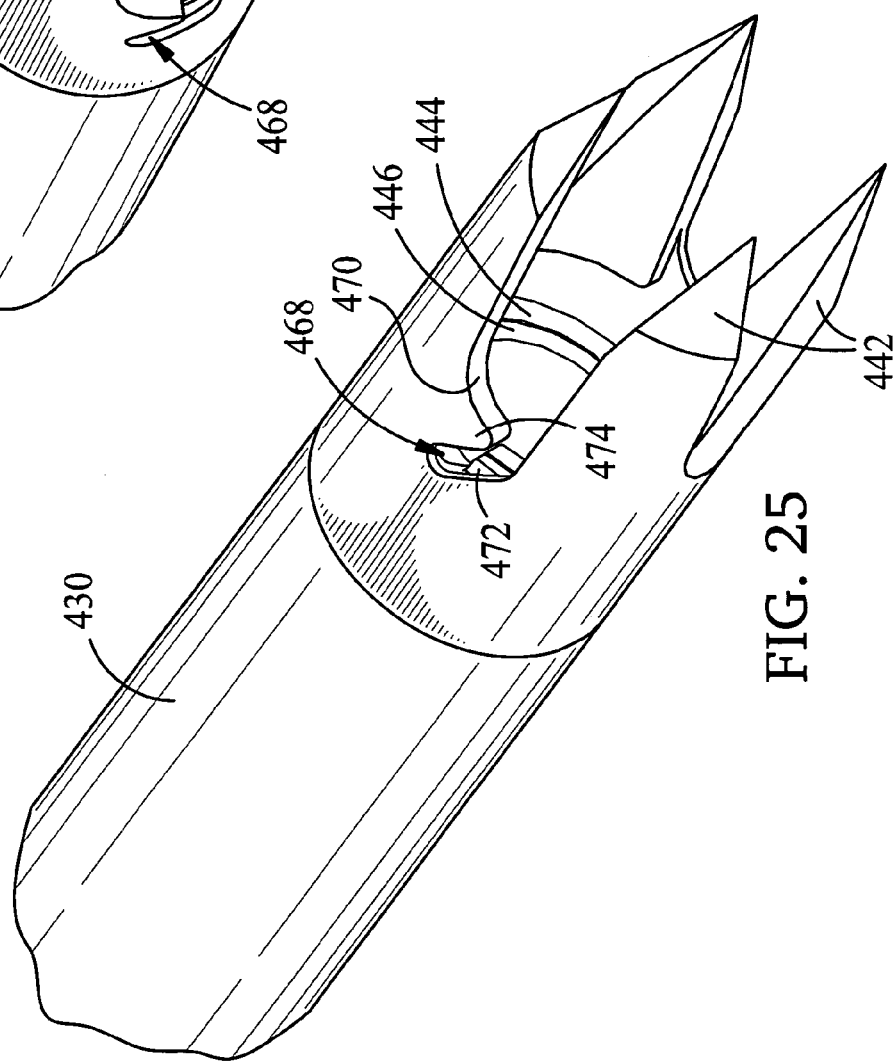
Figure 28:
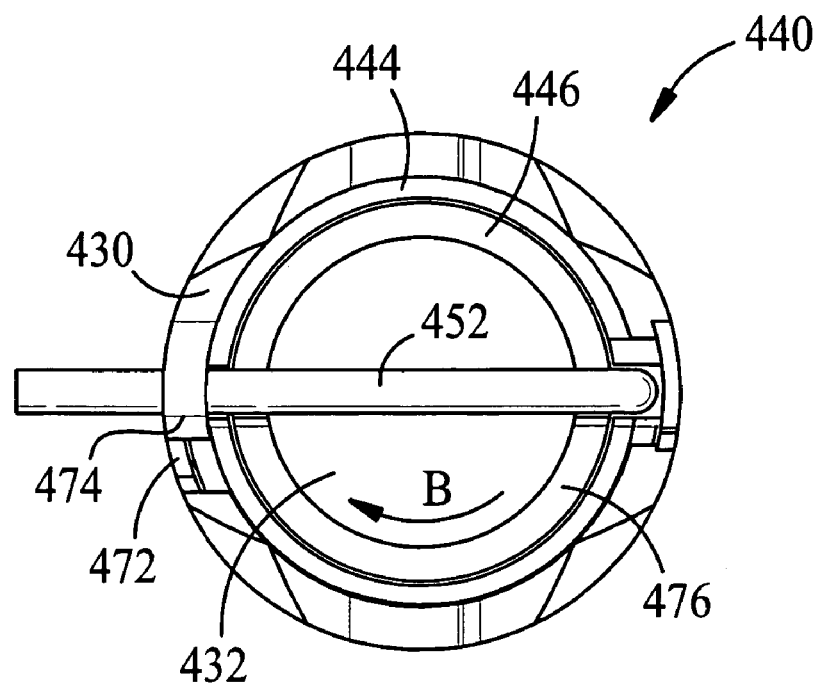
FIGS. 28 and 28A are schematic end views of the distal end of the suture control assembly, showing movement of a suture from a first position to a second position.
Figure 33:
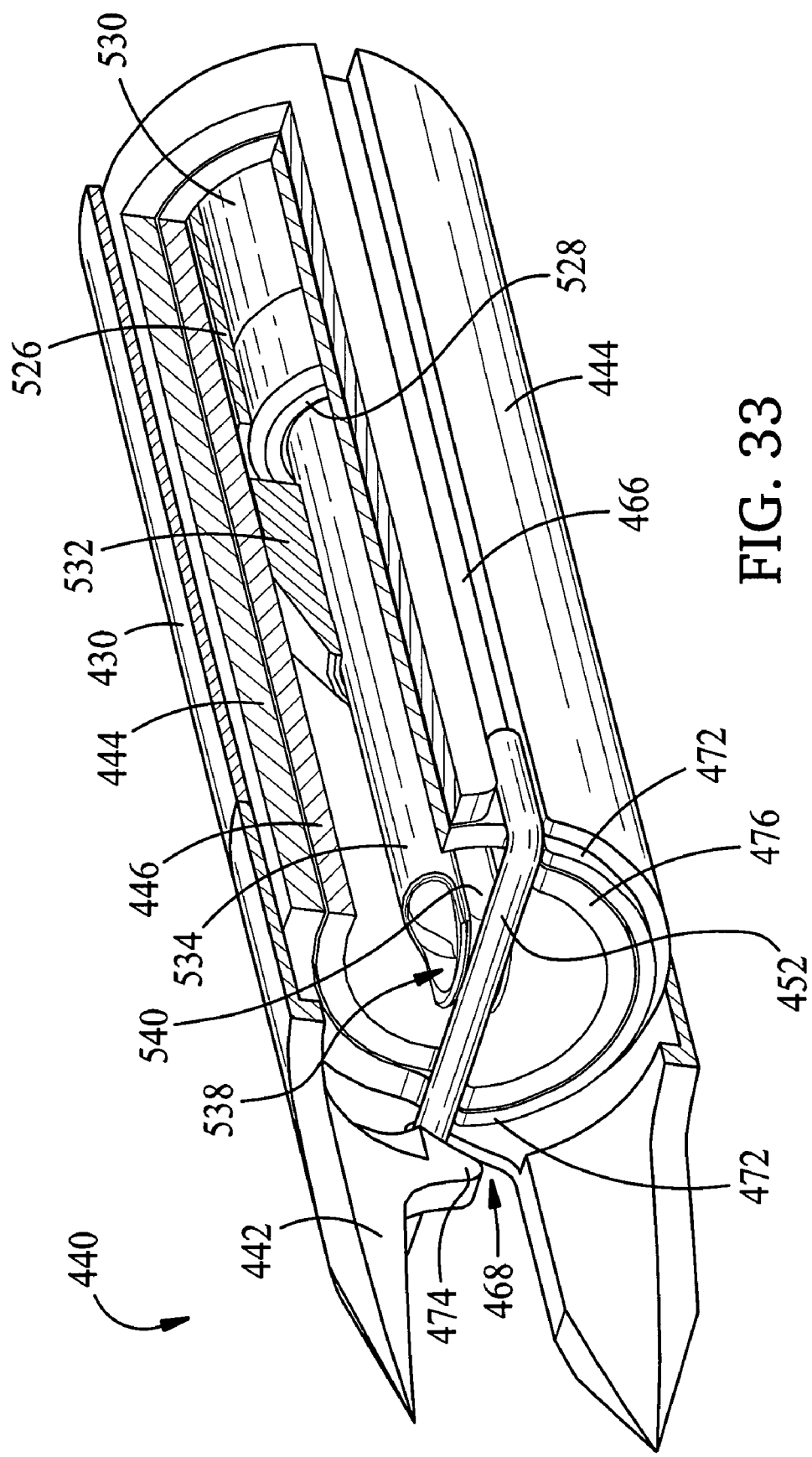
FIG. 33 is a highly enlarged perspective view, in partial cross-section, of the distal end of the surgical instrument of FIG. 22.

As shown in FIG. 24, the suture 452 feeds upward from the suture spool 450 through an opening 460 in the mount 435 and an opening 462 in the mount 464 at the proximal end of the suture delivery tube 444 (FIG. 26) and into a guide channel 466 that extends the length of the suture delivery tube 444. The suture 452 travels along the guide channel 466, exiting at the distal end 440 of the suture control assembly 422 (FIGS. 25A, 33). When it exits at the distal end 440, the suture may be drawn by the surgeon across the center of the lumen 430, as shown in FIGS. 28 and 33, and into slot 468 in outer tube 430 (FIGS. 25, 25A), guided by the smooth radius of surface 470 (FIG. 25). The angle of the slot 468 helps to hold the suture 452 in place.

The suture is locked in place (captured in slot 468) by advancing the suture delivery tube 444 distally (arrow A, FIG. 23A), so that lip 472 of the delivery tube 444 (FIGS. 25, 26A) contacts the upper edge 474 of slot 468 (FIGS. 25, 28). This locking of the suture prevents the suture from being drawn up into the suture delivery assembly by the tension applied by the spring control device 448. This feature allows the surgeon to cut the suture in between stitches and/or when stitching is completed, without losing the suture. Importantly, the locking function also allows the surgeon to lock in the desired tension between stitches, e.g., after manually setting the tension using the manual tensioning knob 438. Additionally, the locking function keeps the suture from falling out of the slot 468.

Figure 26:
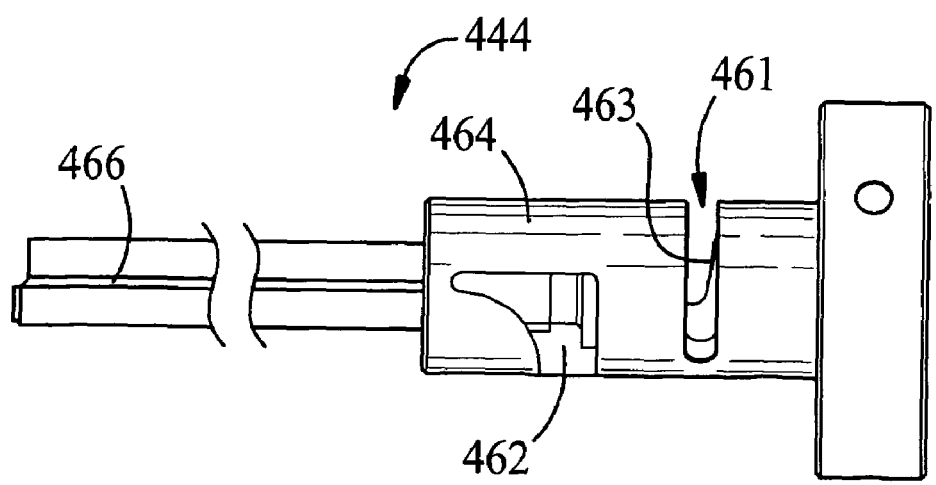
FIG. 26 is a side view of the suture delivery tube of the suture control assembly.
Figure 26A:
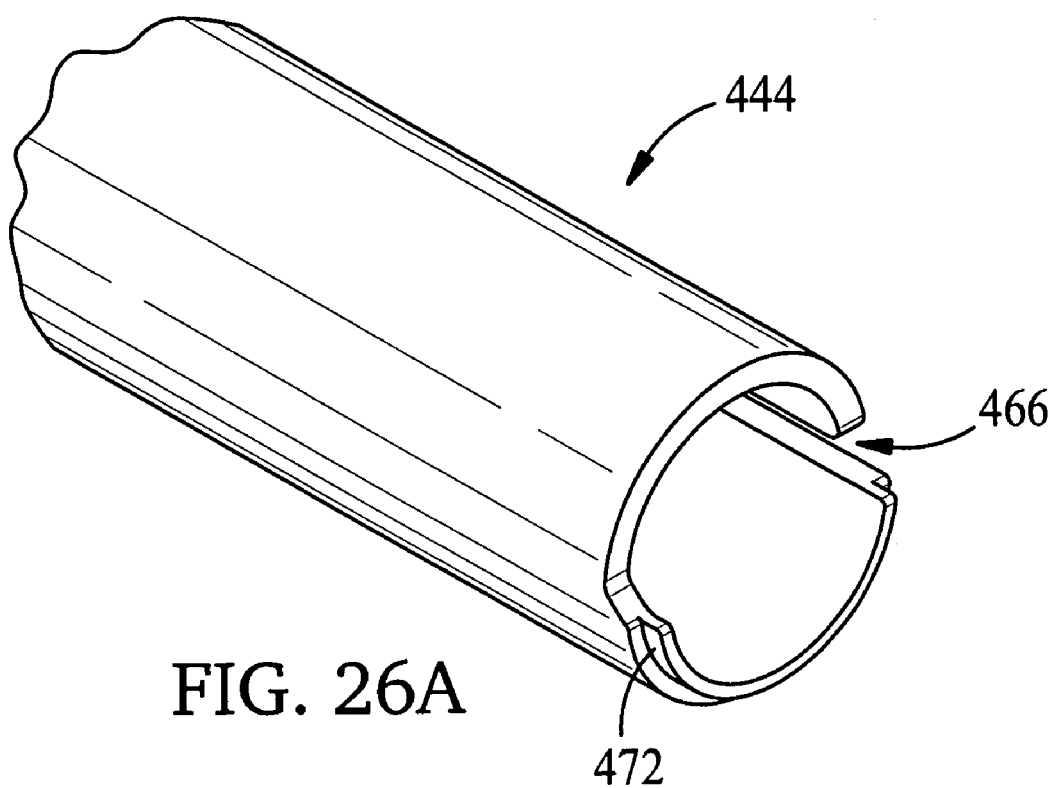
FIGS. 26A and 27A are highly enlarged perspective views of the distal ends of the suture delivery and suture displacement tubes, respectively.

Referring to FIGS. 23A and 26, the delivery tube 444 is advanced distally by turning the suture lock/displacement knob 436 through a 45° arc. The mount 464 at the proximal end of the delivery tube 444 is pinned (not shown) so that it cannot rotate. A pin (not shown) extends from the knob 436 into a helical slot 461 in the mount 464 (FIG. 26). Thus, when the knob 436 is rotated 45 degrees, the pin engages the arcuate camming surface 463 of the helical slot and forces the delivery tube 444 forward. When the knob 436 is rotated in the opposite direction, the engagement of the pin with the camming surface 463 causes the delivery tube to retract.

Figure 27A:
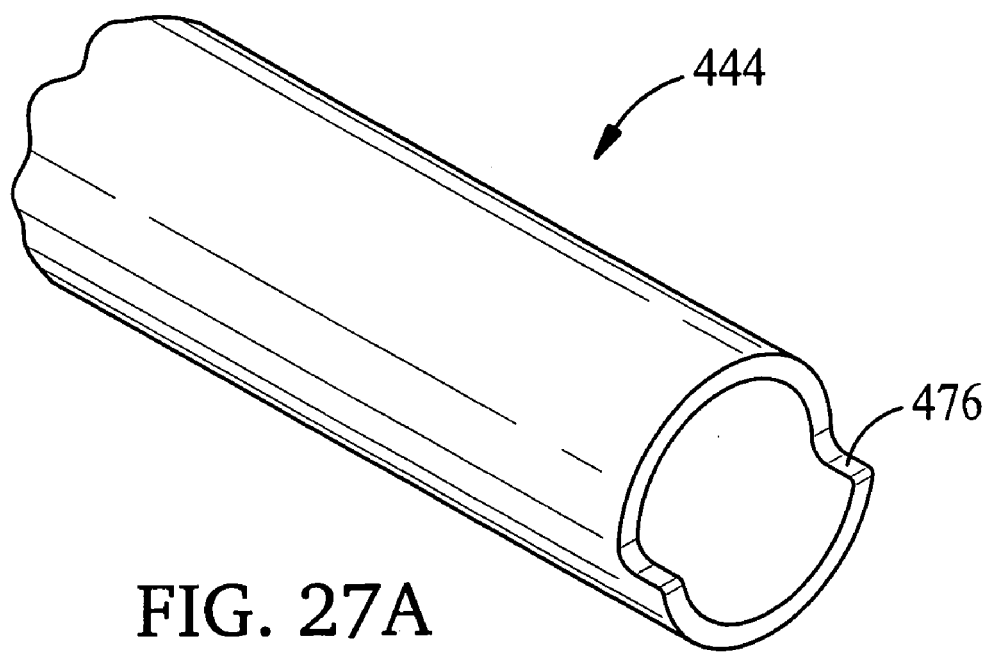
Figure 28A:
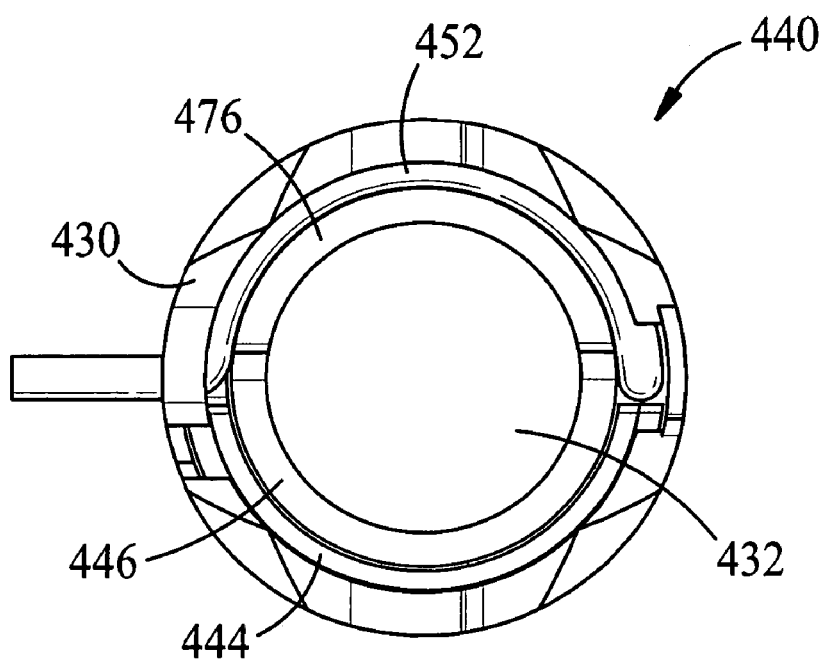

In order for the surgeon to drill a hole in bone, it is necessary to displace the suture 252 out of the center of lumen 432, so that a drill bit can be inserted through the lumen. The suture is shown in this displaced position in FIG. 28A. To displace the suture, the suture displacement tube 446 is rotated 180 degrees (arrow B, FIG. 28). This causes lip 476 of the suture displacement tube (FIG. 27A) to contact the suture 452 and push it upward, as shown in FIG. 28A.

Figure 27:
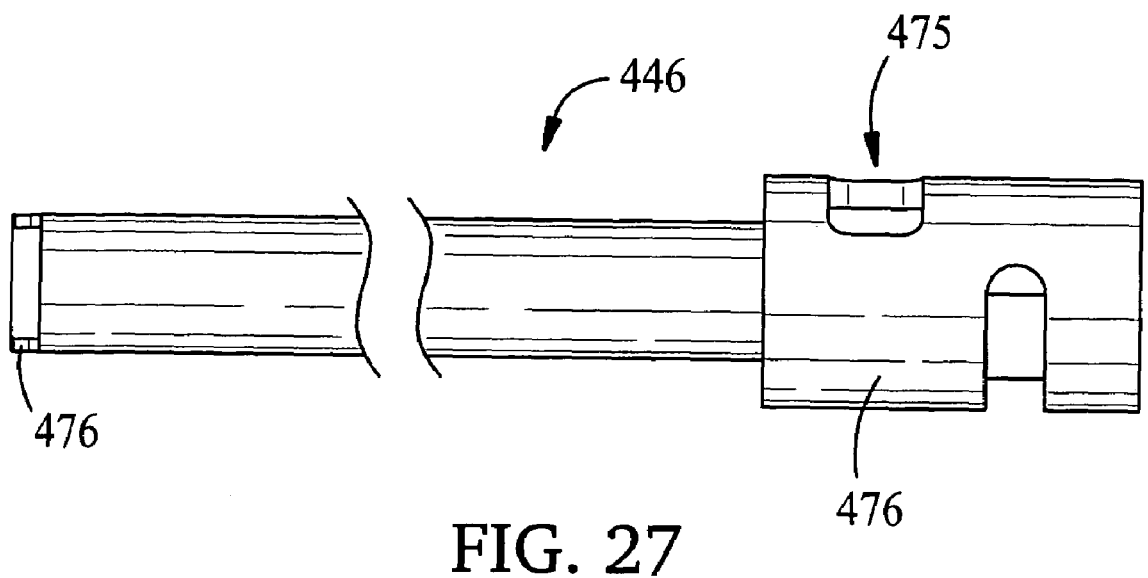
FIG. 27 is a top view of the suture displacement tube of the suture control assembly.

Referring to FIGS. 23A and 27, the suture displacement tube 446 is rotated by turning the suture lock/displacement knob 436 an additional 180 degrees. The same pin that extends from the knob 436 into the slot 461 in the delivery tube extends further, into a slot 475 in a mount 476 at the proximal end of the displacement tube 446. This slot 475 is sufficiently short circumferentially so that the pin will bottom out at one end of the slot after the knob has rotated the first 45 degrees needed to lock the suture, as discussed above. Once the pin bottoms out in the slot, the pin will engage the bottom of the slot to rotate the displacement tube 446. Detents are provided (not shown) to indicate to the surgeon when the knob 436 has been turned 45 degrees and 180 degrees.

A return spring 445 provides a rotational biasing force that biases the suture displacement tube to its normal position (the position shown in FIG. 28). Without the biasing spring, when the knob 436 is rotated back 180 degrees, to the "locked but not displaced" the suture displacement tube would be 45 degrees behind its normal position. The spring 445 provides the additional force needed to return the suture displacement tube to its normal position without moving the knob 436 all the way to the unlocked position. As a result, the suture can be moved from the position shown in FIG. 28A to the position shown in FIG. 28 without unlocking the suture. The advantages of this feature will be apparent when the stitching procedure is discussed below.

Figure 29:
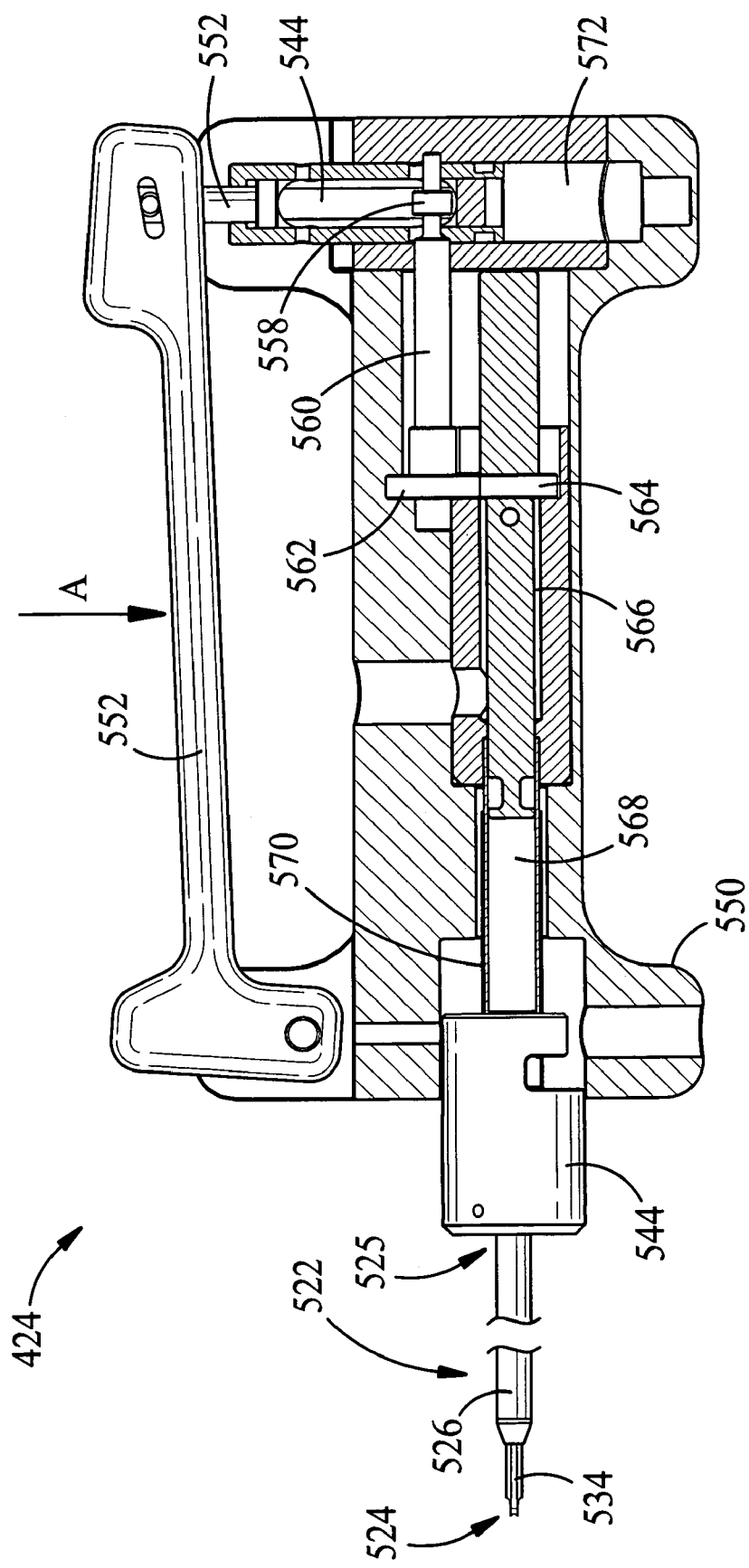
FIG. 29 is an enlarged cross-sectional view of a polymer delivery assembly portion of the surgical instrument shown in FIG. 22.

As shown in FIG. 29, the polymer delivery assembly 424 includes a delivery device 520 (shown in detail in FIG. 32) and a delivery tube assembly 522. These components will be discussed in turn.

Figure 30:
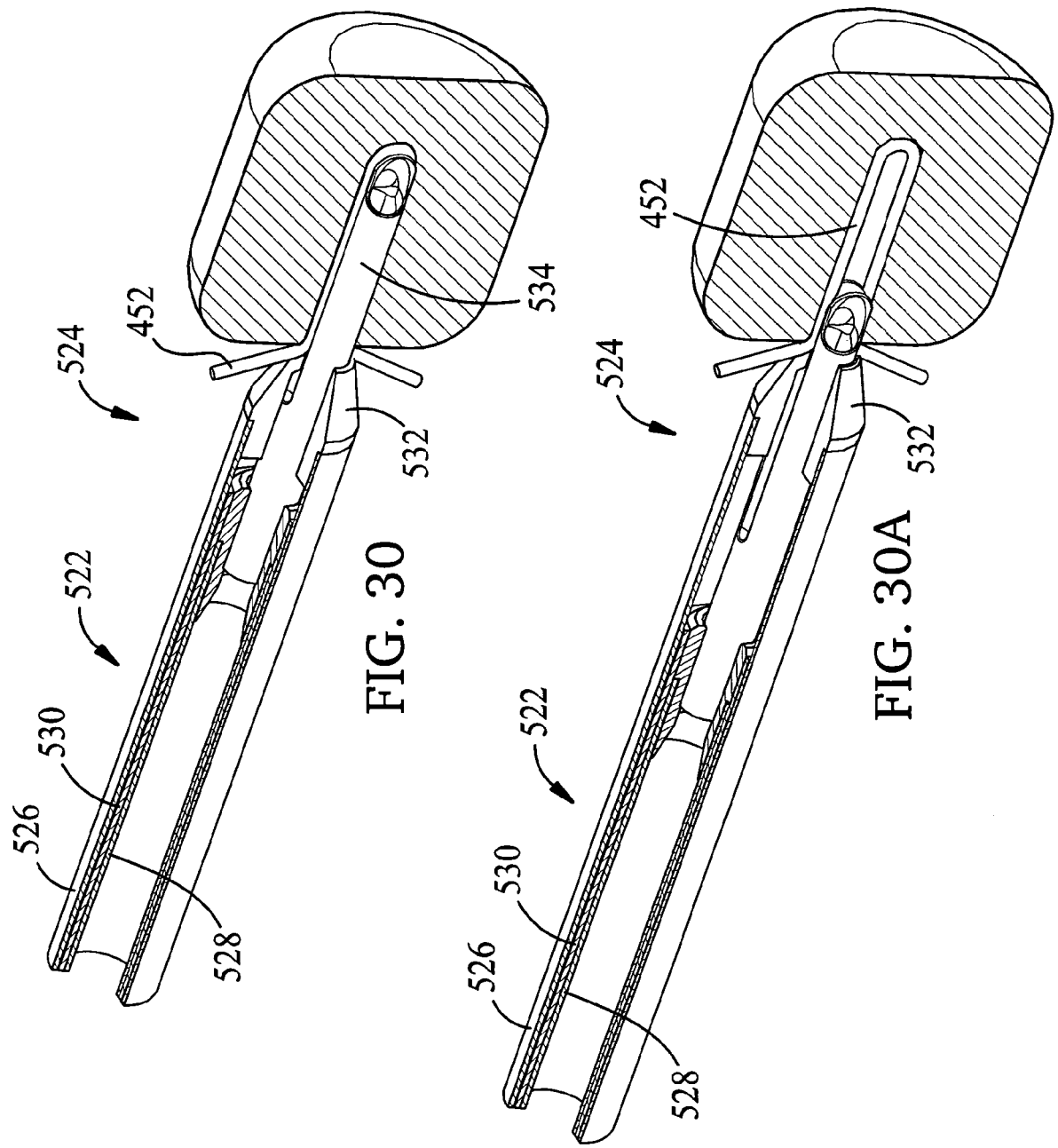
Figure 31:
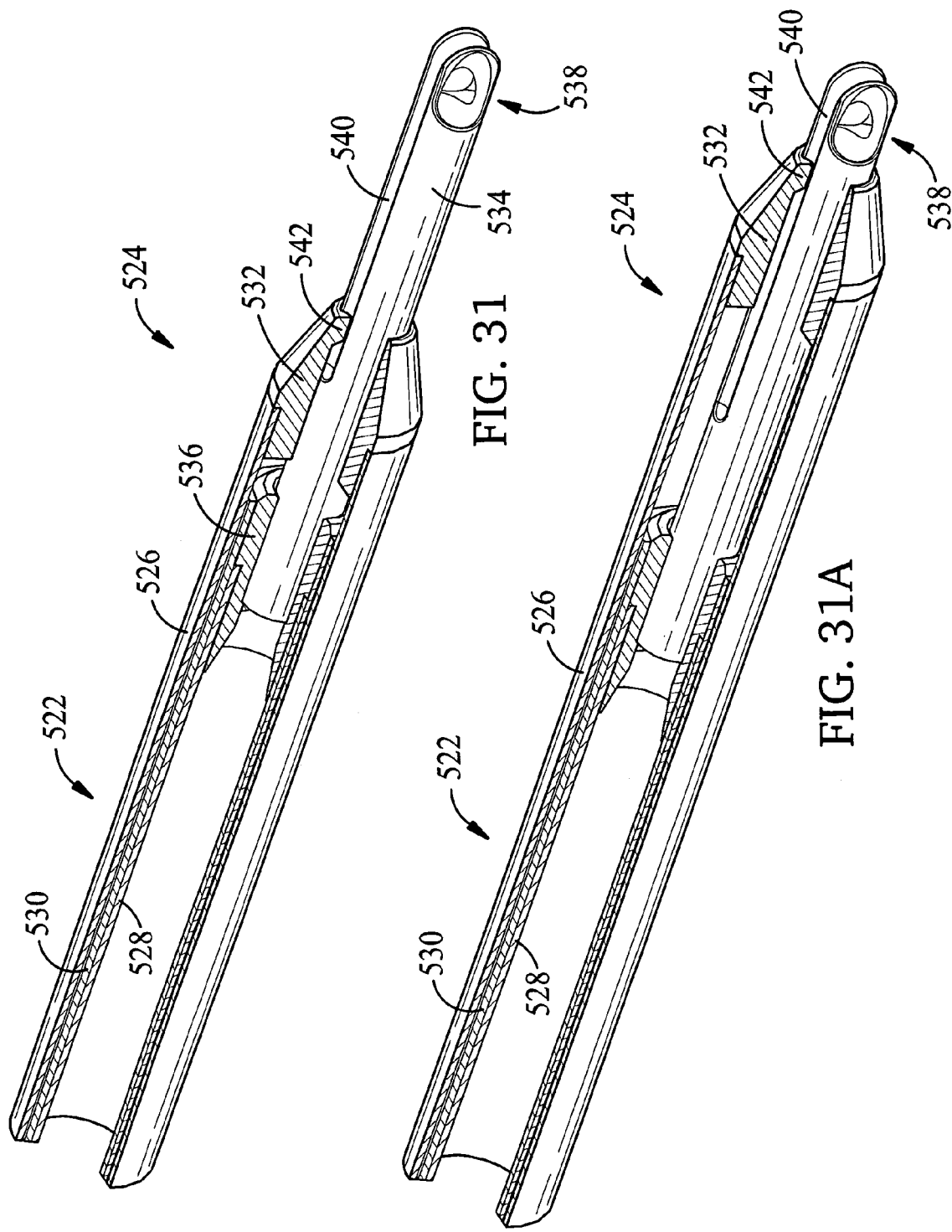

FIGS. 30–31A show detailed views of the distal end 524 of the delivery tube assembly 522, partly broken away to show the various components of the assembly. The suture feed tube assembly 428, which would surround the delivery tube assembly 522 when the surgical instrument is in use, is omitted in FIGS. 30–31A for clarity. The delivery tube assembly 522 is shown in place within the feed tube assembly 428 in FIG. 33.

Referring to FIGS. 30–31A, the delivery tube assembly 522 includes an outer guide tube 526, an inner polymer delivery tube 528, and, disposed between these two tubes, a heating element 530, e.g., a tube of etched foil. An insulating shield 532 is disposed at the distal end of the guide tube 526. A nozzle 534 is mounted on an attachment member 536 at the distal end of the delivery tube 528. During use of the surgical instrument, the nozzle 534 is moved between an extended position (FIGS. 30 and 31) and a retracted position (FIGS. 30A and 31A), as will be discussed in detail below.

Referring to FIGS. 31 and 31A, nozzle 534 is hollow, to receive polymer that flows through the delivery tube 528, and includes openings 538 through which polymer can exit the nozzle. The nozzle also includes a longitudinal groove 540, which allows the nozzle to be guided in a sliding motion by a corresponding ridge 542 on the insulating shield 532. Groove 540 also serves to carry the suture 452, as shown in FIGS. 30 and 33.

Figure 32:
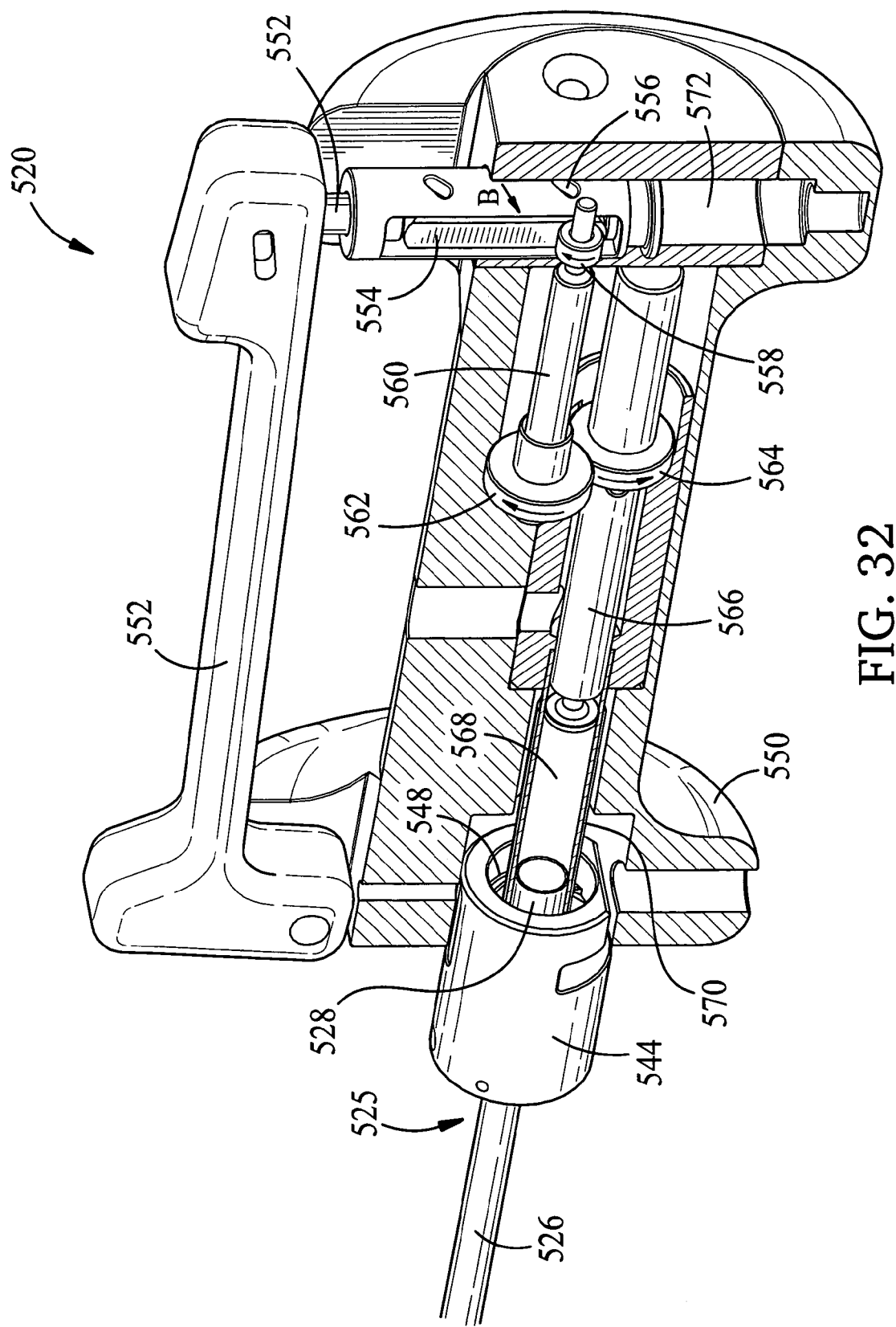
FIG. 32 is an enlarged perspective view of a polymer delivery device portion of the polymer delivery assembly shown in FIG. 29 with a portion of the housing removed to show the internal components of the assembly.

The polymer delivery device 520, shown in detail in FIGS. 29 and 32, includes a mechanism for extending the nozzle, and thus advancing the suture into the hole, and a mechanism for delivering a metered amount of polymer.

With regard to the extension of the nozzle, the proximal end 525 of the outer guide tube 526 is mounted on a spring-loaded cover member 544, which allows the outer guide tube 526 to retract with respect to the nozzle 534 in response to pressure applied to the cover member 544. When the surgeon mounts the polymer delivery assembly 424 on the suture control assembly 422, as shown in FIG. 22, the cover member 544 seats in a receiving member 546 of the suture control assembly 422 (FIG. 23A). As the surgeon presses the two assemblies together, the spring 548 (FIG. 32) within the cover member 544 is compressed, causing the outer guide tube 526 to retract and thereby extending the nozzle 534 relative to the guide tube.

The mechanism for delivering a metered amount of polymer will now be described, with reference to FIGS. 29 and 32. Polymer delivery device 520 includes a housing 550, and, mounted on the housing, a trigger 552 that is operable by the surgeon using a squeezing motion. Squeezing the trigger (arrow A, FIG. 29) depresses shaft 552, which in turn depresses a toothed gear rack 554. As the gear rack moves downward, it is also pushed forward (arrow B, FIG. 32) by a pair of pins (not shown) that protrude from the sides of the rack and engage corresponding angled guide slots 556 in the housing (FIG. 32). This forward movement causes the gear rack to engage, and simultaneously turn, a gear 558. Shaft 560 transmits this rotation to gear 562, which in turn rotates gear 564 in the opposite direction. Gear rack 554 and gears 558, 562 and 564 are configured so that one complete squeeze of the trigger will result in one full rotation of each gear.

Gear 564 has a threaded inner surface, and is mounted on a plunger 566 having a threaded outer surface. Gear 564 is held in place by a retainer (not shown) so that it will rotate without translational motion. Plunger 566 is pinned in place so that it cannot rotate, but the pins (not shown), which protrude from both sides of the plunger, are disposed in corresponding slots in the surrounding heater sleeve 567, allowing the plunger to move axially. As a result, rotation of gear 564 causes the plunger 566 to move axially forward.

Reservoir 568, which is forward of the plunger 566, contains a supply of polymer, which is melted by a heat source 570. Thus, as the plunger 566 moves forward, it dispenses the polymer from the reservoir 568 into the delivery tube 528 of the delivery tube assembly 522. The plunger includes an o-ring groove (not shown) to create a seal for the polymer. The reservoir and the delivery tube are preloaded with a supply of polymer, so that polymer will immediately flow from the distal end of the delivery tube the first time the trigger is squeezed. Because the plunger 566 moves a predetermined distance with each complete squeeze of the trigger 552, the surgeon is able to dispense a metered, predetermined amount of the polymer with each squeeze. When the supply of polymer is exhausted, the polymer delivery device is discarded.

The heat source 570 may be a proximal portion of the heating element 530, or may be a separate element. In either case, a differential level of heat may be applied at the reservoir and along the length of the delivery tube. For example, more heat may be applied at the reservoir than along the length of the delivery tube. It may be desirable to provide a switch (not shown) to shut off heat to a distal portion of the heating element 530, so that the polymer at the distal end of the delivery tube 528 solidifies after each delivery and thereby stops the flow of the polymer. A light or other indicator (not shown) may be provided on the housing 550 to indicate to the surgeon whether the polymer is sufficiently melted for dispensing.

When the trigger 552 is released, it is returned to its normal, uncompressed position by a return spring (not shown) within cartridge 572. As the gear rack 554 moves upward, it disengages from gear 558, preventing the gear 558 from turning in the reverse direction. The disengagement of the gear rack 554 from the gear 558 is facilitated by a return spring (not shown) which biases the rack towards the disengaged position.

The suture control assembly and polymer delivery assembly include alignment means (e.g., a locating pin on one assembly and a corresponding receiving slot on the other assembly, not shown) so that the surgeon can easily and correctly align the two assemblies. Correct alignment is important so that the nozzle 534 be positioned correctly to pick up the suture 452 as shown in FIG. 33. The two assemblies also generally include locking means, such as corresponding ball plungers and detents (not shown) which releasably lock the two assemblies together.

Figure 34:
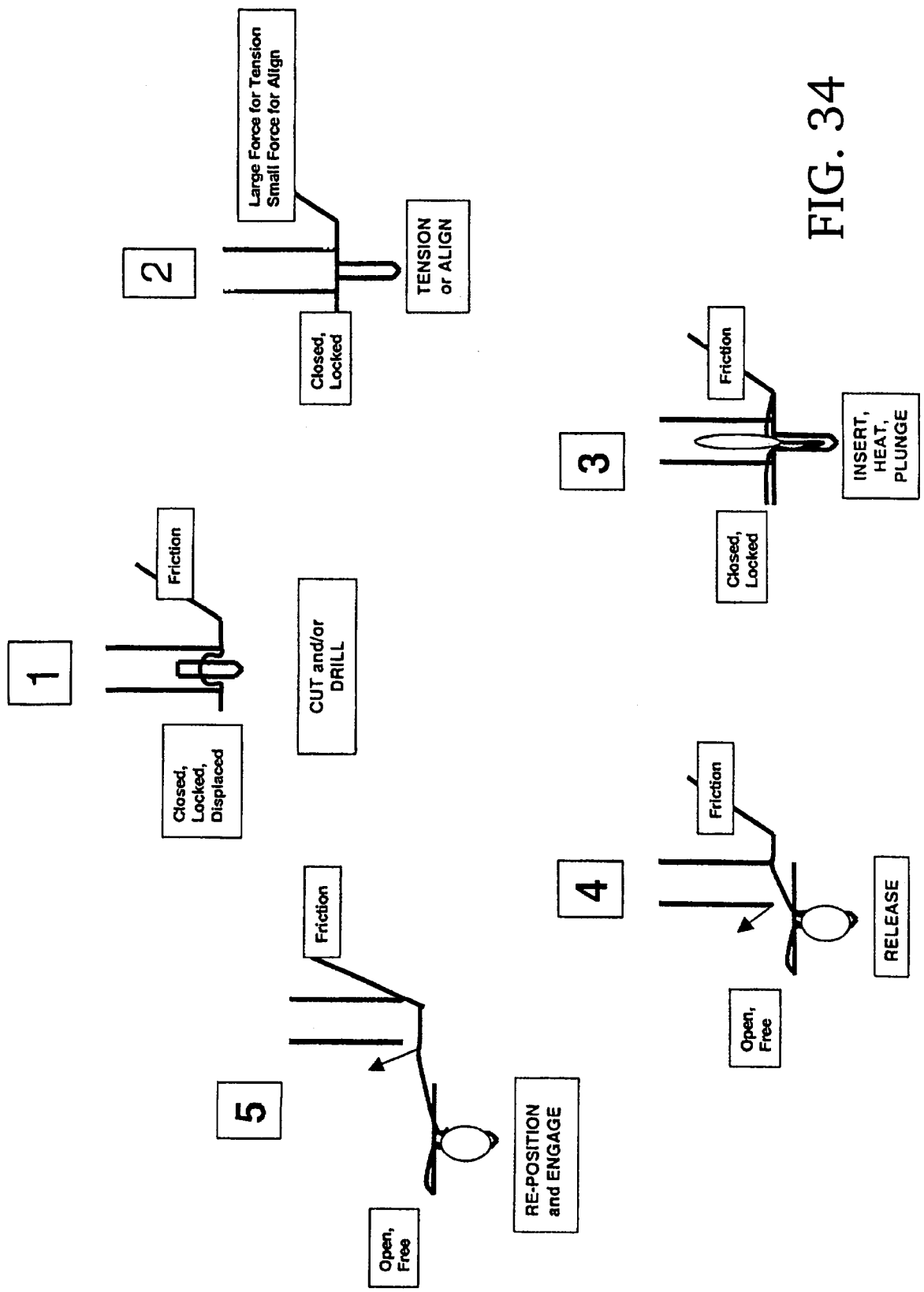
FIG. 34 is a schematic flow diagram illustrating steps in a procedure for forming a polymeric anchor.

A procedure using the surgical instrument 420 is shown schematically in FIG. 34.

The surgeon begins the procedure using the suture control assembly 422 alone, as it is shown in FIG. 23. Before using the surgical instrument, the surgeon locks the suture in place by rotating the suture lock/displacement knob 436 through an arc of 45 degrees, and displaces the suture so that it does not extend across the lumen of the surgical instrument (as shown in FIG. 28A) by rotating the knob 436 an additional 180 degrees (step 1). The surgeon then places the instrument in the surgical site, and approximates the soft tissue in the desired location for the first stitch.

The surgeon then inserts a drill through the lumen, and drills a hole in the bone. After the hole is drilled, the surgeon rotates the knob 436 in the reverse direction to "flip" the suture so that it again extends across the lumen (FIG. 28). The surgeon rotates the knob 436 only 180 degrees, so that the suture is "flipped" but is still locked in place. If desired, the surgeon can then tension the suture manually by rotating the manual tensioning knob 438. (Step 2)

At this stage, the surgeon assembles the polymer delivery assembly 424 onto the suture control assembly 422, as shown in FIG. 22. As discussed above, as the surgeon presses the two assemblies together, the nozzle 534 extends from the guide tube 526 (FIG. 31), forcing the suture into the hole (FIG. 30). The surgeon then squeezes the trigger 552 of the polymer delivery assembly 424, causing a metered amount of polymer to be delivered to the hole (step 3). If the surgeon believes that more polymer is necessary, the surgeon will squeeze the trigger again to deliver additional polymer. The nozzle 534 is retracted as the polymer is delivered. Before proceeding, the surgeon waits for the polymer to at least partially solidify, e.g., about 30 seconds.

To make additional stitches, the surgeon rotates the knob 436 a further 45 degrees in the reverse direction, to unlock the suture. The surgeon then pulls the distal end 440 of the surgical instrument axially, to remove the suture from the slot 468. This allows the surgeon to pull the instrument away from the solidified polymer. The surgeon then reengages the suture in the slot 468 and moves the distal end 440 transversely, in a desired direction, causing the suture 452 to unwind from spool 450. (Step 4) During this step, the suture is tensioned by the frictional force applied by the spring control device 448. The suture may be held in place in the slot by a frictional fit, or by other means such as an additional detent at less than 45 degrees, similar to the locking detent at 45 degrees that is discussed above.

When the surgeon reaches a desired location for the next stitch, the surgeon manually adjusts the suture tension, if desired, and locks the suture in place. (Step 5) The surgeon can then repeat the steps described above.

When the surgeon wishes to cut the suture, the surgeon places the suture in the locked position and cuts the suture using a separate device, e.g., a commonly available cutting tool.

Figure 35:
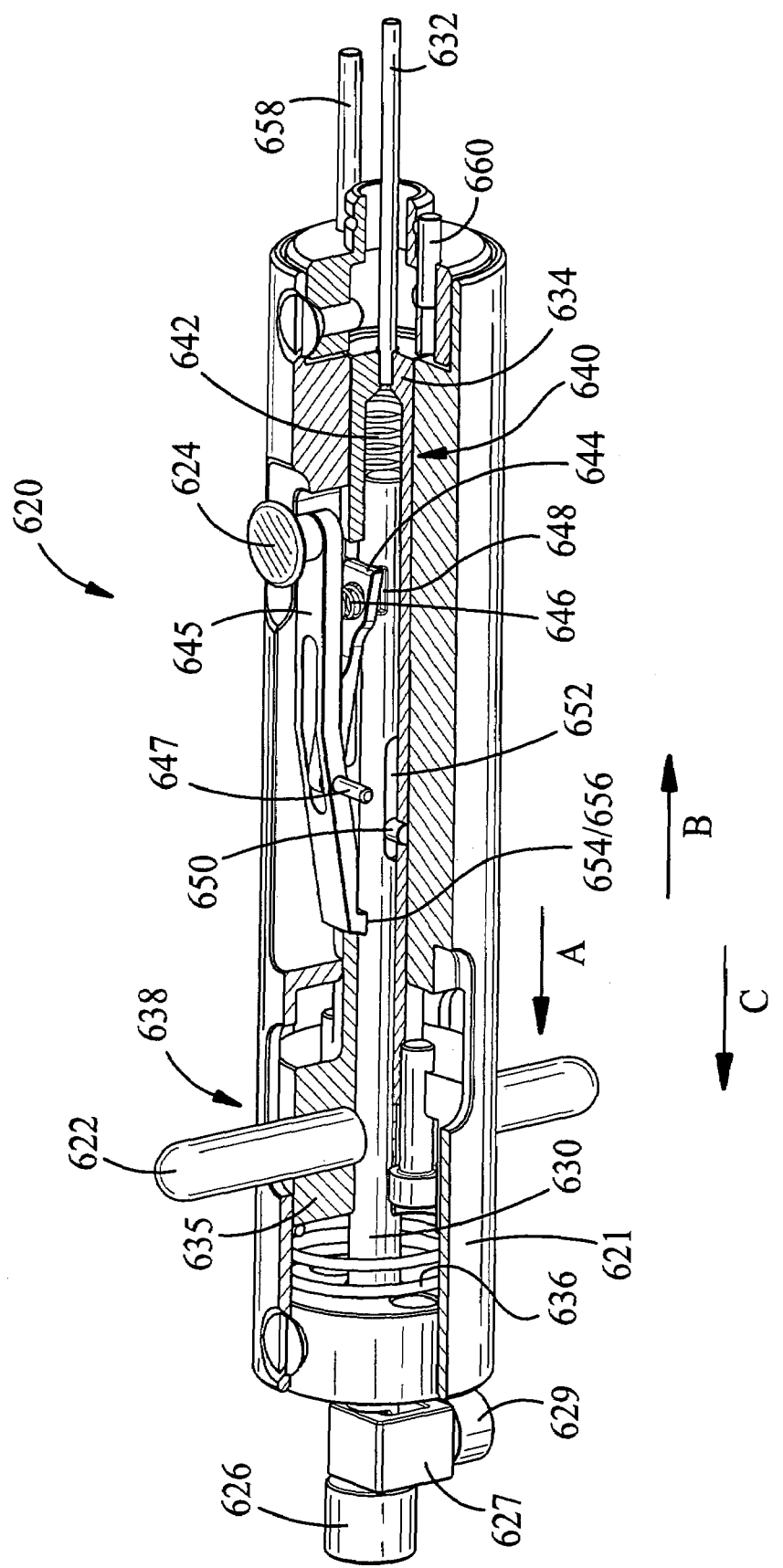
FIG. 35 is a perspective view, in partial cross-section, of an alternative polymer delivery assembly, which may be used with the suture control assembly shown in FIG. 23.

An alternative polymer delivery device 620, for supplying a polymer pellet to the bone hole and melting the polymer in situ, is shown in FIGS. 35–35B and described in detail below. This polymer delivery device may be substituted for the polymer delivery assembly 422 described above, and used with the same or a similar suture control assembly.

The polymer delivery device 620 includes a housing 621 and, extending from the housing, a cocking lever 622 and an actuating button 624. The housing defines an opening 626 for receiving an elongated heating element 628 (shown in FIG. 36 and described below), and a clamp 627 and a set screw 629 for clamping the elongated heating element 628 in place with respect to a transfer tube 630 through which the heating element 628 extends.

A plunger tube 632 extends distally from the housing, and defines a lumen for receiving the heating element 628. Plunger tube is mounted on a ram 634 that is spring-loaded by a spring 636 at its proximal end 635. The plunger tube may be moved to a "cocked" position, against the force of the spring 636, by pulling the cocking lever 622 axially in the direction of arrow A.

Lever 622 slides in slot 638 between the cocked position (shown) and a released, forward position (not shown). In the cocked position, the ram is forced back against the resisting force of spring 636, and held in place by an arm 645 on which actuating button 624 is mounted. Normally, the arm 645 is biased by a spring 646 into a position in which a lip 654 at the free end of the arm engages a slot 656 in the ram 634. The lip can be disengaged from the slot by pressing down on button 624. This released the ram to spring forward (arrow B), actuated by the force of the spring 636. This will in turn move the plunger tube 632 forward, to an extended position.

The distal end 640 of the transfer tube 630 is slidably mounted in a bore at the distal end of the ram 634, so that the transfer tube is capable of moving axially independent of the ram 634. The transfer tube is biased proximally by a spring 642. The transfer tube 630 is held in place axially, in a position that resists the biasing force of the spring 642, by a finger 644 that engages a receiving slot 648 on the transfer tube. Finger 644 is biased towards the slot by a spring 646, and can be lifted out of the slot 648 by depressing the actuating button 624. Pressure applied to button 624 scissors the finger 644 and arm 645 outward, about pivot 647, thus releasing both the ram and the transfer tube simultaneously. When the finger 644 is raised, the transfer tube 630 is free to slide axially within the housing, and as a result the transfer tube slides backwards (arrow C) in response to the biasing force of spring 642. Thus, as the ram and plunger tube spring forward, the transfer tube, in which the heating element 628 is held, simultaneously retracts.

When the surgeon wishes to retract the plunger tube and extend the heating element, the surgeon pulls the cocking lever 622, which has sprung forward with the ram, into its cocked position, in which the lip 654 is again engaged in the slot 656. The surgeon also pushes the transfer tube 630 forward, to engage finger 644 in slot 648.

Axial movement of the transfer tube 630 and ram 634 is guided by a pin 650 that is mounted on an inner wall of the housing and extends through aligned slots in the transfer tube and ram (slot 652 in the transfer tube is shown; the slot in the ram is not shown). The polymer delivery assembly 620 is aligned with a suture control assembly by locator pins 658 and 660.

Figure 36:
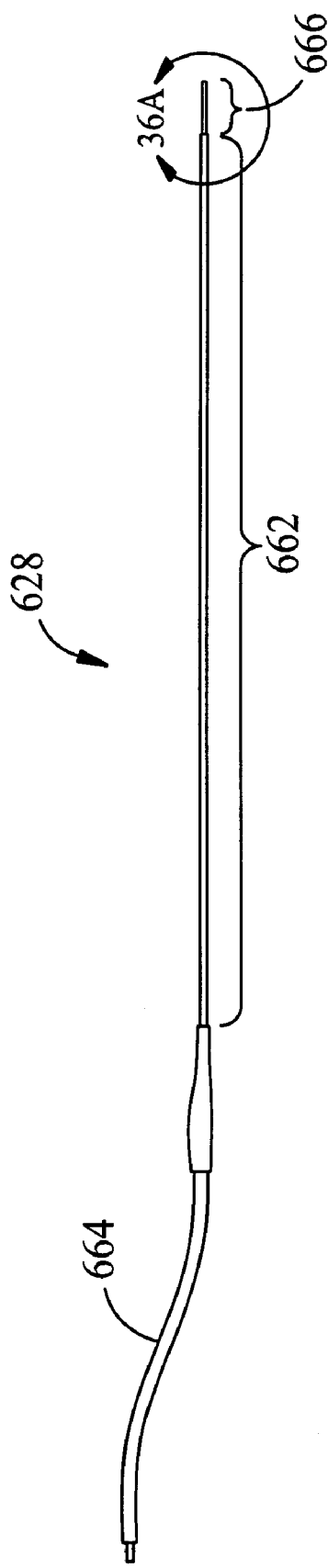
FIG. 36 is a side view of a heating element for use in the polymer delivery assembly of FIG. 35.
Figure 36A:
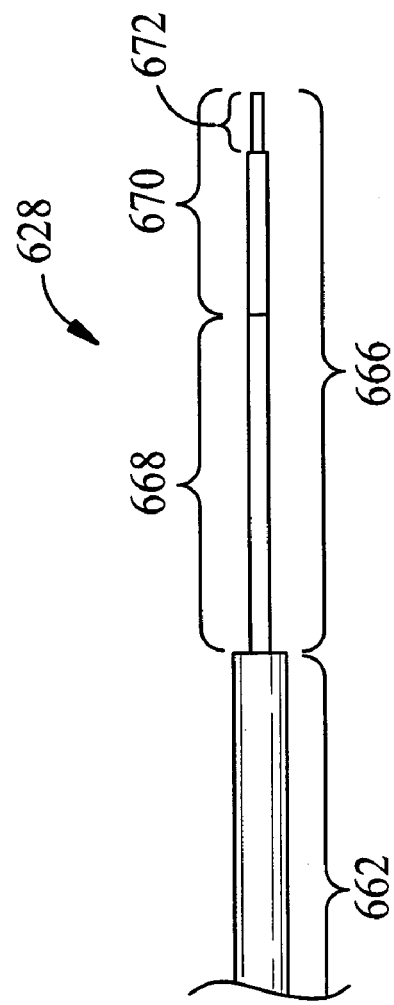
FIG. 36A is a highly enlarged detail view of area A in FIG. 36.

The heating element 628, shown in FIG. 36, includes an elongated portion 662, dimensioned to be inserted into the lumen of the plunger tube 632, connected at its proximal end to a pair of current-carrying wires 664, and terminating in a heating portion 666 at its distal end. Elongated portion 662 includes a stainless steel tube 661 (FIG. 36A), and, within the tube, a highly conductive insulated wire (not visible in FIGS. 36–36A), e.g., a magnet wire. The stainless steel tube 661 is covered with an insulating cover 663, for example, a heat shrink material. The stainless tube is plated along its entire length (as indicated by the exposed plated portion 668 shown in FIG. 36A), except for a high resistance, non-plated portion 670. The stainless tube is connected to the wire by a crimp at crimped tip region 672, completing a circuit and causing the plated tube to act as a return path for current. In non-plated portion 670, the current will encounter high resistance, due to the low electrical conductivity of the stainless steel, causing this portion to heat up. The rest of the length of the tube will not heat up significantly, due to the high conductivity and thus low resistance of the plated portion.

Figure 37:
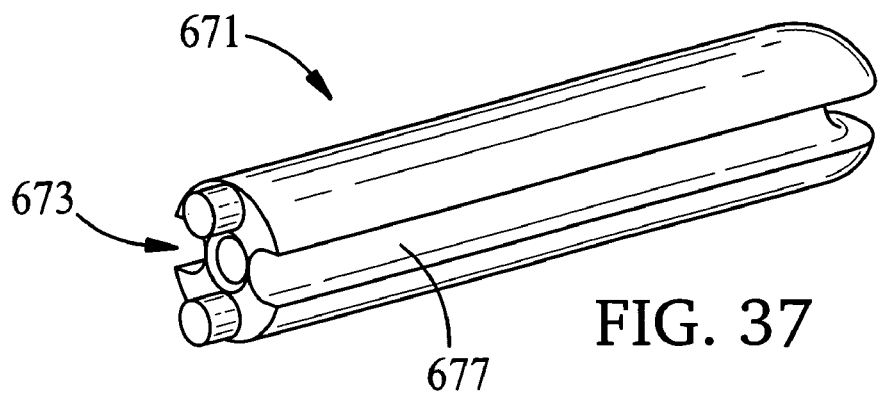
FIG. 37 is a perspective view of a polymer pellet suitable for use with the polymer delivery assembly shown in FIGS. 35–35B.
Figure 38:
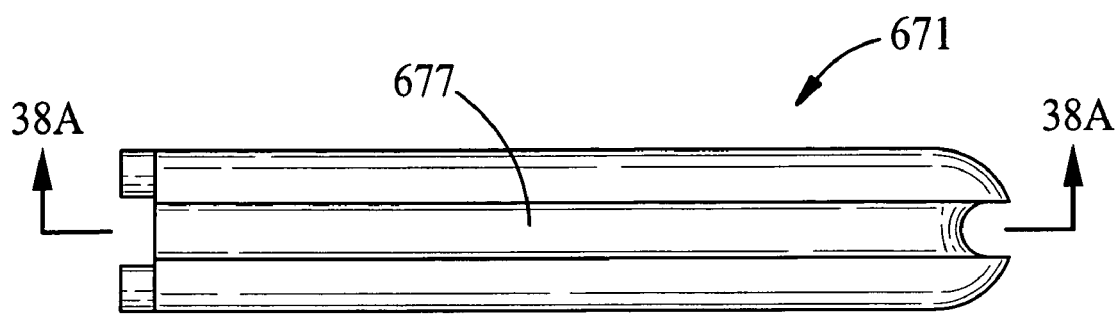
FIGS. 38–38B are, respectively, a side view, a cross-sectional view taken along line A—A of FIG. 38, and an end view, of the polymer pellet shown in FIG. 37.
Figure 38A:
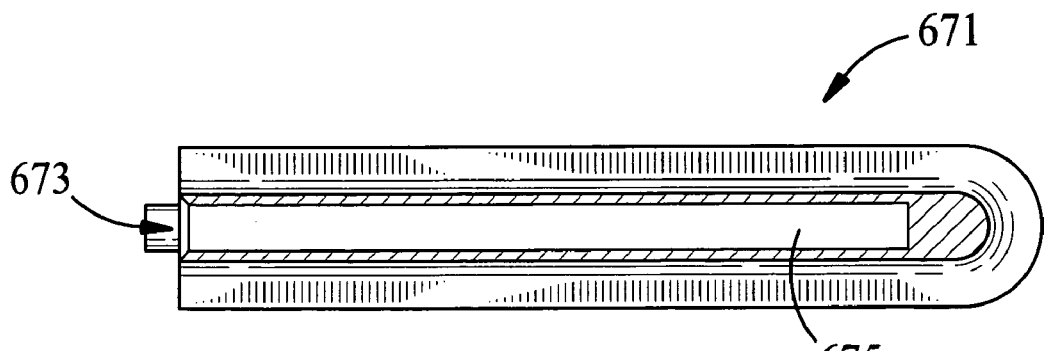
Figure 38B:
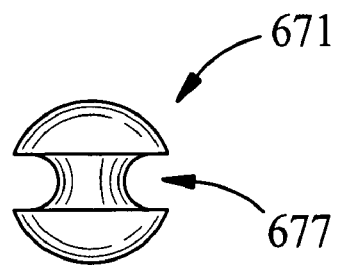

The crimped tip 672 of the heating element 628 is shaped to receive an elongated polymer pellet 671 (FIGS. 37–38B) having a corresponding opening 673 and bore 675 for receiving the tip 672. The length of the high resistance portion is selected to be approximately the same as the length of the polymer pellet, so that heat is delivered uniformly along the length of the pellet. The pellet includes a groove 677, similar to the groove 540 in nozzle 534, discussed above, dimensioned to receive and carry the suture.

The polymer delivery device 620 is used in a manner similar to that described above with reference to FIG. 34, with the exception of Step 3. In Step 3, instead of delivering an injection of molten polymer, the surgeon delivers a pellet of polymer. The pellet is delivered by placing it on the tip 672 of the heating element 628, and inserting the heating element 628 into the opening 626 in the polymer delivery device 620 and through the lumens of the transfer tube 630 and plunger tube 632. When the heating element is inserted, the surgeon pulls back on the cocking lever 622, to position the plunger tube in its retracted position, in which the lip 654 is again engaged in the slot 656. The surgeon also pushes the transfer tube 630 forward, to engage finger 644 in slot 648.

The tip of the pellet 671 includes a groove 677, similar to the groove 540 on nozzle 534, as discussed above. When the heating element is extended, the groove 677 picks up the suture and delivers it to the hole with the pellet, in the same manner as the nozzle 534 in the procedure described above. The surgeon then activates the heating portion 670 of the heating element 628 to melt the polymer pellet.

After melting the pellet, the surgeon depresses the actuating button on the polymer delivery device, which withdraws the heating element 628 from the hole, and causes the plunger tube 632 to spring forward and compact the molten polymer into the hole.

Suitable polymers for use in the methods described herein are thermoplastics that are acceptable for use in the body and can be delivered to a surgical site in a molten state. Preferably, the polymer will have a relatively low melting temperature to prevent thermal damage to tissue and bone during injection. For optimal deliverability, it is generally preferred that the polymer have an inherent viscosity of greater than about 0.6 dl/g, preferably about 0.6 to 0.7 dl/g, and an average molecular weight of greater than about 60,000 Mw, preferably about 60,000–70,000 Mw. The inherent viscosity is measured in chloroform, using the test described at col. 4, lines 33–36 of U.S. Pat. No. 5,679,723, which is incorporated herein by reference.

Preferably, the polymer used includes a resorbable polymer, e.g., polycaprolactone (PCL), which will slowly resorb during the natural healing process. The polymer may also include a non-resorbable polymer, e.g., polypropylene, polyacetal, polyethylene or polyurethane. The polymer may also include a blend of different resorbable polymers that resorb at different rates, e.g., blends of two or more of the following polymers: polycaprolactone (PCL), poly-1-lactic acid, poly-DL-lactic acid, polyglycolic acid, polydioxanone, polyglyconate, polytrimethylene carbonate, and copolymers of poly-L-lactic acid, poly-DL-lactic acid, polyglycolic acid, polydioxanone, polyglyconate, polytrimethylene carbonate, poly(hydroxyalkonates) (PHB, PHO, PHV), polyorthoesters, polyanhydrides, poly(pseudo-amino acids), poly(cyanoacrylates), poly(ester-anhydrides), polyoxalates, and polysaccharides. Other suitable polymers include poly-4-hydroxybutyrate (4PHB) and poly(alkylene oxalates).

As the polymer resorbs, the remaining, porous polymer resembles the trabecular network and thus encourages infiltration of osteoclasts, which cause breakdown of the polymer, and osteoblasts, which generate new bone. To encourage bone growth into the polymer, it is preferred that the polymer include an osteoconductive filler, e.g., hydroxyapatites (HA), calcium sulfates, tricalcium phosphates, bioactive glasses, aragonite, calcite, and mixtures of these fillers. A suitable level of osteoconductive filler will encourage bone growth without an unacceptable reduction in the deliverability of the polymer. Preferred levels are generally from about 0 to 40% by volume, most preferably about 30 to 40% by volume. Instead of or in addition to a conventional osteoconductive filler, the polymer may include bone fragments and debris, as discussed above. If bone fragments are used without another filler, it is generally preferred that the polymer include from about 0 to 60% bone fragments by weight, more preferably about 20 to 50% by weight.

The procedures discussed above may be used in many types of soft tissue fixation, including rotator cuff repair; instability repairs of the shoulder (e.g., SLAP, Bankart lesions, labral reattachment); repair or supplementation of anchors, screws and interference screws for attaching ACL autografts and allografts (e.g., bone-patella tendon-bone, Semigracilis, tendinosis, quadriceps autograft); and ACL repairs or revisions (e.g., where there is micromovement due to loosening of the fixation means and subsequent movement of the graft, or as a sealant to eliminate synovium fluid flow into bone hole cavities in ACL repair).

Endoscopic delivery of polymer may also be used in other applications, such as chondral repair, filling of harvest site defects in mosaicplasty, as an autograft diluent, refixation of small bony fragments, repair of osteochondritis dessicans (OCD) (i.e., by using injectable polymer to endoscopically reattach a loose flake of bone or cartilage, rather than pinning the flake in place), for spinal fusions, meniscal repair, fracture repair of non-load bearing bones, supplementation or augmentation of cancellous/cortical screws for long bone fractures especially in compromised or deficient bone, supplementation or augmentation of suture anchoring devices, in laparoscopic procedures to re-attach soft tissue to soft tissue or soft tissue to bone, and plastic surgery to aid in facial reconstruction.

Anchors of the invention generally provide good pull-out strengths. Pull-out strength will vary depending upon the suture, suture augmentation, number of sutures, and polymer used. For example, reduced pull-out strengths will be observed if a relatively weak suture material is used and the mode of failure is breakage of the suture. However, preferred anchors of the invention generally provide pull-out strengths of at least 150 Newtons, with some anchors providing strengths in excess of 300 Newtons, when tested in accordance with either of the test procedures (Test Procedures 1 and 2) described below. Pull-out strength is measured on cadaveric samples (shoulders) and on sawbone blocks (artificial bone), using the following test procedures.

Pull-Out Test Procedures

Test Procedure 1: Cadaveric Samples

All of the shoulders used would be harvested from fresh specimens, i.e., unpreserved, and stored at approximately −10 degrees Celsius until necessary for testing. Before testing, the specimens would be allowed to thaw to room temperature before dissecting and sample preparation.

The humerus would be prepared for the repair of a rotator cuff tear at the bony site. A cavity would be drilled to a depth of about 10 mm using a twist drill bit having a diameter of 3.3 mm. A suture, e.g., Spectra thread or similar suture material, would be delivered to the cavity, and the cavity would be filled with polymer. The polymer would be allowed to harden/set, after which the sample would be placed in an Instron servo-hydraulic testing machine, with the suture orientated parallel in relationship to the force applied by the testing machine.

The samples would be held in an appropriate vice/clamp which is itself attached to a 3-axis vice to permit the precise orientation of the samples being tested, using an appropriate Instron servo-hydraulic testing machine and associated Instron Max software, at a displacement rate of 8.5 mm/sec.

Test Procedure 2: Sawbone Block Samples

Samples would be prepared and tested as described above in Test Procedure 1, except that instead of a cadaveric humerus, the anchor would be formed in a sawbone block. A suitable sawbone block material is commercially available from Pacific Research, under the tradename "Sawbones".

Other embodiments are within the claims.

For example, although in most of the embodiments discussed above polymer is used as a substitute for a conventional bone anchor, in some cases it may be desirable to use the polymer to supplement the anchoring provided by a conventional anchor, e.g., by applying the polymer on top of or around the anchor when the anchor is placed. This option could be useful, for example, in cases in which the surgeon chooses to use a conventional anchor and the patient will be on an aggressive rehabilitation schedule.

Also, in some applications bone fragments harvested at one site may be mixed with polymer and injected at a second site in the same patient. This procedure may be used, for example, in cases in which the bone at the injection site is diseased or compromised, and fresh bone is desired as an autologous filler. In addition, bone fragments can be mixed into polymer within the cavity that is being formed, rather than extracting the bone fragments first as described above. This will occur, for example, when the drill bit is consumable.

Additionally, in certain circumstances multiple "bolt-like" polymer anchors could be used to attach a region of soft tissue to bone, rather than using a row of connected stitches.

Moreover, while the endoscopic procedures described above are generally preferred over open procedures because the endoscopic procedures are less invasive, similar techniques can be used in an open surgery environment if desired.

Further, while thermoplastic polymers have been discussed above, the polymer may be delivered in liquid, non-molten form and cured or dried in situ. For example, the polymer may be a thermoset polymer, e.g., a UV or laser curable material, may be electrolytic gelling, or may be in the form of a hydrogel (e.g., pH sensitive or ionic sensitive), a pluronic, or a sol-gel system, e.g. a polxamer polyol.

Moreover, non-polymeric flowable materials may be used in place of the polymer, e.g., injectable bone cements such as polyacrylic acid/divalent metal ion cements.

What is claimed is:

1. A surgical instrument for tissue fixation comprising:
    a handpiece constructed to be held by a surgeon during a fixation procedure;
    a cannulated tube defining a lumen, mounted on the handpiece;
    a delivery device, constructed to be mounted on the handpiece, for delivering a flowable material through the lumen to an opening in bone and comprising a heating element for heating said material to a flowable state; and
    a suture control device for delivering a suture material from a supply to a distal end of the cannulated tube.

2. The surgical instrument of claim 1 wherein the suture control device is constructed to control the tension applied to a free end of the suture.

3. The surgical instrument of claim 1 wherein the supply of suture material is disposed within the handpiece.

4. The surgical instrument of claim 1 wherein said delivery device further comprises a reservoir containing a supply of the flowable material, and said heating element is constructed to deliver heat to at least a portion of the reservoir.

5. The surgical instrument of claim 4 wherein the heating element is positioned adjacent at least a portion of the reservoir.

6. The surgical instrument of claim 4 wherein said delivery device further comprises a delivery tube in communication with the reservoir, the delivery tube being constructed to be disposed within the cannulated tube when the delivery device is mounted on the handpiece.

7. The surgical instrument of claim 6 wherein the heating element is constructed to deliver heat to the delivery tube.

8. The surgical instrument of claim 7 wherein the heating element includes a terminal portion, adjacent a distal end of the delivery tube, which can be turned off while heat is being delivered to the remainder of the heating element, so as to allow the flowable material at the distal end of the delivery tube to solidify and shut off flow from the delivery tube.

9. The surgical instrument of claim 6 wherein, prior to initial use of the surgical instrument, the delivery tube contains a supply of the flowable material.

10. The surgical instrument of claim 1 wherein said heating element comprises an elongated member having a tip constructed to deliver a polymer pellet through the lumen to the opening, the tip having an area to which heat can be delivered to melt the pellet.

11. The surgical instrument of claim 10 wherein said delivery device further comprises a plunger tube constructed to be disposed within the cannulated tube when the delivery device is mounted on the handpiece, and the elongated member is constructed to be inserted through the plunger tube.

12. The surgical instrument of claim 11, wherein said delivery device further comprises a mechanism for moving said plunger tube between an extended position and a retracted position.

13. The surgical instrument of claim 12 wherein said delivery device further comprises a mechanism for moving said elongated member between an extended position and a retracted position.

14. The surgical instrument of claim 13 wherein the mechanisms for moving the plunger tube and elongated member can be simultaneously activated by the surgeon, and operate counter to one another.

15. The surgical instrument of claim 10 wherein said heating element comprises a metal tube and, within the tube, an insulated current-carrying wire, the wire and tube being joined at a distal end to form a circuit, and the metal tube including a first portion having a relatively low resistance and a second, distal portion having a relatively higher resistance.

16. The surgical instrument of claim 1 wherein said delivery device comprises an elongated plunger constructed to be extended through the cannulated tube into the opening to compact the flowable material.

17. The surgical instrument of claim 16 wherein said elongated plunger defines a lumen through which a heating element is inserted into the opening.

18. The surgical instrument of claim 1 wherein said delivery device comprises an elongated nozzle having a distal end constructed to receive a portion of suture, and a mechanism constructed to extend the nozzle out of the distal end of the cannulated tube to push the portion of the suture into the opening and to retract the nozzle after delivery of the suture.

19. The surgical instrument of claim 18 wherein said elongated nozzle is cannulated to provide a path for delivery of the flowable material to the opening.

20. The surgical instrument of claim 1 wherein said delivery device comprises a mechanism for metering a predetermined dose of the flowable material.

21. The surgical instrument of claim 1 wherein said heating element is constructed to melt the material prior to delivery to the opening.

22. The surgical instrument of claim 1 wherein said heating element is constructed to melt the material after delivery to the opening.

23. The surgical instrument of claim 1 wherein said delivery device is detachable from said handpiece.

24. The surgical instrument of claim 1 wherein said suture control device comprises nested tubes, surrounding the cannulated tube, which define a path for the suture from the supply to the distal end.

25. The surgical instrument of claim 24 wherein said nested tubes include an outer tube, and a middle tube disposed between the outer tube and the cannulated tube, and the path is defined by a groove extending longitudinally along the length of the middle tube.

26. The surgical instrument of claim 1 wherein said suture control device comprises a suture lock, actuatable by the surgeon, to hold the suture in place at the distal end of the cannulated tube.

27. The surgical instrument of claim 1 wherein said suture control device comprises a suture displacement device for controlling the position of the suture at the distal end.

28. The surgical instrument of claim 1 wherein said suture control device comprises a tensioning device for maintaining tension on the suture.

29. The surgical instrument of claim 28 wherein the tensioning device is constructed to tighten a stitch formed with the suture.

30. The surgical instrument of claim 28 wherein the tensioning device comprises a spring mechanism.

31. The surgical instrument of claim 28 wherein said tensioning device is constructed to be manually actuated by the surgeon.

32. The surgical instrument of claim 1 wherein said surgical instrument is constructed to allow the surgeon to perform a complete fixation procedure at a surgical site without removing the cannulated tube from the surgical site.

33. A surgical instrument for tissue fixation comprising:
a handpiece constructed to be held by a surgeon during a fixation procedure;
a cannulated tube defining a lumen, mounted on the handpiece;
a cutting device, constructed to be positioned within the cannulated tube and to be removable therefrom by the surgeon; and
a delivery device for delivering a flowable material through the lumen to an opening in bone, the delivery device comprising a heating element for heating said material to a flowable state, the delivery device comprising a delivery tube that is constructed to be positioned within the cannulated tube, and to be removable therefrom by the surgeon.

34. The surgical instrument of claim 33 wherein the heating element is configured to heat the material within the opening.

35. The surgical instrument of claim 33 wherein said flowable material is delivered through the lumen in solid form.

36. The surgical instrument of claim 33 wherein said delivery device is configured to deliver a metered dose of the flowable material.

37. The surgical instrument of claim 33 wherein said delivery device further comprises a reservoir containing a supply of the flowable material, and said heating element is constructed to deliver heat to at least a portion of the reservoir.

38. The surgical instrument of claim 37 wherein the heating element is positioned adjacent at least a portion of the reservoir.

39. The surgical instrument of claim 37 wherein said delivery tube is in communication with the reservoir, the delivery tube being constructed to be disposed within the cannulated tube when the delivery device is mounted on the handpiece.

40. The surgical instrument of claim 39 wherein, prior to initial use of the surgical instrument, the delivery tube contains a supply of the flowable material.

41. The surgical instrument of claim 33 wherein the heating element is constructed to deliver heat to the delivery tube.

42. The surgical instrument of claim 41 wherein the heating element includes a terminal portion, adjacent a distal end of the delivery tube, which can be turned off while heat is being delivered to the remainder of the heating element, so as to allow the flowable material at the distal end of the delivery tube to solidify and shut off flow from the delivery tube.

43. The surgical instrument of claim 33 wherein said heating element comprises an elongated member having a tip constructed to deliver a polymer pellet through the lumen to the opening, the tip having an area to which heat can be delivered to melt the pellet.

44. The surgical instrument of claim 43 wherein said delivery device further comprises a plunger tube constructed to be disposed within the cannulated tube when the delivery device is mounted on the handpiece, and the elongated member is constructed to be inserted through the plunger tube.

45. The surgical instrument of claim 44, wherein said delivery device further comprises a mechanism for moving said plunger tube between an extended position and a retracted position.

46. The surgical instrument of claim 45 wherein said delivery device further comprises a mechanism for moving said elongated member between an extended position and a retracted position.

47. The surgical instrument of claim 46 wherein the mechanisms for moving the plunger tube and elongated member can be simultaneously activated by the surgeon, and operate counter to one another.

48. The surgical instrument of claim 43 wherein said heating element comprises a metal tube and, within the tube, an insulated current-carrying wire, the wire and tube being joined at a distal end to form a circuit, and the metal tube including a first portion having a relatively low resistance and a second, distal portion having a relatively higher resistance.

49. The surgical instrument of claim 33 wherein said delivery device comprises an elongated plunger constructed to be extended through the cannulated tube into the opening to compact the flowable material.

50. The surgical instrument of claim 49 wherein said elongated plunger defines a lumen through which a heating element is inserted into the opening.

51. The surgical instrument of claim 33 wherein said delivery device comprises an elongated nozzle having a distal end constructed to receive a portion of suture, and a mechanism constructed to extend the nozzle out of the distal end of the cannulated tube to push the portion of the suture into the opening and to retract the nozzle after delivery of the suture.

52. The surgical instrument of claim 51 wherein said elongated nozzle is cannulated to provide a path for delivery of the flowable material to the opening.

53. The surgical instrument of claim 33 wherein said heating element is constructed to melt the material prior to delivery to the opening.

54. The surgical instrument of claim 33 wherein said delivery device is detachable from said handpiece.

55. The surgical instrument of claim 33 wherein said surgical instrument is constructed to allow the surgeon to perform a complete fixation procedure at a surgical site without removing the cannulated tube from the surgical site.

56. A surgical instrument for tissue fixation comprising:
a handpiece constructed to be held by a surgeon during a fixation procedure;
a cannulated tube defining a lumen, mounted on the handpiece; and a delivery device for delivering a flowable material through the lumen to an opening in bone, the delivery device comprising
a reservoir containing a supply of the flowable material,
a delivery tube, in communication with the reservoir, constructed to be disposed within the cannulated tube when the delivery device is mounted on the handpiece,
a heating element constructed to deliver heat to at least a portion of the reservoir and to the delivery tube, thereby heating said material to a flowable state, and including a terminal portion, adjacent a distal end of the delivery tube, which can be turned off while heat is being delivered to the remainder of the heating element, so as to allow the flowable material at the distal end of the delivery tube to solidify and shut off flow from the delivery tube.

57. A surgical instrument for tissue fixation comprising:
a handpiece constructed to be held by a surgeon during a fixation procedure;
a cannulated tube defining a lumen, mounted on the handpiece; and a delivery device for delivering a flowable material through the lumen to an opening in bone, the delivery device comprising
a heating element for heating said material to a flowable state, and
an elongated plunger constructed to be extended through the cannulated tube into the opening to compact the flowable material, the elongated plunger defining a lumen through which a heating element is inserted into the opening.

58. A surgical instrument for tissue fixation comprising:
a handpiece constructed to be held by a surgeon during a fixation procedure;
a cannulated tube defining a lumen, mounted on the handpiece; and a delivery device for delivering a flowable material through the lumen to an opening in bone, the delivery device comprising
a heating element for heating said material to a flowable state,
an elongated nozzle having a distal end constructed to receive a portion of suture, and
a mechanism constructed to extend the nozzle out of the distal end of the cannulated tube to push the portion of the suture into the opening and to retract the nozzle after delivery of the suture.

* * * * *